(12) United States Patent
Ring et al.

(10) Patent No.: US 9,845,345 B2
(45) Date of Patent: Dec. 19, 2017

(54) SIRP POLYPEPTIDE COMPOSITIONS AND METHODS OF USE

(71) Applicant: Ab Initio Biotherapeutics, Inc., Los Altos, CA (US)

(72) Inventors: Aaron Michael Ring, Palo Alto, CA (US); Roy Louis Maute, San Francisco, CA (US); Andrew Curtis Kruse, Roslindale, MA (US); Aashish Manglik, Menlo Park, CA (US); Kenneth S. Lin, Los Altos, CA (US)

(73) Assignee: AB INITIO BIOTHERAPEUTICS, INC., Los Altos, CA (US)

( * ) Notice: Subject to any disclaimer, the term of this patent is extended or adjusted under 35 U.S.C. 154(b) by 0 days.

(21) Appl. No.: 15/157,291

(22) Filed: May 17, 2016

(65) Prior Publication Data

US 2016/0340397 A1 Nov. 24, 2016

Related U.S. Application Data

(60) Provisional application No. 62/266,450, filed on Dec. 11, 2015, provisional application No. 62/163,282, filed on May 18, 2015.

(51) Int. Cl.
| | | |
|---|---|---|
| C07K 14/00 | (2006.01) | |
| C07K 14/55 | (2006.01) | |
| C07K 14/47 | (2006.01) | |
| C07K 19/00 | (2006.01) | |
| C07K 14/705 | (2006.01) | |

(52) U.S. Cl.
CPC ........ *C07K 14/55* (2013.01); *C07K 14/70596* (2013.01); *C07K 2319/00* (2013.01); *C07K 2319/21* (2013.01); *C07K 2319/24* (2013.01); *C07K 2319/30* (2013.01); *C07K 2319/50* (2013.01)

(58) Field of Classification Search
None
See application file for complete search history.

(56) References Cited

U.S. PATENT DOCUMENTS

2010/0239579 A1  9/2010  Smith et al.
2015/0353642 A1*  12/2015  Tykocinski ...... C07K 14/70575
                                                                                          514/19.4

FOREIGN PATENT DOCUMENTS

WO   WO-2016187226 A1   11/2016

OTHER PUBLICATIONS

Lee et al. Novel structural determinants on SIRP alpha that mediate binding to CD47. J Immunol. 179:7741-7750 (Dec. 2007).
PCT/US2016/32921 International Search Report and Written Opinion dated Oct. 14, 2016.
Stefanidakis et al. Endothelial CD47 interaction with SIRP gamma is required for human T-cell transendothelial migration under shear flow conditions in vitro. Blood 112:1280-1289 (2008).

(Continued)

*Primary Examiner* — Claire Kaufman
(74) *Attorney, Agent, or Firm* — Wilson Sonsini Goodrich & Rosati

(57) ABSTRACT

Provided herein are SIRP-gamma, SIRP-beta or SIRP-beta2 decoy polypeptides for immunotherapy and/or treatment of cancer, anemia, transplant, asthma, allergy, auto-immune disease, and viral infection.

23 Claims, 12 Drawing Sheets

(56) References Cited

OTHER PUBLICATIONS

Bowie et al. Deciphering the message in protein sequences: tolerance to amino acid substitutions. Science 247:1306-1310 (1990).
Chao et al. Anti-CD47 antibody synergizes with rituximab to promote phagocytosis and eradicate non-Hodgkin lymphoma. Cell 142:699-713 (2010).
Cunningham et al. High-Resolution Epitope Mapping of hGH-Receptor Interactions by Alanine-Scanning Mutagenesis. Science 244:1081-1085 (1989).
De Vos et al. Human growth hormone and extracellular domain of its receptor: crystal structure of the complex. Science 255:306-312 (1992).
Hatherly et al. Paired Receptor Specificity Explained by Structures of Signal Regulatory Proteins Alone and Complexed with CD47. Molecular Cell 31:266-277 (2008).
Majeti et al. CD47 is an adverse prognostic factor and therapeutic antibody target on human acute myeloid leukemia stem cells. Cell 138:286-299 (2009).
Smith et al. Human interleukin 4. The solution structure of a four-helix bundle protein. J Mol Biol 224:899-904 (1992).
Weiskopf et al. Engineered SIRPα variants as immunotherapeutic adjuvants to anticancer antibodies. Science 341:88-91 (2013).
Weiskopf et al. Supplementary Materials for Engineered SIRPα variants as immunotherapeutic adjuvants to anticancer antibodies. Science. Available at www.sciencemag.org/cgi/content/full/science.1238856/DC1 (36 pgs.) (2013).

\* cited by examiner

FIG. 1
Surface plasmon resonance-based measurement of binding affinity and kinetics of the SIRP-gamma variant GV3 for human CD47.
FIG. 1A
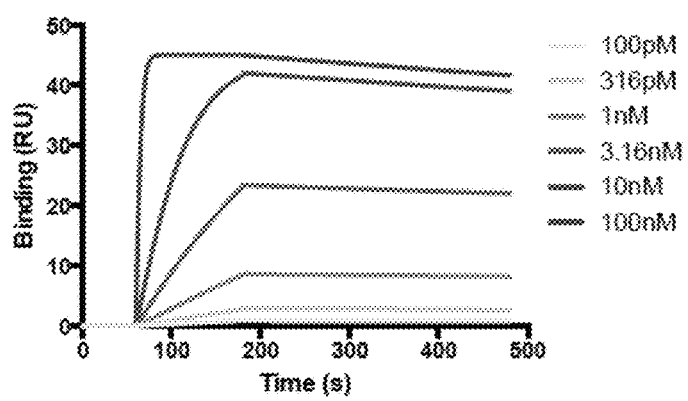
$K_D = 92\ pM$
$T_{1/2} = \sim 44\ min$
FIG. 1B
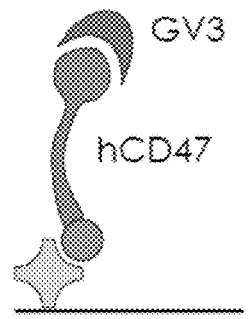

FIG. 2

Surface plasmon resonance-based measurement of binding affinity and kinetics of HAC-GV3, a fusion of the SIRP-gamma variant GV3 with a PD-1 variant HAC, for human CD47.

FIG. 2A

FIG. 2B $K_D = 160 \text{ pM}$ $T_{1/2} = \sim 40 \text{ min}$

FIG. 3

Surface plasmon resonance-based measurement of binding affinity and kinetics of HAC-GV3, a fusion of the SIRP-gamma variant GV3 with a PD-1 variant HAC, for human PD-L1.

FIG. 3A

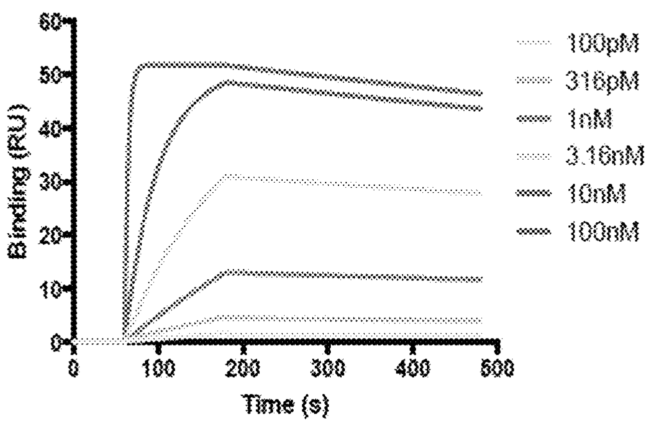

KD = 134 pM $T_{1/2}$ = ~38 min

FIG. 3B

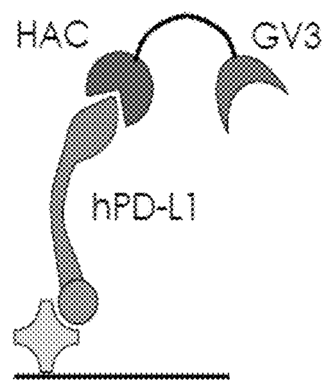

FIG. 4
Surface plasmon resonance-based measurement of the simultaneous binding of both human CD47 and human PD-L1 by HAC-GV3.
FIG. 4A
FIG. 4B
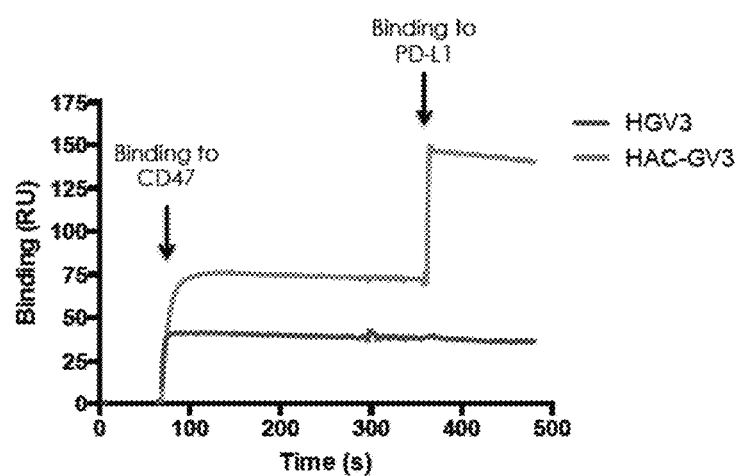
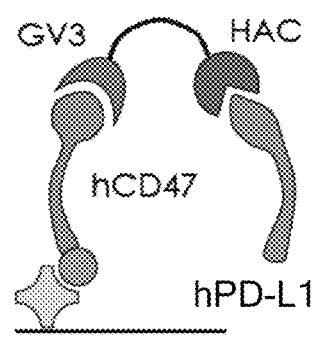

Flow cytometry-based measurement of blockade of CD47/SIRP-alpha interactions on the surface of CD47+ cells by GV3 and HAC-GV3.

Flow cytometry-based measurement of blockade of CD47/SIRP-alpha interactions on the surface of CD47+ PD-L1+ cells by GV3 and HAC-GV3.

Flow cytometry-based measurement of blockade of PD-1/PD-L1 interactions on the surface of PD-L1+ cells by HAC and HAC-GV3.

Flow cytometry-based measurement of blockade of PD-1/PD-L1 interactions on the surface of CD47+ PD-L1+ cells by HAC and HAC-GV3.

GV3 microbody and HAC-GV3 potentiate phagocytosis across a wide range of opsonizing antibody concentrations.

```
                          SEQUENCE LISTING

<160> NUMBER OF SEQ ID NOS: 46

<210> SEQ ID NO 1
<211> LENGTH: 119
<212> TYPE: PRT
<213> ORGANISM: Unknown
<220> FEATURE:
<223> OTHER INFORMATION: Description of Unknown:
      Wild type polypeptide

<400> SEQUENCE: 1

Glu Glu Glu Leu Gln Met Ile Gln Pro Glu Lys Leu Leu Leu Val Thr
1               5                   10                  15

Val Gly Lys Thr Ala Thr Leu His Cys Thr Val Thr Ser Leu Leu Pro
            20                  25                  30

Val Gly Pro Val Leu Trp Phe Arg Gly Val Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Ser Ser
65                  70                  75                  80

Ile Thr Pro Ala Asp Val Gly Thr Tyr Tyr Cys Val Lys Phe Arg Lys
                85                  90                  95

Gly Ser Pro Glu Asn Val Glu Phe Lys Ser Gly Pro Gly Thr Glu Met
            100                 105                 110

Ala Leu Gly Ala Lys Pro Ser
        115

<210> SEQ ID NO 2
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Met, Ile, Leu or Phe
<220> FEATURE:
<221> NAME/KEY: MOD_RES
<222> LOCATION: (27)..(27)
<223> OTHER INFORMATION: Phe, Ile, Leu or Val
<220> FEATURE:
<221> NAME/KEY: MOD_RES
<222> LOCATION: (30)..(30)
<223> OTHER INFORMATION: Leu, Ile, Val, His, Asn or Asp
<220> FEATURE:
<221> NAME/KEY: MOD_RES
<222> LOCATION: (31)..(31)
<223> OTHER INFORMATION: Phe, Ile, Leu or Val
<220> FEATURE:
<221> NAME/KEY: MOD_RES
```

```
<222> LOCATION: (33)..(33)
<223> OTHER INFORMATION: Val, Ile, Leu, Pro, Thr or Ala
<220> FEATURE:
<221> NAME/KEY: MOD_RES
<222> LOCATION: (36)..(36)
<223> OTHER INFORMATION: Val or Ile
<220> FEATURE:
<221> NAME/KEY: MOD_RES
<222> LOCATION: (37)..(37)
<223> OTHER INFORMATION: Leu or Gln
<220> FEATURE:
<221> NAME/KEY: MOD_RES
<222> LOCATION: (42)..(42)
<223> OTHER INFORMATION: Val or Ala
<220> FEATURE:
<221> NAME/KEY: MOD_RES
<222> LOCATION: (47)..(47)
<223> OTHER INFORMATION: Glu or Val
<220> FEATURE:
<221> NAME/KEY: MOD_RES
<222> LOCATION: (52)..(52)
<223> OTHER INFORMATION: Gln, Pro, Leu, Val, Ala or Glu
<220> FEATURE:
<221> NAME/KEY: MOD_RES
<222> LOCATION: (53)..(53)
<223> OTHER INFORMATION: Lys or Arg
<220> FEATURE:
<221> NAME/KEY: MOD_RES
<222> LOCATION: (54)..(54)
<223> OTHER INFORMATION: Glu, Asp, Lys, Asn, Gln or His
<220> FEATURE:
<221> NAME/KEY: MOD_RES
<222> LOCATION: (56)..(56)
<223> OTHER INFORMATION: His, Pro or Arg
<220> FEATURE:
<221> NAME/KEY: MOD_RES
<222> LOCATION: (66)..(66)
<223> OTHER INFORMATION: Leu, Ile, Val, Pro, Thr, Ala, Arg, Ser or Gly
<220> FEATURE:
<221> NAME/KEY: MOD_RES
<222> LOCATION: (67)..(67)
<223> OTHER INFORMATION: Thr, Ile, Asn, Phe, Ser, Tyr, Val, Ala or Asp
<220> FEATURE:
<221> NAME/KEY: MOD_RES
<222> LOCATION: (92)..(92)
<223> OTHER INFORMATION: Val or Ile
<220> FEATURE:
<221> NAME/KEY: MOD_RES
<222> LOCATION: (98)..(98)
<223> OTHER INFORMATION: Ser, Arg, Asn, Lys, Thr, Ile or Met
<220> FEATURE:
<221> NAME/KEY: MOD_RES
<222> LOCATION: (101)..(101)
<223> OTHER INFORMATION: Asn, Lys, Asp, Glu, His or Gln

<400> SEQUENCE: 2

Glu Glu Glu Leu Gln Xaa Ile Gln Pro Glu Lys Leu Leu Leu Val Thr
1               5                   10                  15

Val Gly Lys Thr Ala Thr Leu His Cys Thr Xaa Thr Ser Xaa Xaa Pro
            20                  25                  30

Xaa Gly Pro Xaa Xaa Trp Phe Arg Gly Xaa Gly Pro Gly Arg Xaa Leu
        35                  40                  45

Ile Tyr Asn Xaa Xaa Xaa Gly Xaa Phe Pro Arg Val Thr Thr Val Ser
    50                  55                  60

Asp Xaa Xaa Lys Arg Asn Asn Met Asp Phe Ser Ile Arg Ile Ser Ser
65                  70                  75                  80

Ile Thr Pro Ala Asp Val Gly Thr Tyr Tyr Cys Xaa Lys Phe Arg Lys
                85                  90                  95

Gly Xaa Pro Glu Xaa Val Glu Phe Lys Ser Gly Pro Gly Thr Glu Met
            100                 105                 110

Ala Leu Gly Ala Lys Pro Ser
```

```
            115

<210> SEQ ID NO 3
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Glu Glu Leu Gln Ile Ile Gln Pro Glu Lys Leu Leu Val Thr
1               5                   10                  15

Val Gly Lys Thr Ala Thr Leu His Cys Thr Ile Thr Ser Leu Phe Pro
            20                  25                  30

Val Gly Pro Val Leu Trp Phe Arg Gly Val Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Ser Ser
65                  70                  75                  80

Ile Thr Pro Ala Asp Val Gly Thr Tyr Tyr Cys Ile Lys Phe Arg Lys
                85                  90                  95

Gly Ser Pro Glu Asn Val Glu Phe Lys Ser Gly Pro Gly Thr Glu Met
            100                 105                 110

Ala Leu Gly Ala Lys Pro Ser
        115

<210> SEQ ID NO 4
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Glu Glu Leu Gln Ile Ile Gln Pro Glu Lys Leu Leu Val Thr
1               5                   10                  15

Val Gly Lys Thr Ala Thr Leu His Cys Thr Ile Thr Ser Leu Phe Pro
            20                  25                  30

Val Gly Pro Ile Gln Trp Phe Arg Gly Val Gly Pro Gly Arg Val Leu
        35                  40                  45

Ile Tyr Asn Gln Arg Asp Gly Pro Phe Pro Arg Val Thr Thr Val Ser
    50                  55                  60

Asp Gly Thr Lys Arg Asn Asn Met Asp Phe Ser Ile Arg Ile Ser Ser
65                  70                  75                  80

Ile Thr Pro Ala Asp Val Gly Thr Tyr Tyr Cys Val Lys Phe Arg Lys
                85                  90                  95

Gly Thr Pro Glu Asp Val Glu Phe Lys Ser Gly Pro Gly Thr Glu Met
            100                 105                 110

Ala Leu Gly Ala Lys Pro Ser
        115

<210> SEQ ID NO 5
<211> LENGTH: 119
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 5

Glu Glu Glu Leu Gln Ile Ile Gln Pro Glu Lys Leu Leu Val Thr
1               5                   10                  15

Val Gly Lys Thr Ala Thr Leu His Cys Thr Ile Thr Ser Leu Phe Pro
            20                  25                  30

Val Gly Pro Ile Gln Trp Phe Arg Gly Val Gly Pro Gly Arg Val Leu
        35                  40                  45

Ile Tyr Asn Gln Lys Asp Gly Pro Phe Pro Arg Val Thr Thr Val Ser
    50                  55                  60

Asp Gly Thr Lys Arg Asn Asn Met Asp Phe Ser Ile Arg Ile Ser Ser
65                  70                  75                  80

Ile Thr Pro Ala Asp Val Gly Thr Tyr Tyr Cys Val Lys Phe Arg Lys
                85                  90                  95

Gly Ser Pro Glu Asp Val Glu Phe Lys Ser Gly Pro Gly Thr Glu Met
            100                 105                 110

Ala Leu Gly Ala Lys Pro Ser
        115

<210> SEQ ID NO 6
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Glu Glu Leu Gln Ile Ile Gln Pro Glu Lys Leu Leu Val Thr
1               5                   10                  15

Val Gly Lys Thr Ala Thr Leu His Cys Thr Ile Thr Ser Leu Phe Pro
            20                  25                  30

Val Gly Pro Ile Gln Trp Phe Arg Gly Val Gly Pro Gly Arg Val Leu
        35                  40                  45

Ile Tyr Asn Gln Lys Asp Gly His Phe Pro Arg Val Thr Thr Val Ser
    50                  55                  60

Asp Gly Thr Lys Arg Asn Asn Met Asp Phe Ser Ile Arg Ile Ser Ser
65                  70                  75                  80

Ile Thr Pro Ala Asp Val Gly Thr Tyr Tyr Cys Val Lys Phe Arg Lys
                85                  90                  95

Gly Ser Pro Glu Asp Val Glu Phe Lys Ser Gly Pro Gly Thr Glu Met
            100                 105                 110

Ala Leu Gly Ala Lys Pro Ser
        115

<210> SEQ ID NO 7
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Glu Glu Leu Gln Ile Ile Gln Pro Glu Lys Leu Leu Val Thr
1               5                   10                  15

Val Gly Lys Thr Ala Thr Leu His Cys Thr Ile Thr Ser Leu Phe Pro
            20                  25                  30

Val Gly Pro Ile Gln Trp Phe Arg Gly Ala Gly Pro Gly Arg Val Leu
            35                  40                  45

Ile Tyr Asn Gln Arg Asp Gly Pro Phe Pro Arg Val Thr Thr Val Ser
    50                  55                  60

Asp Gly Thr Lys Arg Asn Asn Met Asp Phe Ser Ile Arg Ile Ser Ser
65                  70                  75                  80

Ile Thr Pro Ala Asp Val Gly Thr Tyr Tyr Cys Ile Lys Phe Arg Lys
                85                  90                  95

Gly Thr Pro Glu Asp Val Glu Phe Lys Ser Gly Pro Gly Thr Glu Met
            100                 105                 110

Ala Leu Gly Ala Lys Pro Ser
            115

<210> SEQ ID NO 8
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Glu Glu Leu Gln Ile Ile Gln Pro Glu Lys Leu Leu Val Val Thr
1               5                   10                  15

Val Gly Lys Thr Ala Thr Leu His Cys Thr Ile Thr Ser His Phe Pro
            20                  25                  30

Val Gly Pro Ile Gln Trp Phe Arg Gly Val Gly Pro Gly Arg Val Leu
            35                  40                  45

Ile Tyr Asn Gln Lys Asp Gly His Phe Pro Arg Val Thr Thr Val Ser
    50                  55                  60

Asp Gly Thr Lys Arg Asn Asn Met Asp Phe Ser Ile Arg Ile Ser Ser
65                  70                  75                  80

Ile Thr Pro Ala Asp Val Gly Thr Tyr Tyr Cys Val Lys Phe Arg Lys
                85                  90                  95

Gly Ser Pro Glu Asp Val Glu Phe Lys Ser Gly Pro Gly Thr Glu Met
            100                 105                 110

Ala Leu Gly Ala Lys Pro Ser
            115

<210> SEQ ID NO 9
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
            35                  40                  45

Ile Tyr Asn Gln Arg Asp Gly Pro Phe Pro Arg Val Thr Thr Val Ser
    50                  55                  60

Asp Gly Thr Lys Arg Asn Asn Met Asp Phe Ser Ile Arg Ile Ser Ser
65                  70                  75                  80

```
Ile Thr Pro Ala Asp Val Gly Thr Tyr Tyr Cys Val Lys Phe Arg Lys
                85                  90                  95

Gly Thr Pro Glu Asp Val Glu Phe Lys Ser Gly Pro Gly Thr Glu Met
            100                 105                 110

Ala Leu Gly Ala Lys Pro Ser
        115

<210> SEQ ID NO 10
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Glu Glu Leu Gln Ile Ile Gln Pro Glu Lys Leu Leu Leu Val Thr
1               5                   10                  15

Val Gly Lys Thr Ala Thr Leu His Cys Thr Ile Thr Ser Leu Phe Pro
            20                  25                  30

Val Gly Pro Val Leu Trp Phe Arg Gly Val Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Ser Ser
65                  70                  75                  80

Ile Thr Pro Ala Asp Val Gly Thr Tyr Tyr Cys Val Lys Phe Arg Lys
                85                  90                  95

Gly Thr Pro Glu Asp Val Glu Phe Lys Ser Gly Pro Gly Thr Glu Met
            100                 105                 110

Ala Leu Gly Ala Lys Pro Ser
        115

<210> SEQ ID NO 11
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Glu Glu Leu Gln Ile Ile Gln Pro Glu Lys Leu Leu Leu Val Thr
1               5                   10                  15

Val Gly Lys Thr Ala Thr Leu His Cys Thr Ile Thr Ser Leu Phe Pro
            20                  25                  30

Val Gly Pro Ile Gln Trp Phe Arg Gly Val Gly Pro Gly Arg Glu Leu
        35                  40                  45

Ile Tyr Asn Ala Arg Glu Gly Arg Phe Pro Arg Val Thr Thr Val Ser
    50                  55                  60

Asp Leu Thr Lys Arg Asn Asn Met Asp Phe Ser Ile Arg Ile Ser Ser
65                  70                  75                  80

Ile Thr Pro Ala Asp Val Gly Thr Tyr Tyr Cys Val Lys Phe Arg Lys
                85                  90                  95

Gly Ser Pro Glu Asp Val Glu Phe Lys Ser Gly Pro Gly Thr Glu Met
            100                 105                 110

Ala Leu Gly Ala Lys Pro Ser
        115
```

<210> SEQ ID NO 12
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 13
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Glu Glu Leu Gln Ile Ile Gln Pro Glu Lys Leu Leu Leu Val Thr
1               5                   10                  15

Val Gly Lys Thr Ala Thr Leu His Cys Thr Ile Thr Ser Leu Phe Pro
            20                  25                  30

Val Gly Pro Ile Gln Trp Phe Arg Gly Val Gly Pro Gly Arg Val Leu
        35                  40                  45

Ile Tyr Asn Gln Arg Glu Gly Pro Phe Pro Arg Val Thr Thr Val Ser
    50                  55                  60

Asp Gly Thr Lys Arg Asn Asn Met Asp Phe Ser Ile Arg Ile Ser Ser
65                  70                  75                  80

Ile Thr Pro Ala Asp Val Gly Thr Tyr Tyr Cys Val Lys Phe Arg Lys
                85                  90                  95

Gly Ser Pro Glu Asp Val Glu Phe Lys Ser Gly Pro Gly Thr Glu Met
            100                 105                 110

Ala Leu Gly Ala Lys Pro Ser
        115

<210> SEQ ID NO 14
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Asp Gly Pro Phe Pro Arg Val Thr Thr Val Ser
    50                  55                  60

Asp Gly Thr Lys Arg Asn Asn Met Asp Phe Ser Ile Arg Ile Ser Ser
65                  70                  75                  80

Ile Thr Pro Ala Asp Val Gly Thr Tyr Tyr Cys Ile Lys Phe Arg Lys
                85                  90                  95

Gly Ile Pro Glu Asp Val Glu Phe Lys Ser Gly Pro Gly Thr Glu Met
            100                 105                 110

Ala Leu Gly Ala Lys Pro Ser
        115

<210> SEQ ID NO 15
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (111)..(111)
<223> OTHER INFORMATION: Any amino acid

<400> SEQUENCE: 15

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Asp Gly Pro Phe Pro Arg Val Thr Thr Val Ser
    50                  55                  60

Asp Gly Thr Lys Arg Asn Asn Met Asp Phe Ser Ile Arg Ile Ser Ser
65                  70                  75                  80

Ile Thr Pro Ala Asp Val Gly Thr Tyr Tyr Cys Ile Lys Phe Arg Lys
                85                  90                  95

Gly Ile Pro Glu Asp Val Glu Phe Lys Ser Gly Pro Gly Thr Xaa Trp
            100                 105                 110

His

<210> SEQ ID NO 16
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Glu Glu Glu Leu Gln Ile Ile Gln Pro Asp Lys Ser Val Leu Val Ala
1               5                   10                  15

```
Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Lys Asp Gly Pro Phe Pro Arg Val Thr Thr Val Ser
    50                  55                  60

Asp Gly Thr Lys Arg Asn Asn Met Asp Phe Ser Ile Arg Ile Ser Ser
65                  70                  75                  80

Ile Thr Pro Ala Asp Val Gly Thr Tyr Tyr Cys Ile Lys Phe Arg Lys
                85                  90                  95

Gly Thr Pro Glu Asp Val Glu Phe Lys Ser Gly Pro Gly Thr Glu Met
            100                 105                 110

Ala Leu Gly Ala Lys Pro Ser
            115

<210> SEQ ID NO 17
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Glu Glu Leu Gln Ile Ile Gln Pro Glu Lys Leu Leu Leu Val Thr
1               5                   10                  15

Val Gly Lys Thr Ala Thr Leu His Cys Thr Ile Thr Ser Leu Leu Pro
            20                  25                  30

Val Gly Pro Ile Gln Trp Phe Arg Gly Val Gly Pro Gly Arg Glu Leu
        35                  40                  45

Ile Tyr Asn Gln Arg Asp Gly Pro Phe Pro Arg Val Thr Thr Val Ser
    50                  55                  60

Asp Gly Thr Lys Arg Asn Asn Met Asp Phe Ser Ile Arg Ile Ser Ser
65                  70                  75                  80

Ile Thr Pro Ala Asp Val Gly Thr Tyr Tyr Cys Val Lys Phe Arg Lys
                85                  90                  95

Gly Thr Pro Glu Asp Val Glu Phe Lys Ser Gly Pro Gly Thr Glu Met
            100                 105                 110

Ala Leu Gly Ala Lys Pro Ser
            115

<210> SEQ ID NO 18
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Glu Glu Leu Gln Ile Ile Gln Pro Glu Lys Leu Leu Leu Val Thr
1               5                   10                  15

Val Gly Lys Thr Ala Thr Leu His Cys Thr Leu Thr Ser Leu Leu Pro
            20                  25                  30

Val Gly Pro Ile Leu Trp Phe Arg Gly Val Gly Pro Gly Arg Val Leu
        35                  40                  45

Ile Tyr Asn Gln Arg Asp Gly Pro Phe Pro Arg Val Thr Thr Val Ser
    50                  55                  60
```

```
Asp Gly Thr Lys Arg Asn Asn Met Asp Phe Ser Ile Arg Ile Ser Ser
65                  70                  75                  80

Ile Thr Pro Ala Asp Val Gly Thr Tyr Tyr Cys Val Lys Phe Arg Lys
                85                  90                  95

Gly Asn Pro Glu Asp Val Glu Phe Lys Ser Gly Pro Gly Thr Glu Met
            100                 105                 110

Ala Leu Gly Ala Lys Pro Ser
            115

<210> SEQ ID NO 19
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Glu Glu Leu Gln Leu Ile Gln Pro Glu Lys Leu Leu Leu Val Thr
1               5                   10                  15

Val Gly Lys Thr Ala Thr Leu His Cys Thr Ile Thr Ser Leu Phe Pro
                20                  25                  30

Pro Gly Pro Ile Gln Trp Phe Arg Gly Val Gly Pro Gly Arg Val Leu
            35                  40                  45

Ile Tyr Asn Gln Lys Asp Gly Pro Phe Pro Arg Val Thr Thr Val Ser
    50                  55                  60

Asp Gly Thr Lys Arg Asn Asn Met Asp Phe Ser Ile Arg Ile Ser Ser
65                  70                  75                  80

Ile Thr Pro Ala Asp Val Gly Thr Tyr Tyr Cys Val Lys Phe Arg Lys
                85                  90                  95

Gly Ile Pro Glu Asp Val Glu Phe Lys Ser Gly Pro Gly Thr Glu Met
            100                 105                 110

Ala Leu Gly Ala Lys Pro Ser
            115

<210> SEQ ID NO 20
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Glu Glu Leu Gln Ile Ile Gln Pro Glu Lys Leu Leu Leu Val Thr
1               5                   10                  15

Val Gly Lys Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Val Leu
            35                  40                  45

Ile Tyr Asn Gln Arg Asp Gly Pro Phe Pro Arg Val Thr Thr Val Ser
    50                  55                  60

Asp Gly Thr Lys Arg Asn Asn Met Asp Phe Ser Ile Arg Ile Ser Ser
65                  70                  75                  80

Ile Thr Pro Ala Asp Val Gly Thr Tyr Tyr Cys Ile Lys Phe Arg Lys
                85                  90                  95

Gly Ile Pro Glu Asp Val Glu Phe Lys Ser Gly Pro Gly Thr Glu Met
            100                 105                 110
```

```
Ala Leu Gly Ala Lys Pro Ser
        115

<210> SEQ ID NO 21
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Glu Glu Leu Gln Ile Ile Gln Pro Glu Lys Leu Leu Val Thr
1               5                   10                  15

Val Gly Lys Thr Ala Thr Leu His Cys Thr Ile Thr Ser Leu Phe Pro
            20                  25                  30

Ile Gly Pro Ile Leu Trp Phe Arg Gly Val Gly Pro Gly Arg Val Leu
        35                  40                  45

Ile Tyr Asn Gln Lys Asp Gly Pro Phe Pro Arg Val Thr Thr Val Ser
    50                  55                  60

Asp Gly Thr Lys Arg Asn Asn Met Asp Phe Ser Ile Arg Ile Ser Ser
65                  70                  75                  80

Ile Thr Pro Ala Asp Val Gly Thr Tyr Tyr Cys Val Lys Phe Arg Lys
                85                  90                  95

Gly Ser Pro Glu Asp Val Glu Phe Lys Ser Gly Pro Gly Thr Glu Met
            100                 105                 110

Ala Leu Gly Ala Lys Pro Ser
        115

<210> SEQ ID NO 22
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Glu Glu Leu Gln Met Ile Gln Pro Glu Lys Leu Leu Val Thr
1               5                   10                  15

Val Gly Lys Thr Ala Thr Leu His Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Asp Gly Pro Phe Pro Arg Val Thr Thr Val Ser
    50                  55                  60

Asp Gly Thr Lys Arg Asn Asn Met Asp Phe Ser Ile Arg Ile Ser Ser
65                  70                  75                  80

Ile Thr Pro Ala Asp Val Gly Thr Tyr Tyr Cys Ile Lys Phe Arg Lys
                85                  90                  95

Gly Ile Pro Glu Asp Val Glu Phe Lys Ser Gly Pro Gly Thr Glu Met
            100                 105                 110

Ala Leu Gly Ala Lys Pro Ser
        115

<210> SEQ ID NO 23
<211> LENGTH: 119
<212> TYPE: PRT
<213> ORGANISM: Artificial Sequence
<220> FEATURE:
```

-continued

<223> OTHER INFORMATION: Description of Artificial Sequence: Synthetic
     polypeptide

<400> SEQUENCE: 23

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Val Gly Pro Gly Arg Val Leu
        35                  40                  45

Ile Tyr Asn Gln Lys Asp Gly Pro Phe Pro Arg Val Thr Thr Val Ser
    50                  55                  60

Asp Gly Thr Lys Arg Asn Asn Met Asp Phe Ser Ile Arg Ile Ser Ser
65                  70                  75                  80

Ile Thr Pro Ala Asp Val Gly Thr Tyr Tyr Cys Ile Lys Phe Arg Lys
                85                  90                  95

Gly Ile Pro Glu Asp Val Glu Phe Lys Ser Gly Pro Gly Thr Glu Met
            100                 105                 110

Ala Leu Gly Ala Lys Pro Ser
        115

<210> SEQ ID NO 24
<211> LENGTH: 119
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<221> NAME/KEY: MOD_RES
<222> LOCATION: (115)..(115)
<223> OTHER INFORMATION: Any amino acid

<400> SEQUENCE: 24

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Lys Asp Gly Pro Phe Pro Arg Val Thr Thr Val Ser
    50                  55                  60

Asp Gly Thr Lys Arg Asn Asn Met Asp Phe Ser Ile Arg Ile Ser Ser
65                  70                  75                  80

Ile Thr Pro Ala Asp Val Gly Thr Tyr Tyr Cys Ile Lys Phe Arg Lys
                85                  90                  95

Gly Thr Pro Glu Asp Val Glu Phe Lys Ser Gly Pro Gly Thr Glu Met
            100                 105                 110

Ala Leu Xaa Ala Lys Pro Ser
        115

<210> SEQ ID NO 25
<211> LENGTH: 119
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 25

```
Glu Asp Glu Leu Gln Val Ile Gln Pro Glu Lys Ser Val Ser Val Ala
1               5                   10                  15

Ala Gly Glu Ser Ala Thr Leu Arg Cys Ala Met Thr Ser Leu Ile Pro
            20                  25                  30

Val Gly Pro Ile Met Trp Phe Arg Gly Ala Gly Ala Gly Arg Glu Leu
        35                  40                  45

Ile Tyr Asn Gln Lys Glu Gly His Phe Pro Arg Val Thr Thr Val Ser
    50                  55                  60

Glu Leu Thr Lys Arg Asn Asn Leu Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115
```

<210> SEQ ID NO 26
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

```
Glu Asp Glu Leu Gln Ile Ile Gln Pro Glu Lys Ser Val Ser Val Ala
1               5                   10                  15

Ala Gly Glu Ser Ala Thr Leu Arg Cys Ala Ile Thr Ser Leu Phe Pro
            20                  25                  30

Val Gly Pro Ile Gln Trp Phe Arg Gly Ala Gly Ala Gly Arg Val Leu
        35                  40                  45

Ile Tyr Asn Gln Arg Gln Gly Pro Phe Pro Arg Val Thr Thr Val Ser
    50                  55                  60

Glu Thr Thr Lys Arg Asn Asn Leu Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115
```

<210> SEQ ID NO 27
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 27

```
Glu Glu Glu Leu Gln Val Ile Gln Pro Asp Lys Ser Ile Ser Val Ala
1               5                   10                  15

Ala Gly Glu Ser Ala Thr Leu His Cys Thr Val Thr Ser Leu Ile Pro
            20                  25                  30

Val Gly Pro Ile Gln Trp Phe Arg Gly Ala Gly Pro Gly Arg Glu Leu
        35                  40                  45
```

Ile Tyr Asn Gln Lys Glu Gly His Phe Pro Arg Val Thr Thr Val Ser
 50                  55                  60

Asp Leu Thr Lys Arg Asn Asn Met Asp Phe Ser Ile Arg Ile Ser Asn
65                  70                  75                  80

Ile Thr Pro Ala Asp Ala Gly Thr Tyr Tyr Cys Val Lys Phe Arg Lys
             85                  90                  95

Gly Ser Pro Asp His Val Glu Phe Lys Ser Gly Ala Gly Thr Glu Leu
            100                 105                 110

Ser Val Arg Ala Lys Pro Ser
        115

<210> SEQ ID NO 28
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Glu Glu Leu Gln Ile Ile Gln Pro Asp Lys Ser Ile Ser Val Ala
1               5                   10                  15

Ala Gly Glu Ser Ala Thr Leu His Cys Thr Ile Thr Ser Leu Phe Pro
             20                  25                  30

Val Gly Pro Ile Gln Trp Phe Arg Gly Ala Gly Pro Gly Arg Val Leu
         35                  40                  45

Ile Tyr Asn Gln Arg Gln Gly Pro Phe Pro Arg Val Thr Thr Val Ser
 50                  55                  60

Asp Thr Thr Lys Arg Asn Asn Met Asp Phe Ser Ile Arg Ile Ser Asn
65                  70                  75                  80

Ile Thr Pro Ala Asp Ala Gly Thr Tyr Tyr Cys Ile Lys Phe Arg Lys
             85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Gly Gly Gly Ser Gly Gly Gly Gly Ser
1               5                   10

<210> SEQ ID NO 30
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser

```
                20                  25                  30
Asn Thr Ser Glu Ser Phe His Val Val Trp His Arg Glu Ser Pro Ser
            35                  40                  45

Gly Gln Thr Asp Thr Leu Ala Ala Phe Pro Glu Asp Arg Ser Gln Pro
        50                  55                  60

Gly Gln Asp Ala Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Val Cys Gly Val Ile Ser Leu Ala Pro Lys Ile Gln Ile Lys Glu Ser
            100                 105                 110

Leu Arg Ala Glu Leu Arg Val Thr Glu Arg Gly Gly Gly Ser Gly
        115                 120                 125

Gly Gly Gly Ser Glu Glu Glu Leu Gln Ile Ile Gln Pro Glu Lys Leu
        130                 135                 140

Leu Leu Val Thr Val Gly Lys Thr Ala Thr Leu His Cys Thr Ile Thr
145                 150                 155                 160

Ser Leu Phe Pro Val Gly Pro Ile Gln Trp Phe Arg Gly Val Gly Pro
                165                 170                 175

Gly Arg Val Leu Ile Tyr Asn Gln Lys Asp Gly His Phe Pro Arg Val
            180                 185                 190

Thr Thr Val Ser Asp Gly Thr Lys Arg Asn Asn Met Asp Phe Ser Ile
        195                 200                 205

Arg Ile Ser Ser Ile Thr Pro Ala Asp Val Gly Thr Tyr Tyr Cys Val
        210                 215                 220

Lys Phe Arg Lys Gly Ser Pro Glu Asp Val Glu Phe Lys Ser Gly Pro
225                 230                 235                 240

Gly Thr Glu Met Ala Leu Gly Ala Lys Pro Ser
                245                 250

<210> SEQ ID NO 31
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Glu Glu Leu Gln Ile Ile Gln Pro Glu Lys Leu Leu Leu Val Thr
1               5                   10                  15

Val Gly Lys Thr Ala Thr Leu His Cys Thr Ile Thr Ser Leu Phe Pro
            20                  25                  30

Val Gly Pro Ile Gln Trp Phe Arg Gly Val Gly Pro Gly Arg Val Leu
        35                  40                  45

Ile Tyr Asn Gln Lys Asp Gly His Phe Pro Arg Val Thr Thr Val Ser
    50                  55                  60

Asp Gly Thr Lys Arg Asn Asn Met Asp Phe Ser Ile Arg Ile Ser Ser
65                  70                  75                  80

Ile Thr Pro Ala Asp Val Gly Thr Tyr Tyr Cys Val Lys Phe Arg Lys
                85                  90                  95

Gly Ser Pro Glu Asp Val Glu Phe Lys Ser Gly Pro Gly Thr Glu Met
            100                 105                 110

Ala Leu Gly Ala Lys Pro Ser Gly Gly Gly Ser Gly Gly Gly Gly
        115                 120                 125
```

```
Ser Trp Asn Ile His Gly Lys Glu Ser Cys Asp Val Gln Leu Tyr Ile
    130                 135                 140

Lys Arg Gln Ser Glu His Ser Ile Leu Ala Gly Asp Pro Phe Glu Leu
145                 150                 155                 160

Glu Cys Pro Val Lys Tyr Cys Ala Asn Arg Pro His Val Thr Trp Cys
                165                 170                 175

Lys Leu Asn Gly Thr Thr Cys Val Lys Leu Glu Asp Arg Gln Thr Ser
                180                 185                 190

Trp Lys Glu Lys Asn Ile Ser Phe Phe Ile Leu His Phe Glu Pro
                195                 200                 205

Val Leu Pro Asn Asp Asn Gly Ser Tyr Arg Cys Ser Ala Asn Phe Gln
210                 215                 220

Ser Asn Leu Ile Glu Ser His Ser Thr Thr Leu Tyr Val Thr Asp Val
225                 230                 235                 240

Lys

<210> SEQ ID NO 32
<211> LENGTH: 291
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Glu Glu Leu Gln Ile Ile Gln Pro Glu Lys Leu Leu Leu Val Thr
1               5                   10                  15

Val Gly Lys Thr Ala Thr Leu His Cys Thr Ile Thr Ser Leu Phe Pro
                20                  25                  30

Val Gly Pro Ile Gln Trp Phe Arg Gly Val Gly Pro Gly Arg Val Leu
            35                  40                  45

Ile Tyr Asn Gln Lys Asp Gly His Phe Pro Arg Val Thr Thr Val Ser
50                  55                  60

Asp Gly Thr Lys Arg Asn Asn Met Asp Phe Ser Ile Arg Ile Ser Ser
65                  70                  75                  80

Ile Thr Pro Ala Asp Val Gly Thr Tyr Tyr Cys Val Lys Phe Arg Lys
                85                  90                  95

Gly Ser Pro Glu Asp Val Glu Phe Lys Ser Gly Pro Gly Thr Glu Met
                100                 105                 110

Ala Leu Gly Ala Lys Pro Ser Gly Gly Gly Ser Gly Gly Gly Gly
            115                 120                 125

Ser Glu Leu Asn Gly Cys Ala Asn Pro Leu Gly Leu Lys Asn Asn Ser
    130                 135                 140

Ile Pro Asp Lys Gln Ile Thr Ala Ser Ser Tyr Lys Thr Trp Gly
145                 150                 155                 160

Leu His Leu Phe Ser Trp Asn Pro Ser Tyr Ala Arg Leu Asp Lys Gln
                165                 170                 175

Gly Asn Phe Asn Ala Trp Val Ala Gly Ser Tyr Gly Asn Asp Gln Trp
            180                 185                 190

Leu Gln Val Asp Leu Gly Ser Ser Lys Glu Val Thr Gly Ile Ile Thr
        195                 200                 205

Gln Gly Ala Arg Asn Phe Gly Ser Val Gln Phe Val Ala Ser Tyr Lys
    210                 215                 220

Val Ala Tyr Ser Asn Asp Ser Ala Asn Trp Thr Glu Tyr Gln Asp Pro
225                 230                 235                 240
```

-continued

```
Arg Thr Gly Ser Ser Lys Ile Phe Pro Gly Asn Trp Asp Asn His Ser
                245                 250                 255

His Lys Lys Asn Leu Phe Glu Thr Pro Ile Leu Ala Arg Tyr Val Arg
            260                 265                 270

Ile Leu Pro Val Ala Trp His Asn Arg Ile Ala Leu Arg Leu Glu Leu
        275                 280                 285

Leu Gly Cys
    290

<210> SEQ ID NO 33
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Glu Glu Leu Gln Ile Ile Gln Pro Glu Lys Leu Leu Leu Val Thr
1               5                   10                  15

Val Gly Lys Thr Ala Thr Leu His Cys Thr Ile Thr Ser Leu Phe Pro
            20                  25                  30

Val Gly Pro Ile Gln Trp Phe Arg Gly Val Gly Pro Gly Arg Val Leu
        35                  40                  45

Ile Tyr Asn Gln Lys Asp Gly His Phe Pro Arg Val Thr Thr Val Ser
    50                  55                  60

Asp Gly Thr Lys Arg Asn Asn Met Asp Phe Ser Ile Arg Ile Ser Ser
65                  70                  75                  80

Ile Thr Pro Ala Asp Val Gly Thr Tyr Tyr Cys Val Lys Phe Arg Lys
                85                  90                  95

Gly Ser Pro Glu Asp Val Glu Phe Lys Ser Gly Pro Gly Thr Glu Met
            100                 105                 110

Ala Leu Gly Ala Lys Pro Ser Gly Gly Gly Ser Gly Gly Gly Gly
        115                 120                 125

Ser Val Ala Gly Ser Val Lys Val Gly Gly Glu Ala Gly Pro Ser Val
130                 135                 140

Thr Leu Pro Cys His Tyr Ser Gly Ala Val Thr Ser Met Cys Trp Asn
145                 150                 155                 160

Arg Gly Ser Cys Ser Leu Phe Thr Cys Gln Asn Gly Ile Val Trp Thr
                165                 170                 175

Asn Gly Thr His Val Thr Tyr Arg Lys Asp Thr Arg Tyr Lys Leu Leu
            180                 185                 190

Gly Asp Leu Ser Arg Arg Asp Val Ser Leu Thr Ile Glu Asn Thr Ala
        195                 200                 205

Val Ser Asp Ser Gly Val Tyr Cys Cys Arg Val Glu His Arg Gly Trp
    210                 215                 220

Phe Asn Asp Met Lys Ile Thr Val Ser Leu Glu Ile Val Pro Pro Lys
225                 230                 235                 240

Val Thr Thr

<210> SEQ ID NO 34
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 34

```
Glu Glu Glu Leu Gln Ile Ile Gln Pro Glu Lys Leu Leu Val Thr
1               5                   10                  15

Val Gly Lys Thr Ala Thr Leu His Cys Thr Ile Thr Ser Leu Phe Pro
            20                  25                  30

Val Gly Pro Ile Gln Trp Phe Arg Gly Val Gly Pro Gly Arg Val Leu
        35                  40                  45

Ile Tyr Asn Gln Lys Asp Gly His Phe Pro Arg Val Thr Thr Val Ser
    50                  55                  60

Asp Gly Thr Lys Arg Asn Asn Met Asp Phe Ser Ile Arg Ile Ser Ser
65                  70                  75                  80

Ile Thr Pro Ala Asp Val Gly Thr Tyr Tyr Cys Val Lys Phe Arg Lys
                85                  90                  95

Gly Ser Pro Glu Asp Val Glu Phe Lys Ser Gly Pro Gly Thr Glu Met
            100                 105                 110

Ala Leu Gly Ala Lys Pro Ser Gly Gly Gly Ser Gly Gly Gly Gly
        115                 120                 125

Ser Ser Glu Val Glu Tyr Arg Ala Glu Val Gly Gln Asn Ala Tyr Leu
    130                 135                 140

Pro Cys Phe Tyr Thr Pro Ala Ala Pro Gly Asn Leu Val Pro Val Cys
145                 150                 155                 160

Trp Gly Lys Gly Ala Cys Pro Val Phe Glu Cys Gly Asn Val Val Leu
                165                 170                 175

Arg Thr Asp Glu Arg Asp Val Asn Tyr Trp Thr Ser Arg Tyr Trp Leu
            180                 185                 190

Asn Gly Asp Phe Arg Lys Gly Asp Val Ser Leu Thr Ile Glu Asn Val
        195                 200                 205

Thr Leu Ala Asp Ser Gly Ile Tyr Cys Cys Arg Ile Gln Ile Pro Gly
    210                 215                 220

Ile Met Asn Asp Glu Lys Phe Asn Leu Lys Leu Val Ile Lys Pro Ala
225                 230                 235                 240

Lys Val Thr Pro Ala
                245
```

<210> SEQ ID NO 35
<211> LENGTH: 263
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 35

```
Glu Glu Glu Leu Gln Ile Ile Gln Pro Glu Lys Leu Leu Val Thr
1               5                   10                  15

Val Gly Lys Thr Ala Thr Leu His Cys Thr Ile Thr Ser Leu Phe Pro
            20                  25                  30

Val Gly Pro Ile Gln Trp Phe Arg Gly Val Gly Pro Gly Arg Val Leu
        35                  40                  45

Ile Tyr Asn Gln Lys Asp Gly His Phe Pro Arg Val Thr Thr Val Ser
    50                  55                  60

Asp Gly Thr Lys Arg Asn Asn Met Asp Phe Ser Ile Arg Ile Ser Ser
65                  70                  75                  80

Ile Thr Pro Ala Asp Val Gly Thr Tyr Tyr Cys Val Lys Phe Arg Lys
                85                  90                  95
```

```
Gly Ser Pro Glu Asp Val Glu Phe Lys Ser Gly Pro Gly Thr Glu Met
            100                 105                 110

Ala Leu Gly Ala Lys Pro Ser Gly Gly Gly Ser Gly Gly Gly Gly
        115                 120                 125

Ser Thr Ser Glu Thr Val Val Thr Glu Val Leu Gly His Arg Val Thr
    130                 135                 140

Leu Pro Cys Leu Tyr Ser Ser Trp Ser His Asn Ser Asn Ser Met Cys
145                 150                 155                 160

Trp Gly Lys Asp Gln Cys Pro Tyr Ser Gly Cys Lys Glu Ala Leu Ile
                165                 170                 175

Arg Thr Asp Gly Met Arg Val Thr Ser Arg Lys Ser Ala Lys Tyr Arg
            180                 185                 190

Leu Gln Gly Thr Ile Pro Arg Gly Asp Val Ser Leu Thr Ile Leu Asn
        195                 200                 205

Pro Ser Glu Ser Asp Ser Gly Val Tyr Cys Cys Arg Ile Glu Val Pro
210                 215                 220

Gly Trp Phe Asn Asp Val Lys Ile Asn Val Arg Leu Asn Leu Gln Arg
225                 230                 235                 240

Ala Ser Thr Thr Thr Asp Glu Lys Phe Asn Leu Lys Leu Val Ile Lys
                245                 250                 255

Pro Ala Lys Val Thr Pro Ala
            260

<210> SEQ ID NO 36
<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Glu Glu Leu Gln Ile Ile Gln Pro Glu Lys Leu Leu Leu Val Thr
1               5                   10                  15

Val Gly Lys Thr Ala Thr Leu His Cys Thr Ile Thr Ser Leu Phe Pro
            20                  25                  30

Val Gly Pro Ile Gln Trp Phe Arg Gly Val Gly Pro Gly Arg Val Leu
        35                  40                  45

Ile Tyr Asn Gln Lys Asp Gly His Phe Pro Arg Val Thr Thr Val Ser
    50                  55                  60

Asp Gly Thr Lys Arg Asn Asn Met Asp Phe Ser Ile Arg Ile Ser Ser
65                  70                  75                  80

Ile Thr Pro Ala Asp Val Gly Thr Tyr Tyr Cys Val Lys Phe Arg Lys
                85                  90                  95

Gly Ser Pro Glu Asp Val Glu Phe Lys Ser Gly Pro Gly Thr Glu Met
            100                 105                 110

Ala Leu Gly Ala Lys Pro Ser Gly Gly Gly Ser Gly Gly Gly Gly
        115                 120                 125

Ser Gly Asp Gln Asn Pro Gln Ile Ala Ala His Val Ile Ser Glu Ala
    130                 135                 140

Ser Ser Lys Thr Thr Ser Val Leu Gln Trp Ala Glu Lys Gly Tyr Tyr
145                 150                 155                 160

Thr Met Ser Asn Asn Leu Val Thr Leu Glu Asn Gly Lys Gln Leu Thr
                165                 170                 175

Val Lys Arg Gln Gly Leu Tyr Tyr Ile Tyr Ala Gln Val Thr Phe Cys
            180                 185                 190
```

Ser Asn Arg Glu Ala Ser Ser Gln Ala Pro Phe Ile Ala Ser Leu Cys
                195                 200                 205

Leu Lys Ser Pro Gly Arg Phe Glu Arg Ile Leu Leu Arg Ala Ala Asn
    210                 215                 220

Thr His Ser Ser Ala Lys Pro Cys Gly Gln Gln Ser Ile His Leu Gly
225                 230                 235                 240

Gly Val Phe Glu Leu Gln Pro Gly Ala Ser Val Phe Val Asn Val Thr
                245                 250                 255

Asp Pro Ser Gln Val Ser His Gly Thr Gly Phe Thr Ser Phe Gly Leu
                260                 265                 270

Leu Lys Leu
        275

<210> SEQ ID NO 37
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Glu Glu Leu Gln Ile Ile Gln Pro Glu Lys Leu Leu Leu Val Thr
1               5                   10                  15

Val Gly Lys Thr Ala Thr Leu His Cys Thr Ile Thr Ser Leu Phe Pro
                20                  25                  30

Val Gly Pro Ile Gln Trp Phe Arg Gly Val Gly Pro Gly Arg Val Leu
            35                  40                  45

Ile Tyr Asn Gln Lys Asp Gly His Phe Pro Arg Val Thr Thr Val Ser
        50                  55                  60

Asp Gly Thr Lys Arg Asn Asn Met Asp Phe Ser Ile Arg Ile Ser Ser
65                  70                  75                  80

Ile Thr Pro Ala Asp Val Gly Thr Tyr Tyr Cys Val Lys Phe Arg Lys
                85                  90                  95

Gly Ser Pro Glu Asp Val Glu Phe Lys Ser Gly Pro Gly Thr Glu Met
                100                 105                 110

Ala Leu Gly Ala Lys Pro Ser Gly Gly Gly Ser Gly Gly Gly Gly
            115                 120                 125

Ser Asp Pro Ala Gly Leu Leu Asp Leu Arg Gln Gly Met Phe Ala Gln
    130                 135                 140

Leu Val Ala Gln Asn Val Leu Leu Ile Asp Gly Pro Leu Ser Trp Tyr
145                 150                 155                 160

Ser Asp Pro Gly Leu Ala Gly Val Ser Leu Thr Gly Gly Leu Ser Tyr
                165                 170                 175

Lys Glu Asp Thr Lys Glu Leu Val Val Ala Lys Ala Gly Val Tyr Tyr
                180                 185                 190

Val Phe Phe Gln Met Glu Leu Arg Arg Val Val Ala Gly Glu Gly Ser
            195                 200                 205

Gly Ser Val Ser Leu Ala Leu His Leu Met Pro Leu Arg Ser Ala Ala
    210                 215                 220

Gly Ala Ala Ala Leu Ala Leu Thr Val Asp Leu Pro Pro Ala Ser Ser
225                 230                 235                 240

Glu Ala Arg Asn Ser Ala Phe Gly Phe Gln Gly Arg Leu Leu His Leu
                245                 250                 255

Ser Ala Gly Gln Arg Leu Gly Val His Leu His Thr Glu Ala Arg Ala

```
                         260                 265                 270
Arg His Ala Trp Gln Leu Thr Gln Gly Ala Thr Val Leu Gly Leu Phe
            275                 280                 285
Arg Val Thr Pro Glu Ile Pro Ala
        290                 295

<210> SEQ ID NO 38
<211> LENGTH: 262
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Glu Glu Leu Gln Ile Ile Gln Pro Glu Lys Leu Leu Leu Val Thr
1               5                   10                  15

Val Gly Lys Thr Ala Thr Leu His Cys Thr Ile Thr Ser Leu Phe Pro
            20                  25                  30

Val Gly Pro Ile Gln Trp Phe Arg Gly Val Gly Pro Gly Arg Val Leu
        35                  40                  45

Ile Tyr Asn Gln Lys Asp Gly His Phe Pro Arg Val Thr Thr Val Ser
    50                  55                  60

Asp Gly Thr Lys Arg Asn Asn Met Asp Phe Ser Ile Arg Ile Ser Ser
65                  70                  75                  80

Ile Thr Pro Ala Asp Val Gly Thr Tyr Tyr Cys Val Lys Phe Arg Lys
                85                  90                  95

Gly Ser Pro Glu Asp Val Glu Phe Lys Ser Gly Pro Gly Thr Glu Met
            100                 105                 110

Ala Leu Gly Ala Lys Pro Ser Gly Gly Gly Ser Gly Gly Gly Gly
        115                 120                 125

Ser Ala Pro Thr Ser Ser Ser Thr Lys Lys Thr Gln Leu Gln Leu Glu
    130                 135                 140

His Leu Leu Leu Asp Leu Gln Met Ile Leu Asn Gly Ile Asn Asn Tyr
145                 150                 155                 160

Lys Asn Pro Lys Leu Thr Arg Met Leu Thr Phe Lys Phe Tyr Met Pro
                165                 170                 175

Lys Lys Ala Thr Glu Leu Lys His Leu Gln Cys Leu Glu Glu Glu Leu
            180                 185                 190

Lys Pro Leu Glu Glu Val Leu Asn Leu Ala Gln Ser Lys Asn Phe His
        195                 200                 205

Leu Arg Pro Arg Asp Leu Ile Ser Asn Ile Asn Val Ile Val Leu Glu
    210                 215                 220

Leu Lys Gly Ser Glu Thr Thr Phe Met Cys Glu Tyr Ala Asp Glu Thr
225                 230                 235                 240

Ala Thr Ile Val Glu Phe Leu Asn Arg Trp Ile Thr Phe Cys Gln Ser
                245                 250                 255

Ile Ile Ser Thr Leu Thr
            260

<210> SEQ ID NO 39
<211> LENGTH: 262
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 39

Glu Glu Glu Leu Gln Ile Ile Gln Pro Glu Lys Leu Leu Val Thr
1               5                   10                  15

Val Gly Lys Thr Ala Thr Leu His Cys Thr Ile Thr Ser Leu Phe Pro
            20                  25                  30

Val Gly Pro Ile Gln Trp Phe Arg Gly Val Gly Pro Gly Arg Val Leu
        35                  40                  45

Ile Tyr Asn Gln Lys Asp Gly His Phe Pro Arg Val Thr Thr Val Ser
    50                  55                  60

Asp Gly Thr Lys Arg Asn Asn Met Asp Phe Ser Ile Arg Ile Ser Ser
65                  70                  75                  80

Ile Thr Pro Ala Asp Val Gly Thr Tyr Tyr Cys Val Lys Phe Arg Lys
                85                  90                  95

Gly Ser Pro Glu Asp Val Glu Phe Lys Ser Gly Pro Gly Thr Glu Met
            100                 105                 110

Ala Leu Gly Ala Lys Pro Ser Gly Gly Gly Ser Gly Gly Gly Gly
        115                 120                 125

Ser Ala Pro Thr Ser Ser Ser Thr Lys Lys Thr Gln Leu Gln Leu Glu
130                 135                 140

His Leu Leu Leu Thr Leu Gln Met Ile Leu Asn Gly Ile Asn Asn Tyr
145                 150                 155                 160

Lys Asn Pro Lys Leu Thr Arg Met Leu Thr Ala Lys Phe Tyr Met Pro
                165                 170                 175

Lys Lys Ala Thr Glu Leu Lys His Leu Gln Cys Leu Glu Glu Glu Leu
            180                 185                 190

Lys Pro Leu Glu Glu Val Leu Asn Leu Ala Gln Ser Lys Asn Phe His
        195                 200                 205

Leu Arg Pro Arg Asp Leu Ile Ser Asn Ile Asn Val Ile Val Leu Glu
    210                 215                 220

Leu Lys Gly Ser Glu Thr Thr Phe Met Cys Glu Tyr Ala Asp Glu Thr
225                 230                 235                 240

Ala Thr Ile Val Glu Phe Leu Asn Arg Trp Ile Thr Phe Cys Gln Ser
                245                 250                 255

Ile Ile Ser Thr Leu Thr
            260

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 40

His His His His His His His His
1               5

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Leu Asn Asp Ile Phe Glu Ala Gln Lys Ile Glu Trp His Glu
```

<210> SEQ ID NO 42
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Glu Glu Leu Gln Met Ile Gln Pro Glu Lys Leu Leu Val Thr
1               5                   10                  15

Val Gly Lys Thr Ala Thr Leu His Cys Thr Val Thr Ser Leu Leu Pro
            20                  25                  30

Val Gly Pro Val Leu Trp Phe Arg Gly Val Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Ser Ser
65                  70                  75                  80

Ile Thr Pro Ala Asp Val Gly Thr Tyr Tyr Cys Val Lys Phe Arg Lys
                85                  90                  95

Gly Ser Pro Glu Asn Val Glu Phe Lys Ser Gly Pro Gly Thr Glu Met
            100                 105                 110

Ala Leu Gly Ala Lys Pro Ser
        115

<210> SEQ ID NO 43
<211> LENGTH: 119
<212> TYPE: PRT
<213> ORGANISM: Unknown
<220> FEATURE:
<223> OTHER INFORMATION: Description of Unknown:
      Wild type polypeptide

<400> SEQUENCE: 43

Glu Asp Glu Leu Gln Val Ile Gln Pro Glu Lys Ser Val Ser Val Ala
1               5                   10                  15

Ala Gly Glu Ser Ala Thr Leu Arg Cys Ala Met Thr Ser Leu Ile Pro
            20                  25                  30

Val Gly Pro Ile Met Trp Phe Arg Gly Ala Gly Ala Gly Arg Glu Leu
        35                  40                  45

Ile Tyr Asn Gln Lys Glu Gly His Phe Pro Arg Val Thr Thr Val Ser
    50                  55                  60

Glu Leu Thr Lys Arg Asn Asn Leu Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 44
<211> LENGTH: 119
<212> TYPE: PRT
<213> ORGANISM: Unknown
<220> FEATURE:
<223> OTHER INFORMATION: Description of Unknown:

Wild type polypeptide

<400> SEQUENCE: 44

Glu Glu Glu Leu Gln Val Ile Gln Pro Asp Lys Ser Ile Ser Val Ala
1               5                   10                  15

Ala Gly Glu Ser Ala Thr Leu His Cys Thr Val Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp His Val Glu Phe Lys Ser Gly Ala Gly Thr Glu Leu
            100                 105                 110

Ser Val Arg Ala Lys Pro Ser
        115

<210> SEQ ID NO 45
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Val or Ile
<220> FEATURE:
<221> NAME/KEY: MOD_RES
<222> LOCATION: (27)..(27)
<223> OTHER INFORMATION: Met or Ile
<220> FEATURE:
<221> NAME/KEY: MOD_RES
<222> LOCATION: (31)..(31)
<223> OTHER INFORMATION: Ile or Phe
<220> FEATURE:
<221> NAME/KEY: MOD_RES
<222> LOCATION: (37)..(37)
<223> OTHER INFORMATION: Met or Gln
<220> FEATURE:
<221> NAME/KEY: MOD_RES
<222> LOCATION: (47)..(47)
<223> OTHER INFORMATION: Glu or Val
<220> FEATURE:
<221> NAME/KEY: MOD_RES
<222> LOCATION: (53)..(53)
<223> OTHER INFORMATION: Lys or Arg
<220> FEATURE:
<221> NAME/KEY: MOD_RES
<222> LOCATION: (54)..(54)
<223> OTHER INFORMATION: Glu or Gln
<220> FEATURE:
<221> NAME/KEY: MOD_RES
<222> LOCATION: (56)..(56)
<223> OTHER INFORMATION: His or Pro
<220> FEATURE:
<221> NAME/KEY: MOD_RES
<222> LOCATION: (66)..(66)
<223> OTHER INFORMATION: Leu or Thr
<220> FEATURE:
<221> NAME/KEY: MOD_RES
<222> LOCATION: (92)..(92)
<223> OTHER INFORMATION: Val or Ile

<400> SEQUENCE: 45

```
Glu Asp Glu Leu Gln Xaa Ile Gln Pro Glu Lys Ser Val Ser Val Ala
1               5                   10                  15

Ala Gly Glu Ser Ala Thr Leu Arg Cys Ala Xaa Thr Ser Leu Xaa Pro
            20                  25                  30

Val Gly Pro Ile Xaa Trp Phe Arg Gly Ala Gly Ala Gly Arg Xaa Leu
            35                  40                  45

Ile Tyr Asn Gln Xaa Xaa Gly Xaa Phe Pro Arg Val Thr Thr Val Ser
        50                  55                  60

Glu Xaa Thr Lys Arg Asn Asn Leu Asp Phe Ser Ile Ser Ile Ser Asn
65                  70                  75                  80

Ile Thr Pro Ala Asp Ala Gly Thr Tyr Tyr Cys Xaa Lys Phe Arg Lys
                85                  90                  95

Gly Ser Pro Asp Asp Val Glu Phe Lys Ser Gly Ala Gly Thr Glu Leu
                100                 105                 110

Ser Val Arg Ala Lys Pro Ser
            115
```

<210> SEQ ID NO 46
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Val or Ile
<220> FEATURE:
<221> NAME/KEY: MOD_RES
<222> LOCATION: (27)..(27)
<223> OTHER INFORMATION: Val or Ile
<220> FEATURE:
<221> NAME/KEY: MOD_RES
<222> LOCATION: (31)..(31)
<223> OTHER INFORMATION: Ile or Phe
<220> FEATURE:
<221> NAME/KEY: MOD_RES
<222> LOCATION: (47)..(47)
<223> OTHER INFORMATION: Glu or Val
<220> FEATURE:
<221> NAME/KEY: MOD_RES
<222> LOCATION: (53)..(53)
<223> OTHER INFORMATION: Lys or Arg
<220> FEATURE:
<221> NAME/KEY: MOD_RES
<222> LOCATION: (54)..(54)
<223> OTHER INFORMATION: Glu or Gln
<220> FEATURE:
<221> NAME/KEY: MOD_RES
<222> LOCATION: (56)..(56)
<223> OTHER INFORMATION: His or Pro
<220> FEATURE:
<221> NAME/KEY: MOD_RES
<222> LOCATION: (66)..(66)
<223> OTHER INFORMATION: Leu or Thr
<220> FEATURE:
<221> NAME/KEY: MOD_RES
<222> LOCATION: (92)..(92)
<223> OTHER INFORMATION: Val or Ile
<220> FEATURE:
<221> NAME/KEY: MOD_RES
<222> LOCATION: (101)..(101)
<223> OTHER INFORMATION: His or Asp

<400> SEQUENCE: 46

```
Glu Glu Glu Leu Gln Xaa Ile Gln Pro Asp Lys Ser Ile Ser Val Ala
1               5                   10                  15

Ala Gly Glu Ser Ala Thr Leu His Cys Thr Xaa Thr Ser Leu Xaa Pro
```

-continued

```
                     20                  25                  30
Val Gly Pro Ile Gln Trp Phe Arg Gly Ala Gly Pro Gly Arg Xaa Leu
            35                  40                  45

Ile Tyr Asn Gln Xaa Xaa Gly Xaa Phe Pro Arg Val Thr Thr Val Ser
        50                  55                  60

Asp Xaa Thr Lys Arg Asn Asn Met Asp Phe Ser Ile Arg Ile Ser Asn
 65                  70                  75                  80

Ile Thr Pro Ala Asp Ala Gly Thr Tyr Tyr Cys Xaa Lys Phe Arg Lys
                85                  90                  95

Gly Ser Pro Asp Xaa Val Glu Phe Lys Ser Gly Ala Gly Thr Glu Leu
            100                 105                 110

Ser Val Arg Ala Lys Pro Ser
            115
```

US 9,845,345 B2

SIRP POLYPEPTIDE COMPOSITIONS AND METHODS OF USE

CROSS-REFERENCE

This application claims the benefit of U.S. Provisional Application No. 62/266,450, filed Dec. 11, 2015 and U.S. Provisional Application No. 62/163,282, filed May 18, 2015, both of which applications are incorporated herein by reference in their entirety.

SEQUENCE LISTING

The instant application contains a Sequence Listing which has been submitted electronically in ASCII format and is hereby incorporated by reference in its entirety. Said ASCII copy, created on May 17, 2016, is named 47815-701.201_SL.txt and is 66,023 bytes in size.

BACKGROUND OF THE INVENTION

Signal regulatory proteins (SIRPs) constitute a family of cell surface glycoproteins which are expressed on myeloid cells (including macrophages, granulocytes, myeloid dendritic cells, and mast cells), lymphocytes, and neuronal cells and regulate their activity.

SUMMARY OF THE INVENTION

SIRP-gamma, SIRP-beta or SIRP-beta2 decoy polypeptides and analogs thereof are provided which may be referred within as decoy polypeptides. In one embodiment there is provided a decoy polypeptide comprising a SIRP-gamma, a SIRP-beta or a SIRP-beta2 polypeptide, wherein the polypeptide comprises at least one amino acid modification to increase affinity of the decoy SIRP-gamma, SIRP-beta or SIRP-beta2 polypeptide binding to CD47 as compared to the affinity for CD47 of the corresponding wild type SIRP-gamma, SIRP-beta or SIRP-beta2 polypeptide. In particular aspects, the polypeptide comprises a SIRP-gamma polypeptide with the sequence EEELQMIQPEKLLLVT-VGKTATLHCTVTSLLPVGPVLWFRGVGPGRELIYN-QKEGHFPRVTTVSDLT KRNNMDFSIRISSITPADVG-TYYCVKFRKGSPENVEFKSGPGTEMALGAKPS (SEQ ID NO: 1). In additional aspects, the SIRP-gamma polypeptide is 90% identical to a wildtype SIRP-gamma polypeptide. In further aspects, the SIRP-gamma polypeptide has an amino acid substitution at M6, V27, L30, L31, V33, V36, L37, V42, E47, Q52, K53, E54, H56, L66, T67, V92, S98 or N101. In additional aspects, the SIRP-gamma polypeptide has a substitution at M6 wherein the substitution is I, L or F. In further aspects, the SIRP-gamma polypeptide has a substitution at V27 wherein the substitution is F, I or L. In additional aspects, the SIRP-gamma polypeptide has a substitution at L30 wherein the substitution is I, V, H, N or D. In further aspects, the SIRP-gamma polypeptide has a substitution at L31 wherein the substitution is F, I or V. In additional aspects, the SIRP-gamma polypeptide has a substitution at V33 wherein the substitution is I, L, P, T or A. In further aspects, the SIRP-gamma polypeptide has a substitution at V36 wherein the substitution is I. In further aspects, the SIRP-gamma polypeptide has a substitution at L37 wherein the substitution is Q. In further aspects, the SIRP-gamma polypeptide has a substitution at V42 wherein the substitution is A. In additional aspects, the SIRP-gamma polypeptide has a substitution at E47 wherein the substitution is V. In further aspects, the SIRP-gamma polypeptide has a substitution at Q52 wherein the substitution is P, L, V, A or E. In further aspects, the SIRP-gamma polypeptide has a substitution at K53 wherein the substitution is R. In additional aspects, the SIRP-gamma polypeptide has a substitution at E54 wherein the substitution is D, K, N, Q or H. In further aspects, the SIRP-gamma polypeptide has a substitution at H56 wherein the substitution is P or R. In additional aspects, the SIRP-gamma polypeptide has a substitution at L66 wherein the substitution is I, V, P, T, A, R, S or G. In further aspects, the SIRP-gamma polypeptide has a substitution at T67 wherein the substitution is I, N, F, S, Y, V, A or D. In additional aspects, the SIRP-gamma polypeptide has a substitution at V92 wherein the substitution is I. In further aspects, the SIRP-gamma polypeptide has a substitution at S98 wherein the substitution is R, N, K, T, I or M. In additional aspects, the SIRP-gamma polypeptide is substituted at N101 wherein the substitution is K, D, E, H or Q. In further aspects, SIRP-gamma polypeptide has the sequence EEELQX$_1$IQPEKLLLVTVGKTATLHCTX$_2$TSX$_3$X$_4$ PX$_5$GPX$_6$X$_7$WFRGX$_8$GPGRX$_9$LIYNX$_{10}$X$_{11}$X$_{12}$GX$_{13}$FP RVTTVSDX$_{14}$X$_{15}$KRNNMDFSIRISSITPADVGTYYCX$_{16}$ KFRKGX$_{17}$PEX$_{18}$VEFKSGPGTEMALGAKPS (SEQ ID NO: 2), wherein X$_1$ is M, I, L or F; X$_2$ is F, I, L or V; X$_3$ is L, I, V, H, N or D; X$_4$ is F, I, L or V; X$_5$ is V, I, L, P, T or A; X$_6$ is V or I; X$_7$ is L or Q; X$_8$ is V or A; X$_9$ is E or V; X$_{10}$ is Q, P, L, V, A or E; X$_{11}$ is K or R; X$_{12}$ is E, D, K, N, Q or H; X$_{13}$ is H, P or R; X$_{14}$ is L, I, V, P, T, A, R, S or G; X$_{15}$ is T, I, N, F, S, Y, V, A or D; X$_{16}$ is V or I; X$_{17}$ is S, R, N, K, T, I or M; and X$_{18}$ is N, K, D, E, H or Q. In additional aspects, the SIRP-gamma polypeptide has the sequence EEELQIIQPEKLLLVTVGKTATLHCTITSLFPVGPVLW-FRGVGPGRVLIYNQRQGPFPRVTTVSDTTKR NNMD-FSIRISSITPADVGTYYCIKFRKGSPENVEFKSGPGTE-MALGAKPS (SEQ ID NO: 3). In additional aspects, the SIRP-gamma polypeptide has the sequence EEELQIIQ-PEKLLLVTVGKTATLHCTITSLFPVGPIQWFRGVG-PGRVLIYNQRDGPFPRVTTVSDGTKR NNMDFSIRIS-SITPADVGTYYCVKFRKGTPEDVEFKSGPGTEMALG-AKPS (SEQ ID NO: 4). In additional aspects, the SIRP-gamma polypeptide has the sequence EEELQIIQPEKLLL-VTVGKTATLHCTITSLFPVGPIQWFRGVGPGRVLIYN-QKDGPFPRVTTVSDGTKR NNMDFSIRISSITPADVGTYYCVKFRKGSPEDVEFKS-GPGTEMALGAKPS (SEQ ID NO: 5). In additional aspects, the SIRP-gamma polypeptide has the sequence EEELQIIQPEKLLLVTVGKTATLHCTITSLFPVG-PIQWFRGVGPGRVLIYNQKDGHFPRVTTVSDGTKR NNMDFSIRISSITPADVGTYYCVKFRKGSPEDVEFKS-GPGTEMALGAKPS (SEQ ID NO: 6). In further aspects, the SIRP-gamma polypeptide has the sequence EEELQIIQ-PEKLLLVTVGKTATLHCTITSLFPVGPIQWFRGAG-PGRVLIYNQRDGPFPRVTTVSDGTKR NNMDFSIRIS-SITPADVGTYYCIKFRKGTPEDVEFKSGPGTEMALG-AKPS (SEQ ID NO: 7). In additional aspects, the SIRP-gamma polypeptide has one of the following sequences:

```
HLib1:
                                                            (SEQ ID NO: 8)
EEELQIIQPEKLLLVTVGKTATLHCTITSHFPVGPIQWFRGVGPGRVLIYNQKDGHFPRVTTVSDGTKR

NNMDFSIRISSITPADVGTYYCVKFRKGSPEDVEFKSGPGTEMALGAKPS;
```

HLib2:
(SEQ ID NO: 9)
EEELQIIQPDKSVLVAAGETATLRCTITSLFPVGPIQWFRGAGPGRVLIYNQRDGPFPRVTTVSDGTKR

NNMDFSIRISSITPADVGTYYCVKFRKGTPEDVEFKSGPGTEMALGAKPS;

HLib3:
(SEQ ID NO: 10)
EEELQIIQPEKLLLVTVGKTATLHCTITSLFPVGPVLWFRGVGPGRVLIYNQRQGPFPRVTTVSDTTKR

NNMDFSIRISSITPADVGTYYCVKFRKGTPEDVEFKSGPGTEMALGAKPS;

HLib4:
(SEQ ID NO: 11)
EEELQIIQPEKLLLVTVGKTATLHCTITSLFPVGPIQWFRGVGPGRELIYNAREGRFPRVTTVSDLTKR

NNMDFSIRISSITPADVGTYYCVKFRKGSPEDVEFKSGPGTEMALGAKPS;

HMLib1:
(SEQ ID NO: 12)
EEELQIIQPDKSVLVAAGETATLRCTITSLFPVGPIQWFRGAGPGRVLIYNQRQGPFPRVTTVSDTTKR

NNMDFSIRIGNITPADAGTYYCIKFRKGSPDDVEFKSGAGTELSVRAKPS;

HMLib2:
(SEQ ID NO: 3)
EEELQIIQPEKLLLVTVGKTATLHCTITSLFPVGPVLWFRGVGPGRVLIYNQRQGPFPRVTTVSDTTKR

NNMDFSIRISSITPADVGTYYCIKFRKGSPENVEFKSGPGTEMALGAKPS;

HMLib3:
(SEQ ID NO: 13)
EEELQIIQPEKLLLVTVGKTATLHCTITSLFPVGPIQWFRGVGPGRVLIYNQREGPFPRVTTVSDGTKR

NNMDFSIRISSITPADVGTYYCVKFRKGSPEDVEFKSGPGTEMALGAKPS;

HMLib4:
(SEQ ID NO: 42)
EEELQMIQPEKLLLVTVGKTATLHCTVTSLLPVGPVLWFRGVGPGRELIYNQKEGHFPRVTTVSDLT

KRNNMDFSIRISSITPADVGTYYCVKFRKGSPENVEFKSGPGTEMALGAKPS;

HMLib5:
(SEQ ID NO: 14)
EEELQIIQPDKSVLVAAGETATLRCTITSLFPVGPIQWFRGAGPGRVLIYNQRDGPFPRVTTVSDGTKR

NNMDFSIRISSITPADVGTYYCIKFRKGIPEDVEFKSGPGTEMALGAKPS;

HMLib6:
(SEQ ID NO: 15)
EEELQIIQPDKSVLVAAGETATLRCTITSLFPVGPIQWFRGAGPGRVLIYNQRDGPFPRVTTVSDGTKR

NNMDFSIRISSITPADVGTYYCIKFRKGIPEDVEFKSGPGTXWH,
wherein X is A, R,
N, D, C, Q, E, G, H, I, L, K, M, F. P, S, T, W, Y, or V;

HMLib7:
(SEQ ID NO: 16)
EEELQIIQPDKSVLVAAGETATLRCTITSLFPVGPIQWFRGAGPGRVLIYNQKDGPFPRVTTVSDGTKR

NNMDFSIRISSITPADVGTYYCIKFRKGTPEDVEFKSGPGTEMALGAKPS;

MLib1:
(SEQ ID NO: 17)
EEELQIIQPEKLLLVTVGKTATLHCTITSLLPVGPIQWFRGVGPGRELIYNQRDGPFPRVTTVSDGTKR

NNMDFSIRISSITPADVGTYYCVKFRKGTPEDVEFKSGPGTEMALGAKPS;

MLib2:
(SEQ ID NO: 18)
EEELQIIQPEKLLLVTVGKTATLHCTLTSLLPVGPILWFRGVGPGRVLIYNQRDGPFPRVTTVSDGTKR

NNMDFSIRISSITPADVGTYYCVKFRKGNPEDVEFKSGPGTEMALGAKPS;

MLib3:
(SEQ ID NO: 19)
EEELQLIQPEKLLLVTVGKTATLHCTITSLFPPGPIQWFRGVGPGRVLIYNQKDGPFPRVTTVSDGTKR

NNMDFSIRISSITPADVGTYYCVKFRKGIPEDVEFKSGPGTEMALGAKPS;

-continued

MLib4:
(SEQ ID NO: 20)
EEELQIIQPEKLLLVTVGKTATLRCTITSLFPVGPIQWFRGAGPGRVLIYNQRDGPFPRVTTVSDGTKR

NNMDFSIRISSITPADVGTYYCIKFRKGIPEDVEFKSGPGTEMALGAKPS;

MLib5:
(SEQ ID NO: 21)
EEELQIIQPEKLLLVTVGKTATLHCTITSLFPIGPILWFRGVGPGRVLIYNQKDGPFPRVTTVSDGTKRN

NMDFSIRISSITPADVGTYYCVKFRKGSPEDVEFKSGPGTEMALGAKPS;

MLib6:
(SEQ ID NO: 22)
EEELQMIQPEKLLLVTVGKTATLHCTITSLFPVGPIQWFRGAGPGRVLIYNQRDGPFPRVTTVSDGTK

RNNMDFSIRISSITPADVGTYYCIKFRKGIPEDVEFKSGPGTEMALGAKPS;

MLib7:
(SEQ ID NO: 23)
EEELQIIQPDKSVLVAAGETATLRCTITSLFPVGPIQWFRGVGPGRVLIYNQKDGPFPRVTTVSDGTKR

NNMDFSIRISSITPADVGTYYCIKFRKGIPEDVEFKSGPGTEMALGAKPS;

MLib8:
(SEQ ID NO: 24)
EEELQIIQPDKSVLVAAGETATLRCTITSLFPVGPIQWFRGAGPGRVLIYNQKDGPFPRVTTVSDGTKR

NNMDFSIRISSITPADVGTYYCIKFRKGTPEDVEFKSGPGTEMALXAKPS;
or

GV1.2:
(SEQ ID NO: 13)
EEELQIIQPEKLLLVTVGKTATLHCTITSLFPVGPIQWFRGVGPGRVLIYNQREGPFPRVTTVSDGTKR

NNMDFSIRISSITPADVGTYYCVKFRKGSPEDVEFKSGPGTEMALGAKPS.

In additional embodiments, the decoy polypeptide comprises a SIRP-beta polypeptide with the sequence EDELQVIQPEKSVSVAAGESATLRCAMTSLIPVGPIM-WFRGAGAGRELIYNQKEGHFPRVTTVSELTK RNN-LDFSISISNITPADAGTYYCVKFRKGSPDDVEFKS-GAGTELSVRAKPS (SEQ ID NO: 25). In particular aspects, the SIRP-beta polypeptide is at least 90% identical to a wildtype SIRP-beta polypeptide. In further aspects, the SIRP-beta polypeptide has an amino acid substitution at I6, I27, F31, Q37, V47, R53, Q54, P56, T66 or I92. In additional aspects, the SIRP-beta polypeptide has a substitution at V6 wherein the substitution is I. In further aspects, the SIRP-beta polypeptide has a substitution at M27 wherein the substitution is I. In further aspects, the SIRP-beta polypeptide has a substitution at I31 wherein the substitution is F. In additional aspects, the SIRP-beta polypeptide has a substitution at M37 wherein the substitution is Q. In further aspects, the SIRP-beta polypeptide has a substitution at E47 wherein the substitution is V. In additional aspects, the SIRP-beta polypeptide has a substitution at K53 wherein the substitution is R. In further aspects, the SIRP-beta polypeptide has a substitution at E54 wherein the substitution is Q. In additional aspects, the SIRP-beta polypeptide has a substitution at H56 wherein the substitution is P. In further aspects, the SIRP-beta polypeptide has a substitution at L66 wherein the substitution is T. In additional aspects, the SIRP-beta polypeptide has a substitution at V92 wherein the substitution is I. In further aspects, the SIRP-beta polypeptide has the sequence EDELQIIQPEKSVSVAAGESATLR-CAITSLFPVGPIQWFRGAGAGRVLIYNQRQGPFPRVT-TVSETTKR NNLDFSISISNITPADAGTYYCIKFRKGSPDDVEFKS-GAGTELSVRAKPS (SEQ ID NO: 26). In further aspects, the SIRP-beta polypeptide has the sequence EDELQX$_1$IQPEKSVSVAAGESATLRCAX$_2$TSLX$_3$PVGP-IX$_4$WFRGAGAGRX$_5$LIYNQX$_6$X$_7$GX$_8$FPRVTTV SEX$_9$TKRNNLDFSISISNITPADAGTYYCX$_{10}$KFRKGS-PDDVEFKSGAGTELSVRAKPS (SEQ ID NO: 45) wherein X$_1$ is V or I; X$_2$ is M or I; X$_3$ is I or F; X$_4$ is M or Q; X$_5$ is E or V; X$_6$ is K or R; X$_7$ is E or Q; X$_8$ is H or P; X$_9$ is L or T; and X$_{10}$ is V or I.

In additional embodiments, the decoy comprises a SIRP-beta2 polypeptide with the sequence EEELQVIQPDKSIS-VAAGESATLHCTVTSLIPVGPIQWFRGAGPGRELIYN-QKEGHFPRVTTVSDLTKR NNMDFSIRISNITPADAGTYYCVKFRKGSPDHVEFKS-GAGTELSVRAKPS (SEQ ID NO: 27). In particular aspects, the SIRP-beta2 polypeptide is at least 90% identical to a wildtype SIRP-beta2 polypeptide. In additional aspects, the SIRP-beta2 polypeptide has an amino acid substitution at I6, I27, F31, V47, R53, Q54, P56, T66, I92 or D101. In additional aspects, the SIRP-beta2 polypeptide is substituted at V6 wherein the substitution is I. In further aspects, the SIRP-beta2 polypeptide is substituted at V27 wherein the substitution is I. In additional aspects, the SIRP-beta2 polypeptide is substituted at I31 wherein the substitution is F. In further aspects, the SIRP-beta2 polypeptide is substituted at E47 wherein the substitution is V. In additional aspects, the SIRP-beta2 polypeptide is substituted at K53 wherein the substitution is R. In further aspects, the SIRP-beta2 polypeptide is substituted at E54 wherein the substitution is Q. In additional aspects, the SIRP-beta2 polypeptide is substituted at H56 wherein the substitution is P. In further aspects, the SIRP-beta2 polypeptide is substituted at L66 wherein the substitution is T. In further aspects, the SIRP-beta2 polypeptide is substituted at V92 wherein the substitution is I. In additional aspects the SIRP-beta2 polypeptide is substituted at H101 wherein the substitution is D. In further aspects, the SIRP-beta 2 polypeptide has the sequence EEELQIIQPDK-SISVAAGESATLHCTITSLFPVGPIQWFRGAGPGRVLI-YNQRQGPFPRVTTVSDTTKRN NMDFSIRISNIT-PADAGTYYCIKFRKGSPDDVEFKSGAGTELSVRAKPS (SEQ ID NO: 28). In further aspects, the SIRP-beta2 polypeptide has the sequence EEELQX$_1$ IQPDKSISVAAGESATLHCTX$_2$TSLX$_3$PVGPIQWFRGA-GPGRX$_4$LIYNQX$_5$X$_6$GX$_7$FPRVTTVSDX$_8$TKRNNMDFSIRISNITPADAGTYYCX$_9$KFRKGSPDX$_{10}$VEFKSGAGTELSVRAKPS (SEQ ID NO: 46) wherein X$_1$ is V or I; X$_2$ is V or I; X$_3$ is I or F; X$_4$ is E or V; X$_5$ is K or R; X$_6$ is E or Q; X$_7$ is H or P; X$_8$ is L or T; X$_9$ is V or I; and X$_{10}$ is H or D.

In additional embodiments, there is provided a decoy polypeptide selected from a SIRP-gamma, SIRP-beta, and SIRP-beta2 polypeptide wherein the SIRP-gamma polypeptide has the sequence EEELQX$_1$IQPEKLLLVTVGKTATLHCTX$_2$TSX$_3$X$_4$PX$_5$-GPX$_6$X$_7$WFRGX$_8$GPGRX$_9$LIYNX$_{10}$X$_{11}$X$_{12}$GX$_{13}$FP RVTTVSDX$_{14}$X$_{15}$KRNNMDFSIRISSITPADVGTYYCX$_{16}$KFRKGX$_{17}$PEX$_{18}$VEFKSGPGTEMALGAKPS (SEQ ID NO: 2), wherein X$_1$ is M, I, L or F; X$_2$ is F, I, L or V; X$_3$ is L, I, V, H, N or D; X$_4$ is F, I, L or V; X$_5$ is V, I, L, P, T or A; X$_6$ is V or I; X$_7$ is L or Q; X$_8$ is V or A; X$_9$ is E or V; X$_{10}$ is Q, P, L, V, A or E; X$_{11}$ is K or R; X$_{12}$ is E, D, K, N, Q or H; X$_{13}$ is H, P or R; X$_{14}$ is L, I, V, P, T, A, R, S or G; X$_{15}$ is T, I, N, F, S, Y, V, A or D; X$_{16}$ is V or I; X$_{17}$ is S, R, N, K, T, I or M; and X$_{18}$ is N, K, D, E, H or Q, wherein the SIRP-beta polypeptide has the sequence the sequence EDELQX$_1$IQPEKSVSVAAGESATLRCAX$_2$TSLX$_3$PVGP-IX$_4$WFRGAGAGRX$_5$LIYNQX$_6$X$_7$GX$_8$FPRVTTV SEX$_9$TKRNNLDFSISISNITPADAGTYYCX$_{10}$KFRKGSP-DDVEFKSGAGTELSVRAKPS (SEQ ID NO: 45) wherein X$_1$ is V or I; X$_2$ is M or I; X$_3$ is I or F; X$_4$ is M or Q; X$_5$ is E or V; X$_6$ is K or R; X$_7$ is E or Q; X$_8$ is H or P; X$_9$ is L or T; and X$_{10}$ is V or I; and wherein the SIRP-beta2 polypeptide has the sequence EEELQX$_1$ IQPDKSISVAAGESATLHCTX$_2$TSLX$_3$PVGPIQWFRGA-GPGRX$_4$LIYNQX$_5$X$_6$GX$_7$FPRVTTVSDX$_8$TKRNNM-DFSIRISNITPADAGTYYCX$_9$KFRKGSPDX$_{10}$VEFKSG-AGTELSVRAKPS (SEQ ID NO: 46) wherein X$_1$ is V or I; X$_2$ is V or I; X$_3$ is I or F; X$_4$ is E or V; X$_5$ is K or R; X$_6$ is E or Q; X$_7$ is H or P; X$_8$ is L or T; X$_9$ is V or I; and X$_{10}$ is H or D.

In additional embodiments, the SIRP-gamma, SIRP-beta or SIRP-beta2 decoy polypeptide blocks binding of CD47 to a ligand. In particular aspects, the ligand is SIRP-alpha, SIRPgamma, or thrombospondin-1.

In additional embodiments, the SIRP-gamma, SIRP-beta or SIRP-beta2 decoy polypeptide binds to a cell. In particular aspects, the cell is a tumor cell, virally infected cell, bacterially infected cell, damaged red blood cell, arterial plaque cell, fibrotic tissue cell, a healthy normal cell such as hematopoietic stem cell, a healthy myeloid or lymphoid precursor cell, or a healthy differentiated hematopoietic cell type such as T, B, plasma, or NK cell.

In additional embodiments the SIRP-gamma, SIRP-beta or SIRP-beta2 decoy polypeptide enables phagocytosis or ADCC of a tumor cell, virally infected cell, bacterially infected cell, damaged red blood cell, arterial plaque cell, fibrotic tissue cell, healthy normal cell such as hematopoietic stem cell, healthy myeloid or lymphoid precursor cell or healthy differentiated hematopoietic cell type such as T, B, plasma, or NK cells.

In additional embodiments, the SIRP-gamma, SIRP-beta or SIRP-beta2 decoy polypeptide is fused to an immunoglobulin Fc sequence. In additional embodiments, the SIRP-gamma, SIRP-beta or SIRP-beta2 polypeptide is multimeric. In additional embodiments, the SIRP-gamma, SIRP-beta or SIRP-beta2 polypeptide is monomeric. In additional embodiments the decoy polypeptide further comprises a detectable label.

In additional embodiments, there is provided a composition comprising the decoy SIRP-gamma, SIRP-beta or SIRP-beta2 polypeptide as described above and a pharmaceutically acceptable carrier or excipient. In particular aspects, the composition further comprises an additional drug. In particular aspects, the drug comprises one or more of a chemotherapeutic agent, kinase inhibitor, proteasome inhibitor, or inhibitor of viral DNA or RNA polymerase. In additional embodiments, the composition further comprises a monoclonal antibody. In particular aspects, the monoclonal antibody binds an antigen on a cancer cell (e.g., myeloma), an immune cell, a pathogen-infected cell, or a hematopoietic stem cell. In additional aspects, the antigen on a cancer cell comprises EGFR, Her2/neu, CD19, CD20, CD22, CD25, CD30, CD33, CD38, CD45, CD47, CD56, CD70, CD117, or EpCAM. In further aspects, the antigen on the immune cell comprises Mlprime, CD2, CD3, CD4, CD5, CD8, CD19, CD20, CD22, CD25, CD38, CD56, PD-1, PD-L1, CTLA4, BTLA, TIM3, LAG3, OX40, GITR or CD137 (4-1BB). In additional aspects, the antigen on a pathogen-infected cell comprises cytomegalovirus (CMV) proteins, including UL-18, UL11, pp65, gB, and pp150. In additional aspects, the antigen on a pathogen-infected cell comprises HIV envelope proteins, including Gp41, Gp120, V1V2 glycan, and V3 glycan, and influenza hemagglutinin. In further aspects, the antigen on the hematopoietic stem cell comprises CD11, CD45, CD117 or Sca1.

In additional embodiments, there is provided a decoy SIRP-gamma, SIRP-beta or SIRP-beta2 polypeptide as described above with increased persistence. In some aspects, increased persistence of the decoy SIRP-gamma, SIRP-beta or SIRP-beta2 polypeptides results in increased cell-surface half-life compared to other SIRP polypeptides.

In additional embodiments, there is provided a decoy SIRP-gamma, SIRP-beta, or SIRP-beta2 polypeptide as described above with increased occupancy or receptor occupancy. In some aspects, increased occupancy of decoy SIRP-gamma, SIRP-beta or SIRP-beta2 polypeptides results in increased binding of the decoy SIRP-gamma, SIRP-beta, or SIRP-beta2 polypeptides to one or more target cells.

In additional embodiments, there is provided an isolated nucleic acid encoding any one of the above decoy polypeptides. In additional embodiments, there is provided a cell expressing any one of the above decoy polypeptides.

In additional embodiments, there is provided a method of modulating phagocytosis or ADCC of a cell expressing CD47, the method comprising contacting the cell with any one of the above decoy polypeptides or the compositions. In additional embodiments, there is provided a method of treating a subject in need thereof comprising administering an effective amount of any one of the above decoy SIRP-gamma, SIRP-beta or SIRP-beta2 polypeptides or compositions. In particular aspects, the subject has cancer, anemia, viral infection, bacterial infection, auto-immune disease, asthma, allergy, transplant rejection, atherosclerosis, or fibrosis.

In additional embodiments, there is provided any one of the above decoy SIRP-gamma, SIRP-beta or SIRP-beta2 polypeptides or compositions for use in treating cancer, viral infection, bacterial infection, auto-immune disease, asthma, allergy, transplant rejection, atherosclerosis, or fibrosis. In additional embodiments there is provided any one of the above decoy SIRP-gamma, SIRP-beta or SIRP-beta2 polypeptides or compositions for use in preconditioning for a hematopoietic stem cell transplant.

In additional embodiments, there is provided a method of visualizing a cell expressing CD47, the method comprising contacting a population of cells with any one of the above decoy polypeptides and a detectable label. In particular aspects, the cell is a tumor cell, virally infected cell, bacterially infected cell, autoreactive T or B cell, damaged red blood cell, arterial plaque cell, fibrotic tissue cell, healthy normal cell such as hematopoietic stem cell, a healthy myeloid or lymphoid precursor cell or healthy differentiated hematopoietic cell type such as T, B, plasma, or NK cell. In additional aspects, the contact is in vivo. In further aspects, the contact is in vitro.

In additional embodiments, there is provided a method of purifying a cell expressing CD47, the method comprising contacting a population of cells with any one of the above decoy polypeptides and a detectable label and purifying cells bound to the detectable label.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE FIGURES

FIGS. 1A and 1B show the surface plasmon resonance-based measurement of binding affinity and kinetics of SIRP-gamma variant GV3 for human CD47. FIG. 1A shows concentrations of the SIRP-gamma variant GV3 used included 100 pM, 316 pM, 1 nM, 3.16 nM, 10 nM, and 100 nM. Using a 1:1 Langmuir binding model, the calculated dissociation constant $K_d$ was 92 pM. The calculated dissociation half-life $T_{1/2}$ was about 44 minutes. FIG. 1B shows a graphic representation of a biotinylated human CD47 bound to the SIRP-gamma variant GV3.

FIGS. 2A and 2B show the surface plasmon resonance-based measurement of binding affinity and kinetics of HAC-GV3, a fusion protein of SIRP-gamma variant GV3 with PD-1 variant HAC, for human CD47. FIG. 2A shows the concentrations of the HAC-GV3 fusion protein used included 100 pM, 316 pM, 1 nM, 3.16 nM, 10 nM, and 100 nM. Using a 1:1 Langmuir binding model, the calculated dissociation constant $K_d$ was 160 pM. The calculated dissociation half-life $T_{1/2}$ was about 40 minutes. FIG. 2B shows a graphic representation of a biotinylated human CD47 bound to the fusion protein comprising SIRP-gamma variant GV3 and HAC.

FIGS. 3A and 3B show the surface plasmon resonance-based measurement of binding affinity and kinetics of HAC-GV3, a fusion protein of SIRP-gamma variant GV3 with PD-1 variant HAC, for human PD-L1. FIG. 3A shows the concentrations of the HAC-GV3 fusion protein used included 100 pM, 316 pM, 1 nM, 3.16 nM, 10 nM, and 100 nM. Using a 1:1 Langmuir binding model, the calculated dissociation constant $K_d$ was 134 pM. The calculated dissociation half-life $T_{1/2}$ was about 38 minutes. FIG. 3B shows a graphic representation of a biotinylated human PD-L1 bound to HAC-GV3.

FIGS. 4A and 4B show the surface plasmon resonance-based measurement of binding affinity and kinetics of simultaneous binding of both human CD47 and human PD-L1 by HAC-GV3. FIG. 4A shows that in comparison to human GV3 alone, the binding curve for fusion protein HAC-GV3 showed a first peak for binding to biotinylated CD47 and a second peak for binding to PD-L1. FIG. 4B shows a graphic representation of a biotinylated human CD47 bound to the GV3 portion of the HAC-GV3 fusion protein, wherein the HAC portion is bound to PD-L1.

FIG. 11A shows receptor occupancy and persistence in total splenic cells. FIG. 11B shows receptor occupancy and persistence in splenocytes. FIG. 11C shows receptor occupancy and persistence in human CD47+ PDL1+ cells. FIG. 11D shows receptor occupancy and persistence in B16-F0 melanoma cells.

DETAILED DESCRIPTION OF THE INVENTION

Figure 5:
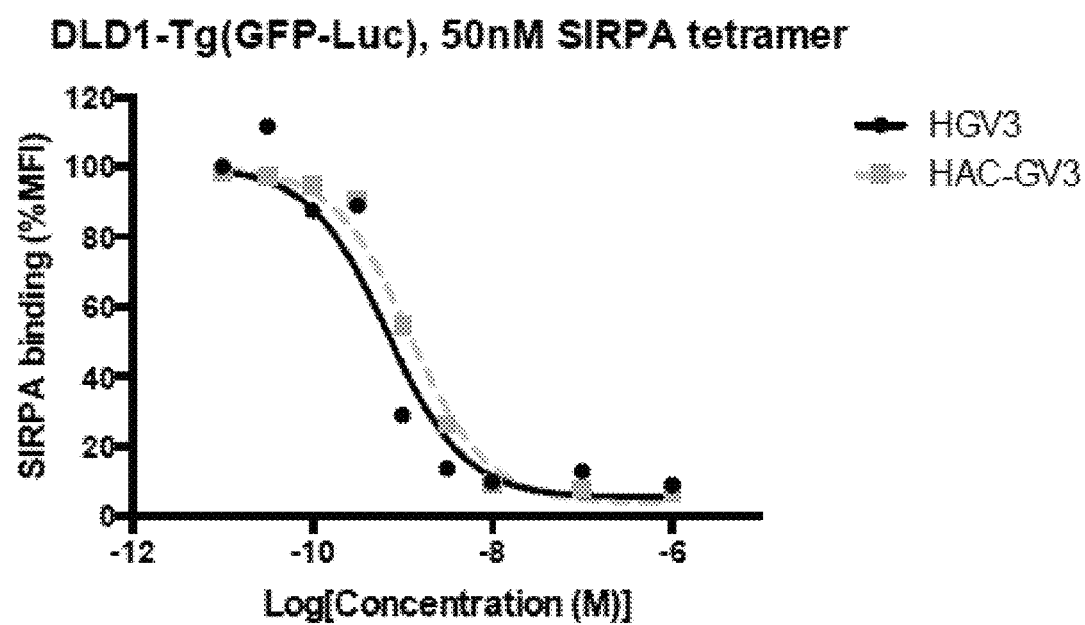
FIG. 5 shows the flow cytometry-based measurement of blockade of CD47/SIRP-alpha interactions on the surface of CD47+ GFP-luciferase+ DLD1-Tg cells by GV3 and HAC-GV3. 50 nM of biotinylated SIRP-alpha tetramers were combined with titrating concentrations of either GV3 or HAC-GV3 in the presence of the CD47+ cells. Percent median fluorescence intensity (% MFI) as a readout of SIRP-alpha binding is plotted against log concentration in M.

SIRP-gamma, SIRP-beta or SIRP-beta2 decoy polypeptides and analogs thereof are provided which may be referred within as decoy polypeptides. The decoy polypeptides are variants of the wildtype human SIRP-gamma, SIRP-beta or SIRP-beta2 proteins. In one embodiment, provided herein is a soluble SIRP-gamma, SIRP-beta or SIRP-beta2 polypeptide, wherein the polypeptide lacks a transmembrane domain and comprises at least one amino acid change relative to the wildtype SIRP-gamma, SIRP-beta or SIRP-beta2 sequence, and wherein the amino acid change increases the affinity of the SIRP-gamma, SIRP-beta or SIRP-beta2 polypeptide binding to CD47, for example by decreasing the off-rate by at least 10-fold, at least 20-fold, at least 50-fold, at least 100-fold, at least 500-fold, or more.

Signal regulatory proteins (SIRPs) constitute a family of cell surface glycoproteins which are expressed on myeloid (including macrophages, granulocytes, myeloid dendritic cells, and mast cells) and neuronal cells. SIRPs constitute a diverse multigene family of immune receptors encompassing inhibitory, activating, nonsignaling and soluble members. CD47, a broadly expressed transmembrane glycoprotein, functions as a cellular ligand for SIRPα and binds to the NH2-terminal extracellular terminus of SIRPα. SIRPα's role has been best documented in respect of its inhibitory role in the phagocytosis of host cells by macrophages and antibody-directed cellular cytotoxicity (ADCC) by neutrophils. In particular, the binding of SIRPα on myeloid cells by CD47 expressed on target cells, generates an inhibitory signal that negatively regulates phagocytosis and ADCC. Agents that bind to either CD47 or to SIRPα and antagonize the CD47:SIRPα interaction act to active macrophage phagocytosis and neutrophil ADCC, particularly towards antibody-opsonized cells (Majeti et al Cell 2009, Chao et al Cell 2010, Zhang et al, Weiskopf et al Science 2013). The agents include monoclonal antibodies, and soluble CD47 and SIRPα receptor "decoys." CD47 is also a ligand for SIRP-gamma, a gene distinct from SIRPα that is expressed on lymphocytes of unclear function. SIRP-beta and SIRP-beta2 are also distinct genes from SIRPα, and despite their similarity in sequence and in structure to SIRPα, they do not naturally bind CD47. However, they can be made to do so through mutation (Hatherly et al, Molecular Cell 2008). In principle, decoy receptors based-off a SIRP-gamma, SIRP-beta, or SIRP-beta2 scaffold could also antagonize the SIRPα-CD47 interaction to increase myeloid cell phagocytosis or ADCC. These decoys would enjoy a major advantage over SIRPα-based decoys as CD47-targeting therapeutics, as the SIRPα ectodomain is highly polymorphic between individuals, thus increasing the likelihood of immunogenicity if the SIRPα was administered as a recombinant therapeutic. By contrast, the ectodomains of SIRP-gamma, SIRP-beta, and SIRP-beta2 are not widely polymorphic, thus avoiding unnecessary immunogenic sequences.

In some embodiments, SIRP-gamma, SIRP-beta or SIRP-beta2 polypeptides described herein stimulate phagocytosis or ADCC by myeloid cells (e.g., macrophages, monocytes, dendritic cells, neutrophils, etc.) to eliminate pathogenic cells (e.g., tumor cells, virally or bacterially infected cells, autoreactive T cells, etc). In some of such embodiments, cells are eliminated selectively, thereby reducing the potential for toxic side effects. In other embodiments, the same polypeptides could be used to enhance the elimination of endogenous cells for therapeutic effect, such as B or T lymphocytes in autoimmune disease, asthma, and allergy, or hematopoietic stem cells (HSCs) for stem cell transplantation.

In some embodiments, SIRP-gamma, SIRP-beta or SIRP-beta2 polypeptides described herein have increased occupancy or receptor occupancy compared to other SIRP polypeptides known in the art. In some embodiments, SIRP-gamma, SIRP-beta or SIRP-beta2 polypeptides described herein have increased persistence compared to other SIRP polypeptides known in the art. Occupancy or receptor occupancy, as used herein, refers to binding to a target cell, target receptor, target protein, or target tissue. Persistence, as used herein, refers to both serum half-life or cell binding half-life of the polypeptides when administered to an individual, subject, or patient.

SIRP Polypeptides and SIRP Polypeptide Variants

The signal regulatory proteins (SIRP, CD172) are a family of membrane proteins involved in leukocyte function. The SIRP protein family includes Signal-Regulatory protein Gamma (SIRP-gamma, CD172g), Signal Regulatory Protein Beta (SIRP-beta, Signal Regulatory Protein Beta 1, CD172b, SIRP-beta1) and Signal Regulatory Protein Beta 2 (SIRP-beta2, PTPN1L).

The amino acid sequence of human SIRP-gamma is available in the SWISS-PROT database as Q9P1W8. SIRP-gamma includes three isoforms. The amino acid sequence of human SIRP-beta is available in the SWISS-PROT database as O00241 and Q5TFQ8. SIRP-beta includes three isoforms. The amino acid sequence of SIRP-beta2 is available in the SWISS-PROT database as Q5JXA9. SIRP-beta2 includes three isoforms.

Contemplated within the scope of embodiments presented herein are variants of the SIRP-gamma, SIRP-beta and SIRP-beta2 polypeptides that act as decoys for CD47 and activate phagocytosis. In some embodiments, a decoy polypeptide comprises a SIRP-gamma, a SIRP-beta or a SIRP-beta2 polypeptide, wherein the polypeptide comprises at least one amino acid modification to increase affinity of the decoy SIRP-gamma, SIRP-beta and SIRP-beta2 polypeptide binding to CD47 as compared to the affinity for CD47 of the corresponding wild type SIRP-gamma, SIRP-beta and SIRP-beta2 polypeptide.

As used herein, "sequence substantially identical to a wildtype SIRP-gamma, SIRP-beta or SIRP-beta2 polypeptide sequence" means that, in one embodiment, a sequence is at least 80% identical to a wildtype SIRP-gamma, SIRP-beta or SIRP-beta2 polypeptide sequence. In other embodiments, "sequence substantially identical to a wildtype SIRP-gamma, SIRP-beta or SIRP-beta2 polypeptide sequence" means that, a sequence is at least 85% identical to a wildtype SIRP-gamma, SIRP-beta or SIRP-beta2 polypeptide sequence. In other embodiments, "sequence substantially identical to a wildtype SIRP-gamma, SIRP-beta or SIRP-beta2 polypeptide sequence" means that, a sequence is at least 90% identical to a wildtype SIRP-gamma, SIRP-beta or SIRP-beta2 polypeptide sequence. In other embodiments, "sequence substantially identical to a wildtype SIRP-gamma, SIRP-beta or SIRP-beta2 polypeptide sequence" means that, a sequence is at least 95% identical to a wildtype SIRP-gamma, SIRP-beta or SIRP-beta2 polypeptide sequence.

In some embodiments, the decoy polypeptides described herein incorporate high affinity homologues or variants of SIRP-gamma, SIRP-beta or SIRP-beta2 polypeptides (e.g., variants of SIRP-gamma, SIRP-beta or SIRP-beta2). Accordingly, the embodiments presented herein encompass the use of a SIRP-gamma, SIRP-beta or SIRP-beta2 polypeptide having a sequence that is similar to, but not identical to, the amino acid sequence of wildtype SIRP-gamma, SIRP-beta or SIRP-beta2 polypeptide. Thus, also contemplated within the scope of embodiments provided herein is the use of a SIRP-gamma, SIRP-beta or SIRP-beta2 polypeptide that has a sequence identity of 99%, 98%, 97%, 96%, 95%, 94%, 93%, 92%, 91%, 90%, 89%, 88%, 87%, 86%, 85%, 84%, 83%, 82%, 81%, or 80% compared to the sequence of wildtype SIRP-gamma, SIRP-beta or SIRP-beta2 polypeptide, and which binds with high affinity to CD47.

In some embodiments, a SIRP-gamma, SIRP-beta or SIRP-beta2 polypeptide variant is modified to contain conservative variations so as to change non-critical residues or residues in non-critical regions. Amino acids that are not critical are identified by known methods, such as site-directed mutagenesis, crystallization, nuclear magnetic resonance, photoaffinity labeling, or alanine-scanning mutagenesis (Cunningham et al., Science, 244:1081-1085 (1989); Smith et al., J. Mol. Biol., 224:899-904 (1992); de Vos et al., Science, 255:306-312 (1992)). Modified proteins are tested for activity or ability to bind to CD47 via methods such as in vitro activity or in vivo activity.

In some embodiments, a SIRP-gamma, SIRP-beta or SIRP-beta2 polypeptide variant incorporates 1, 2, 3, 4, 5 or more amino acid substitutions that improve SIRP-gamma, SIRP-beta or SIRP-beta2 polypeptide stability or with a different hydrophobic amino acid that improves SIRP-gamma, SIRP-beta or SIRP-beta2 polypeptide stability against oxidation, or with a different amino acid that improves SIRP-gamma, SIRP-beta or SIRP-beta2 polypeptide against protease. Thus, a "variant" SIRP-gamma, SIRP-beta or SIRP-beta2 polypeptide differs in amino acid sequence from the sequence represented by a wildtype SIRP-gamma, SIRP-beta or SIRP-beta2 polypeptide by one or more substitutions, deletions, insertions, inversions, truncations, modifications, or a combination thereof. Such a variant optionally contains amino acid substitutions that substitute a given amino acid with another amino acid of similar characteristics. Conservative substitutions include, among the aliphatic amino acids, interchange of alanine, valine, leucine, and isoleucine; interchange of the hydroxyl residues serine and threonine, exchange of the acidic residues aspartate and glutamate, substitution between the amide residues asparagine and glutamine, exchange of the basic residues lysine and arginine, and replacements among the aromatic residues phenylalanine and tyrosine. See Bowie et al., Science, 247:1306-1310 (1990).

The SIRP-gamma, SIRP-beta or SIRP-beta2 polypeptide is a variant, as described in detail below, in ways in which the variant retains or improves the characteristic of CD47 binding.

In some embodiments, a SIRP-gamma, SIRP-beta or SIRP-beta2 polypeptide variant is a fragment of the SIRP-gamma, SIRP-beta or SIRP-beta2 protein. In some embodiments, SIRP-gamma, SIRP-beta or SIRP-beta2 polypeptide variants include proteolytic cleavage-resistant SIRP-gamma, SIRP-beta or SIRP-beta2 polypeptide fragments or SIRP-gamma, SIRP-beta or SIRP-beta2 polypeptide fragments containing one or more non-natural amino acids, such as D-amino acids. Such derivatives would have the benefit of increased circulating half-life, while retaining the beneficial characteristic of CD47 binding.

In another embodiment, a SIRP-gamma, SIRP-beta or SIRP-beta2 polypeptide variant comprises a decoy polypeptide. In certain embodiments, the decoy polypeptide comprises a SIRP-gamma polypeptide with the sequence EEELQMIQPEKLLLVTVGKTATLHCTVTSLLPVGPVL-WFRGVGPGRELIYNQKEGHFPRVTTVSDLT KRNN-MDFSIRISSITPADVGTYYCVKFRKGSPENVEFKS-GPGTEMALGAKPS (SEQ ID NO: 1), or a polypeptide substantially identical to a wildtype SIRP-gamma sequence. In particular aspects, the SIRP-gamma polypeptide has at least one, two, three, four, five, six, seven, eight, nine, ten, eleven, twelve, thirteen, fourteen, fifteen, sixteen, seventeen or eighteen amino acid substitutions at M6, V27, L30, L31, V33, V36, L37, V42, E47, Q52, K53, E54, H56, L66, T67, V92, S98 or N101. In further aspects, the SIRP-gamma polypeptide has a substitution at M6 wherein the substitution is I, L or F. In additional aspects, the SIRP-gamma polypeptide has a substitution at V27 wherein the substitution is F, I or L. In further aspects, the SIRP-gamma polypeptide has a substitution at L30 wherein the substitution is I, V, H, N or D. In additional aspects, the SIRP-gamma polypeptide has a substitution at L31 wherein the substitution is F, I or V. In further aspects, the SIRP-gamma polypeptide has a substitution at V33 wherein the substitution is I, L, P, T or A. In additional aspects, the SIRP-gamma polypeptide has a substitution at V36 wherein the substitution is I. In additional aspects, the SIRP-gamma polypeptide has a substitution at L37 wherein the substitution is Q. In additional aspects, the SIRP-gamma polypeptide has a substitution at V42 wherein the substitution is A. In further aspects, the SIRP-gamma polypeptide has a substitution at E47 wherein the substitution is V. In additional aspects, the SIRP-gamma polypeptide has a substitution at Q52 wherein the substitution is P, L, V, A or E. In additional aspects the SIRP-gamma polypeptide has a substitution at K53 wherein the substitution is R. In further aspects, the SIRP-gamma polypeptide has a substitution at E54 wherein the substitution is D, K, N, Q or H. In further aspects, the SIRP-gamma polypeptide has a substitution at H56 wherein the substitution is P or R. In additional aspects, the SIRP-gamma polypeptide has a substitution at L66 wherein the substitution is I, V, P, T, A, R, S or G. In further aspects, the SIRP-gamma polypeptide has a substitution at T67 wherein the substitution is I, N, F, S, Y, V, A or D. In further aspects, the SIRP-gamma polypeptide has a substitution at V92 wherein the substitution is I. In additional aspects, the SIRP-gamma polypeptide has a substitution at S98 wherein the substitution is R, N, K, T, I or M. In further aspects, the SIRP-gamma polypeptide is substituted at N101 wherein the substitution is K, D, E, H or Q. In additional aspects, the SIRP-gamma polypeptide has the sequence EEELQX$_1$IQPEKLLLVTVGKTATLHCTX$_2$TSX$_3$X$_4$PX$_5$GPX$_6$X$_7$W-FRGX$_8$GPGRX$_9$LIYNX$_{10}$X$_{11}$X$_{12}$GX$_{13}$FPRVTTVSDX$_{14}$X$_{15}$KRNNMDFSIRISSITPADVGTYYCX$_{16}$KFRKGX$_{17}$PEX$_{18}$VEFKSGPGTEMALGAKPS (SEQ ID NO: 2), wherein X$_1$ is M, I, L or F; X$_2$ is F, I, L or V; X$_3$ is L, I, V, H, N or D; X$_4$ is F, I, L or V; X$_5$ is V, I, L, P, T or A; X$_6$ is V or I; X$_7$ is L or Q; X$_8$ is V or A; X$_9$ is E or V; X$_{10}$ is Q, P, L, V, A or E; X$_{11}$ is K or R; X$_{12}$ is E, D, K, N, Q or H; X$_{13}$ is H, P or R; X$_{14}$ is L, I, V, P, T, A, R, S or G; X$_{15}$ is T, I, N, F, S, Y, V, A or D; X$_{16}$ is V or I; X$_{17}$ is S, R, N, K, T, I or M; and $X_{18}$ is N, K, D, E, H or Q. In additional aspects the decoy polypeptide has the sequence EEELQIIQPEKLLLVTVGKTATLHCTITSLFPVGPVLWFRGVGPGRVLIYNQRQGPFPRVTTVSDTTKR NNMDFSIRISSITPADVGTYYCIKFRKGSPENVEFKSGPGTEMALGAKPS (SEQ ID NO: 3). In further aspects, the SIRP-gamma polypeptide has the sequence EEELQIIQPEKLLLVTVGKTATLHCTITSLFPVGPIQWFRGVGPGRVLIYNQRDGPFPRVTTVSDGTKR NNMDFSIRISSITPADVGTYYCVKFRKGTPEDVEFKSGPGTEMALGAKPS (SEQ ID NO: 4). In additional aspects, the SIRP-gamma polypeptide has the sequence EEELQIIQPEKLLLVTVGKTATLHCTITSLFPVGPIQWFRGVGPGRVLIYNQKDGPFPRVTTVSDGTKR NNMDFSIRISSITPADVGTYYCVKFRKGSPEDVEFKSGPGTEMALGAKPS (SEQ ID NO: 5). In additional aspects, the SIRP-gamma polypeptide has the sequence EEELQIIQPEKLLLVTVGKTATLHCTITSLFPVGPIQWFRGVGPGRVLIYNQKDGHFPRVTTVSDGTKR NNMDFSIRISSITPADVGTYYCVKFRKGSPEDVEFKSGPGTEMALGAKPS (SEQ ID NO: 6). In further aspects, the SIRP-gamma polypeptide has the sequence EEELQIIQPEKLLLVTVGKTATLHCTITSLFPVGPIQWFRGAGPGRVLIYNQRDGPFPRVTTVSDGTKR NNMDFSIRISSITPADVGTYYCIKFRKGTPEDVEFKSGPGTEMALGAKPS (SEQ ID NO: 7). In additional aspects, the SIRP-gamma polypeptide has one of the following sequences:

```
HLib1:
                                                      (SEQ ID NO: 8)
EEELQIIQPEKLLLVTVGKTATLHCTITSHFPVGPIQWFRGVGPGRVLIYNQKDGHFPRVTTVSDGTKR

NNMDFSIRISSITPADVGTYYCVKFRKGSPEDVEFKSGPGTEMALGAKPS;

HLib2:
                                                      (SEQ ID NO: 9)
EEELQIIQPDKSVLVAAGETATLRCTITSLFPVGPIQWFRGAGPGRVLIYNQRDGPFPRVTTVSDGTKR

NNMDFSIRISSITPADVGTYYCVKFRKGTPEDVEFKSGPGTEMALGAKPS;

HLib3:
                                                      (SEQ ID NO: 10)
EEELQIIQPEKLLLVTVGKTATLHCTITSLFPVGPVLWFRGVGPGRVLIYNQRQGPFPRVTTVSDTTKR

NNMDFSIRISSITPADVGTYYCVKFRKGTPEDVEFKSGPGTEMALGAKPS;

HLib4:
                                                      (SEQ ID NO: 11)
EEELQIIQPEKLLLVTVGKTATLHCTITSLFPVGPIQWFRGVGPGRELIYNAREGRFPRVTTVSDLTKR

NNMDFSIRISSITPADVGTYYCVKFRKGSPEDVEFKSGPGTEMALGAKPS;

HMLib1:
                                                      (SEQ ID NO: 12)
EEELQIIQPDKSVLVAAGETATLRCTITSLFPVGPIQWFRGAGPGRVLIYNQRQGPFPRVTTVSDTTKR

NNMDFSIRIGNITPADAGTYYCIKFRKGSPDDVEFKSGAGTELSVRAKPS;

HMLib2:
                                                      (SEQ ID NO: 3)
EEELQIIQPEKLLLVTVGKTATLHCTITSLFPVGPVLWFRGVGPGRVLIYNQRQGPFPRVTTVSDTTKR

NNMDFSIRISSITPADVGTYYCIKFRKGSPENVEFKSGPGTEMALGAKPS;

HMLib3:
                                                      (SEQ ID NO: 13)
EEELQIIQPEKLLLVTVGKTATLHCTITSLFPVGPIQWFRGVGPGRVLIYNQREGPFPRVTTVSDGTKR

NNMDFSIRISSITPADVGTYYCVKFRKGSPEDVEFKSGPGTEMALGAKPS;

HMLib4:
                                                      (SEQ ID NO: 42)
EEELQMIQPEKLLLVTVGKTATLHCTVTSLLPVGPVLWFRGVGPGRELIYNQKEGHFPRVTTVSDLT

KRNNMDFSIRISSITPADVGTYYCVKFRKGSPENVEFKSGPGTEMALGAKPS;

HMLib5:
                                                      (SEQ ID NO: 14)
EEELQIIQPDKSVLVAAGETATLRCTITSLFPVGPIQWFRGAGPGRVLIYNQRDGPFPRVTTVSDGTKR

NNMDFSIRISSITPADVGTYYCIKFRKGIPEDVEFKSGPGTEMALGAKPS;

HMLib6:
                                                      (SEQ ID NO: 15)
EEELQIIQPDKSVLVAAGETATLRCTITSLFPVGPIQWFRGAGPGRVLIYNQRDGPFPRVTTVSDGTKR

NNMDFSIRISSITPADVGTYYCIKFRKGIPEDVEFKSGPGTXWH,
wherein X is A, R, N, D, C, Q, E, G, H, I, L, K, M, F, P, S, T,
 W, Y, or V;
```

```
HMLib7:
                                              (SEQ ID NO: 16)
EEELQIIQPDKSVLVAAGETATLRCTITSLFPVGPIQWFRGAGPGRVLIYNQKDGPFPRVTTVSDGTKR

NNMDFSIRISSITPADVGTYYCIKFRKGTPEDVEFKSGPGTEMALGAKPS;

MLib1:
                                              (SEQ ID NO: 17)
EEELQIIQPEKLLLVTVGKTATLHCTITSLLPVGPIQWFRGVGPGRELIYNQRDGPFPRVTTVSDGTKR

NNMDFSIRISSITPADVGTYYCVKFRKGTPEDVEFKSGPGTEMALGAKPS;

MLib2:
                                              (SEQ ID NO: 18)
EEELQIIQPEKLLLVTVGKTATLHCTLTSLLPVGPILWFRGVGPGRVLIYNQRDGPFPRVTTVSDGTKR

NNMDFSIRISSITPADVGTYYCVKFRKGNPEDVEFKSGPGTEMALGAKPS;

MLib3:
                                              (SEQ ID NO: 19)
EEELQLIQPEKLLLVTVGKTATLHCTITSLFPPGPIQWFRGVGPGRVLIYNQKDGPFPRVTTVSDGTKR

NNMDFSIRISSITPADVGTYYCVKFRKGIPEDVEFKSGPGTEMALGAKPS;

MLib4:
                                              (SEQ ID NO: 20)
EEELQIIQPEKLLLVTVGKTATLRCTITSLFPVGPIQWFRGAGPGRVLIYNQRDGPFPRVTTVSDGTKR

NNMDFSIRISSITPADVGTYYCIKFRKGIPEDVEFKSGPGTEMALGAKPS;

MLib5:
                                              (SEQ ID NO: 21)
EEELQIIQPEKLLLVTVGKTATLHCTITSLFPIGPILWFRGVGPGRVLIYNQKDGPFPRVTTVSDGTKRN

NMDFSIRISSITPADVGTYYCVKFRKGSPEDVEFKSGPGTEMALGAKPS;

MLib6:
                                              (SEQ ID NO: 22)
EEELQMIQPEKLLLVTVGKTATLHCTITSLFPVGPIQWFRGAGPGRVLIYNQRDGPFPRVTTVSDGTK

RNNMDFSIRISSITPADVGTYYCIKFRKGIPEDVEFKSGPGTEMALGAKPS;

MLib7:
                                              (SEQ ID NO: 23)
EEELQIIQPDKSVLVAAGETATLRCTITSLFPVGPIQWFRGVGPGRVLIYNQKDGPFPRVTTVSDGTKR

NNMDFSIRISSITPADVGTYYCIKFRKGIPEDVEFKSGPGTEMALGAKPS;

MLib8:
                                              (SEQ ID NO: 24)
EEELQIIQPDKSVLVAAGETATLRCTITSLFPVGPIQWFRGAGPGRVLIYNQKDGPFPRVTTVSDGTKR

NNMDFSIRISSITPADVGTYYCIKFRKGTPEDVEFKSGPGTEMALXAKPS;
or

GV1.2:
                                              (SEQ ID NO: 13)
EEELQIIQPEKLLLVTVGKTATLHCTITSLFPVGPIQWFRGVGPGRVLIYNQREGPFPRVTTVSDGTKR

NNMDFSIRISSITPADVGTYYCVKFRKGSPEDVEFKSGPGTEMALGAKPS.
```

In additional embodiments the decoy polypeptide comprises a SIRP-beta polypeptide with the sequence EDELQVIQPEKSVSVAAGESATLRCAMTSLIPVGPIM-WFRGAGAGRELIYNQKEGHFPRVTTVSELTK RNN-LDFSISISNITPADAGTYYCVKFRKGSPDDVEFKS-GAGTELSVRAKPS (SEQ ID NO: 25). In particular aspects, the SIRP-beta polypeptide is at least 90% identical to a wildtype SIRP-beta polypeptide. In additional aspects, the SIRP-beta polypeptide has amino acid substitutions at V6, M27, I31, M37, E47, K53, E54, H56, L66 or V92. In further aspects, the SIRP-beta polypeptide has a substitution at V6 wherein the substitution is I. In additional aspects, the SIRP-beta polypeptide has a substitution at M27 wherein the substitution is I. In further aspects, the SIRP-beta polypeptide has a substitution at I31 wherein the substitution is F. In additional aspects, the SIRP-beta polypeptide has a substitution at M37 wherein the substitution is Q. In further aspects, the SIRP-beta polypeptide has a substitution at E47 wherein the substitution is V. In additional aspects, the SIRP-beta polypeptide has a substitution at K53 wherein the substitution is R. In further aspects, the SIRP-beta polypeptide has a substitution at E54 wherein the substitution is Q. In additional aspects, the SIRP-beta polypeptide has a substitution at H56 wherein the substitution is P. In further aspects, the SIRP-beta polypeptide has a substitution at L66 wherein the substitution is T. In additional aspects, the SIRP-beta polypeptide has a substitution at V92 wherein the substitution is I. In further aspects, the SIRP-beta polypeptide has the sequence EDELQIIQPEKSVSVAAGESATLR-CAITSLFPVGPIQWFRGAGAGRVLIYNQRQGPFPRVT- TVSETTKR NNLDFSISISNITPADAGTYYCIKFRKGSPDDVEFKSGAGTELSVRAKPS (SEQ ID NO: 26). In further aspects, the SIRP-beta polypeptide has the sequence EDELQX$_1$IQPEKSVSVAAGESATLRCAX$_2$TSLX$_3$PVGPIX$_4$WFRGAGAGRX$_5$LIYNQX$_6$X$_7$GX$_8$FPRVTTV SEX$_9$TKRNNLDFSISISNITPADAGTYYCX$_{10}$KFRKGSPDDVEFKSGAGTELSVRAKPS (SEQ ID NO: 45) wherein X$_1$ is V or I; X$_2$ is M or I; X$_3$ is I or F; X$_4$ is M or Q; X$_5$ is E or V; X$_6$ is K or R; X$_7$ is E or Q; X$_8$ is H or P; X$_9$ is L or T; and X$_{10}$ is V or I.

In further embodiments, the decoy polypeptide comprises a SIRP-beta2 polypeptide with the sequence EEELQVIQPDKSISVAAGESATLHCTVTSLIPVGPIQWFRGAGPGRELIYNQKEGHFPRVTTVSDLTKR NNMDFSIRISNITPADAGTYYCVKFRKGSPDHVEFKSGAGTELSVRAKPS (SEQ ID NO: 27). In particular aspects, the SIRP-beta2 polypeptide is at least 90% identical to a wildtype SIRP-beta2 polypeptide. In additional aspects, the SIRP-beta2 polypeptide has amino acid substitutions at V6, V27, I31, E47, K53, E54, H56, L66, V92 or H101. In further aspects, the SIRP-beta2 polypeptide is substituted at V6 wherein the substitution is I. In additional aspects, the SIRP-beta2 polypeptide is substituted at V27 wherein the substitution is I. In further aspects, the SIRP-beta2 polypeptide is substituted at I31 wherein the substitution is F. In additional aspects, the SIRP-beta2 polypeptide is substituted at E47 wherein the substitution is V. In further aspects, the SIRP-beta2 polypeptide is substituted at K53 wherein the substitution is R. In additional aspects, the SIRP-beta2 polypeptide is substituted at E54 wherein the substitution is Q. In further aspects, the SIRP-beta2 polypeptide is substituted at H56 wherein the substitution is P. In additional aspects, the SIRP-beta2 polypeptide is substituted at L66 wherein the substitution is T. In further aspects, the SIRP-beta2 polypeptide is substituted at V92 wherein the substitution is I. In additional aspects, the SIRP-beta2 polypeptide is substituted at H101 wherein the substitution is D. In further aspects, the SIRP-beta 2 polypeptide has the sequence EEELQIIQPDKSISVAAGESATLHCTITSLFPVGPIQWFRGAGPGRVLIYNQRQGPFPRVTTVSDTTKRN NMDFSIRISNITPADAGTYYCIKFRKGSPDDVEFKSGAGTELSVRAKPS (SEQ ID NO: 28). In further aspects, the SIRP-beta2 polypeptide has the sequence EEELQX$_1$IQPDKSISVAAGESATLHCTX$_2$TSLX$_3$PVGPIQWFRGAGPGRX$_4$LIYNQX$_5$X$_6$GX$_7$FPRVTTVSDX$_8$TKRNNMDFSIRISNITPADAGTYYCX$_9$KFRKGSPDX$_{10}$VEFKSGAGTELSVRAKPS (SEQ ID NO: 46) wherein X$_1$ is V or I; X$_2$ is V or I; X$_3$ is I or F; X$_4$ is E or V; X$_5$ is K or R; X$_6$ is E or Q; X$_7$ is H or P; X$_8$ is L or T; X$_9$ is V or I; and X$_{10}$ is H or D.

In some embodiments, the decoy polypeptide blocks binding of CD47 to a binding partner or ligand. In particular aspects, the binding partner or ligand comprises one or more of SIRPalpha (SIRPA), SIRPgamma (SIRPG), or thrombospondin-1 (TSP-1, THBS1).

In some embodiments, the decoy polypeptide binds to a cell. In particular aspects, binding of the decoy polypeptide to the cell, activates, enables, induces, or causes phagocytosis of the cell by a phagocyte, such as a professional phagocyte (e.g. monocytes, macrophages, neutrophils, dendritic cells or mast cells), a non-professional phagocyte (e.g. epithelial cells, endothelial cells, fibroblasts or mesenchymal cells) or both. In additional aspects, the cell is a tumor cell, virally infected cell, bacterially infected cell, self-reactive cell, such as a self-reactive T cell or B cell, or other undesirable or pathogenic cells or tissues in the body, such as damaged red blood cells, arterial plaques, or fibrotic tissue. In additional aspects, the cell is a healthy normal cell such as hematopoietic stem cell, a healthy myeloid or lymphoid precursor cell, or a healthy differentiated hematopoietic cell type such as T, B, plasma, or NK cells.

In some embodiments, the decoy polypeptide is a chimera or a fusion protein. In particular aspects, the decoy polypeptide is fused to an immunoglobulin Fc sequence, a green fluorescent protein, a red fluorescent protein, a biotin, a HIS tag, a MYC tag, a FLAG, or other polypeptide sequence. In some embodiments, the decoy polypeptide is fused to a wild type subunit of PD-1 (PDCD1), PD-L1 (CD274), PD-L2 (PDCD1LG2), CTLA4, TIM3 (HAVCR2), CEACAM1, LAG3, BTLA, TNFRSF14, TIGIT, PVR, LIGHT, IL2, IL12A, IL15, IL10, LILRB1, LILRB2, LILRB3, LILRB4, LILRB5, LILRA1, LILRA2, LILRA3, LILRA4, LILRA5, LILRA6, CD40, CD40L, OX40, OX40L, CD137 (4-1BB, TNFRSF9), TNFSF9 (4-1BBL), B7-H4 (VCTN1), SIRPA, CD47, CD33, CD44, C5, C3, or other proteins. In some embodiments, the decoy polypeptide is fused to an subunit that is a variant of PD-1 (PDCD1), PD-L1 (CD274), PD-L2 (PDCD1LG2), CTLA4, TIM3 (HAVCR2), CEACAM1, LAG3, BTLA, TNFRSF14, TIGIT, PVR, LIGHT, IL2, IL12A, IL15, IL10, LILRB1, LILRB2, LILRB3, LILRB4, LILRB5, LILRA1, LILRA2, LILRA3, LILRA4, LILRA5, LILRA6, CD40, CD40L, OX40, OX40L, CD137 (4-1BB, TNFRSF9), TNFSF9 (4-1BBL), B7-H4 (VCTN1), SIRPA, CD47, CD33, CD44, C5, C3, or other immune regulatory proteins, engineered for high affinity binding to their respective ligands. In some embodiments, the decoy polypeptide is fused to an subunit that is a variant of PD-1 (PDCD1), PD-L1 (CD274), PD-L2 (PDCD1LG2), CTLA4, TIM3 (HAVCR2), CEACAM1, LAG3, BTLA, TNFRSF14, TIGIT, PVR, LIGHT, IL2, IL12A, IL15, IL10, LILRB1, LILRB2, LILRB3, LILRB4, LILRB5, LILRA1, LILRA2, LILRA3, LILRA4, LILRA5, LILRA6, CD40, CD40L, OX40, OX40L, CD137 (4-1BB, TNFRSF9), TNFSF9 (4-1BBL), B7-H4 (VCTN1), SIRPA, CD47, CD33, CD44, C5, C3, or other proteins, engineered for reduced affinity binding to their respective ligands. In some embodiments, the decoy polypeptide is fused to an subunit that is a variant of PD-1 (PDCD1), PD-L1 (CD274), PD-L2 (PDCD1LG2), CTLA4, TIM3 (HAVCR2), CEACAM1, LAG3, BTLA, TNFRSF14, TIGIT, PVR, LIGHT, IL2, IL12A, IL15, IL10, LILRB1, LILRB2, LILRB3, LILRB4, LILRB5, LILRA1, LILRA2, LILRA3, LILRA4, LILRA5, LILRA6, CD40, CD40L, OX40, OX40L, CD137 (4-1BB, TNFRSF9), TNFSF9 (4-1BBL), B7-H4 (VCTN1), SIRPA, CD47, CD33, CD44, C5, C3, or other proteins, engineered for altered binding affinity to additional ligands besides their natural ligands. In additional aspects, the decoy polypeptide is fused to or administered in combination with a monoclonal antibody such as an anti-CD20 antibody, an anti-EGFR antibody, an anti-Her2/Neu (ERBB2) antibody, an anti-EPCAM antibody, an anti-GL2 antibody, anti-GD2, anti-GD3, anti-CD2, anti-CD3, anti-CD4, anti-CD8, anti-CD19, anti-CD22, anti-CD30, anti-CD33, anti-CD45, anti-CD47, anti-CD52, anti-CD56, anti-CD70, anti-CD117, an anti-SIRPA antibody, an anti-CD47 antibody, an anti-LILRB1 antibody, an anti-PD-1 antibody, an anti-PD-L1 antibody, an anti-PD-L2 antibody, or any antibody designed to bind to a tumor cell, a virally- or bacterially-infected cell, immune cell, or healthy normal cell, or to a cytokine, chemokine, or hormone of any kind.

In some embodiments decoy polypeptide comprises a SIRP-gamma, SIRP-beta or SIRP-beta2 polypeptide in multimeric form. In particular aspects, the decoy polypeptide comprises a dimer, a trimer, a tetramer, a pentamer or other multimer. In other embodiments, the decoy polypeptide comprises a SIRP-gamma, SIRP-beta or SIRP-beta2 polypeptide in monomeric form.

In some embodiments, the decoy polypeptide comprises a detectable label. In particular aspects, the detectable label comprises an enzymatic label such as horseradish peroxidase (HRP), alkaline phosphatase (AP) or glucose oxidase. In additional aspects, the detectable label comprises a fluorescent label such as Alexa Fluor® 350, Alexa Fluor® 405, Alexa Fluor® 488, Alexa Fluor® 532, Alexa Fluor® 546, Alexa Fluor® 555, Alexa Fluor® 568, Alexa Fluor® 594, Alexa Fluor® 647, Alexa Fluor® 680, Alexa Fluor® 750, BODIPY® FL, Coumarin, Cy®3, Cy®5, Fluorescein (FITC), Oregon Green®, Pacific Blue™, Pacific Green™, Pacific Orange™, Tetramethylrhodamine (TRITC), Texas Red® or other fluorescent label. In further aspects, the detectable label comprises a chelating group, such as Cyclen, Cyclam, DO2A, DOTP, DOTMA, TETA, DOTAM, CB-T2A, DOTA or NOTA. In further aspects, the detectable label comprises a radioactive isotope such as $^{32}$P, $^{33}$P, $^{3}$H, $^{14}$C, $^{125}$I, $^{18}$F, $^{68}$Ga, $^{64}$Cu, $^{89}$Zr, $^{11}$C, $^{13}$N, $^{15}$O, $^{62}$Cu, $^{124}$I, $^{76}$Br, $^{82}$Rb or other radioactive isotope.

In additional embodiments, the decoy polypeptide is a fusion or chimeric polypeptide. In additional embodiments, the decoy polypeptide comprises a SIRP-gamma polypeptide sequence fused to a polypeptide sequence comprising an immune checkpoint inhibitor, a co-stimulatory molecule, or a cytokine or an attenuated cytokine, wherein the sequences are connected by a Gly-Ser linker of varying length and composition. For example, the linker sequence comprises the sequence GGGGSGGGGS (SEQ ID NO: 29). The order of the two polypeptide sequences at the N- or C-terminus could also be varied. In additional embodiments, the decoy polypeptide is a multi-specific high-affinity SIRP-gamma agent. In further embodiments, the decoy polypeptide comprises one of the following sequences:

1) Fusion to immune checkpoint inhibitors
a. PD-1/PD-L1 antagonist
Example: HAC-GV3 (high-affinity PD-1 decoy fused to GV3)

(SEQ ID NO: 30)
DSPDRPWNPPTFSPALLVVTEGDNATFTCSFSNTSESFHVVWHRESPSGQ

TDTLAAFPEDRSQPGQDARFRVTQLPNGRDFHMSVVRARRNDSGTYVCGV

ISLAPKIQIKESLRAELRVTERGGGGSGGGGSEEELQIIQPEKLLLVTVG

KTATLHCTITSLFPVGPIQWFRGVGPGRVLIYNQKDGHFPRVTTVSDGTK

RNNMDFSIRISSITPADVGTYYCVKFRKGSPEDVEFKSGPGTEMALGAKP

S;

b. BTLA/CD160 antagonist
Example: GV3-BTLA decoy (SEQ ID NO: 31)
EEELQIIQPEKLLLVTVGKTATLHCTITSLFPVGPIQWFRGVGPGRVLIY

NQKDGHFPRVTTVSDGTKRNNMDFSIRISSITPADVGTYYCVKFRKGSPE

DVEFKSGPGTEMALGAKPSGGGGSGGGGSWNIHGKESCDVQLYIKRQSEH

SILAGDPFELECPVKYCANRPHVTWCKLNGTTCVKLEDRQTSWKEEKNIS

FFILHFEPVLPNDNGSYRCSANFQSNLIESHSTTLYVTDVK;

c. Phosphatidylserine antagonist
Example: GV3-MFGE8 decoy (SEQ ID NO: 32)
EEELQIIQPEKLLLVTVGKTATLHCTITSLFPVGPIQWFRGVGPGRVLIY

NQKDGHFPRVTTVSDGTKRNNMDFSIRISSITPADVGTYYCVKFRKGSPE

DVEFKSGPGTEMALGAKPSGGGGSGGGGSELNGCANPLGLKNNSIPDKQI

TASSSYKTWGLHLFSWNPSYARLDKQGNFNAWVAGSYGNDQWLQVDLGSS

KEVTGIITQGARNFGSVQFVASYKVAYSNDSANWTEYQDPRTGSSKIFPG

NWDNHSHKKNLFETPILARYVRILPVAWHNRIALRLELLGC;

Example: GV3-Tim1 decoy (SEQ ID NO: 33)
EEELQIIQPEKLLLVTVGKTATLHCTITSLFPVGPIQWFRGVGPGRVLIY

NQKDGHFPRVTTVSDGTKRNNMDFSIRISSITPADVGTYYCVKFRKGSPE

DVEFKSGPGTEMALGAKPSGGGGSGGGGSVAGSVKVGGEAGPSVTLPCHY

SGAVTSMCWNRGSCSLFTCQNGIVWTNGTHVTYRKDTRYKLLGDLSRRDV

SLTIENTAVSDSGVYCCRVEHRGWFNDMKITVSLEIVPPKVTT;

Example: GV3-Tim3 decoy (SEQ ID NO: 34)
EEELQIIQPEKLLLVTVGKTATLHCTITSLFPVGPIQWFRGVGPGRVLIY

NQKDGHFPRVTTVSDGTKRNNMDFSIRISSITPADVGTYYCVKFRKGSPE

DVEFKSGPGTEMALGAKPSGGGGSGGGGSSEVEYRAEVGQNAYLPCFYTP

AAPGNLVPVCWGKGACPVFECGNVVLRTDERDVNYWTSRYWLNGDFRKGD

VSLTIENVTLADSGIYCCRIQIPGIMNDEKFNLKLVIKPAKVTPA;

Example: GV3-Tim4 decoy (SEQ ID NO: 35)
EEELQIIQPEKLLLVTVGKTATLHCTITSLFPVGPIQWFRGVGPGRVLIY

NQKDGHFPRVTTVSDGTKRNNMDFSIRISSITPADVGTYYCVKFRKGSPE

DVEFKSGPGTEMALGAKPSGGGGSGGGGSTSETVVTEVLGHRVTLPCLYS

SWSHNSNSMCWGKDQCPYSGCKEALIRTDGMRVTSRKSAKYRLQGTIPRG

DVSLTILNPSESDSGVYCCRIEVPGWFNDVKINVRLNLQRASTTTDEKFN

LKLVIKPAKVTPA;

2) Fusion to co-stimulatory molecules
a. CD40 agonist
Example: GV3-CD40L (SEQ ID NO: 36)
EEELQIIQPEKLLLVTVGKTATLHCTITSLFPVGPIQWFRGVGPGRVLIY

NQKDGHFPRVTTVSDGTKRNNMDFSIRISSITPADVGTYYCVKFRKGSPE

DVEFKSGPGTEMALGAKPSGGGGSGGGGSGDQNPQIAAHVISEASSKTTS

VLQWAEKGYYTMSNNLVTLENGKQLTVKRQGLYYIYAQVTFCSNREASSQ

APFIASLCLKSPGRFERILLRAANTHSSAKPCGQQSIHLGGVFELQPGAS

VFVNVTDPSQVSHGTGFTSFGLLKL;

b. 41BB (CD137) agonist
Example: GV3-41BBL (SEQ ID NO: 37)
EEELQIIQPEKLLLVTVGKTATLHCTITSLFPVGPIQWFRGVGPGRVLIY

NQKDGHFPRVTTVSDGTKRNNMDFSIRISSITPADVGTYYCVKFRKGSPE

DVEFKSGPGTEMALGAKPSGGGGSGGGGSDPAGLLDLRQGMFAQLVAQNV

LLIDGPLSWYSDPGLAGVSLTGGLSYKEDTKELVVAKAGVYYVFFQMELR

RVVAGEGSGSVSLALHLMPLRSAAGAAALALTVDLPPASSEARNSAFGFQ

GRLLHLSAGQRLGVHLHTEARARHAWQLTQGATVLGLFRVTPEIPA;

3) Fusion to cytokines and attenuated cytokines
Example: GV3-IL2

(SEQ ID NO: 38)
EEELQIIQPEKLLLVTVGKTATLHCTITSLFPVGPIQWFRGVGPGRVLIY

NQKDGHFPRVTTVSDGTKRNNMDFSIRISSITPADVGTYYCVKFRKGSPE

DVEFKSGPGTEMALGAKPSGGGGSGGGGSAPTSSSTKKTQLQLEHLLLDL

QMILNGINNYKNPKLTRMLTFKFYMPKKATELKHLQCLEEELKPLEEVLN

LAQSKNFHLRPRDLISNINVIVLELKGSETTFMCEYADETATIVEFLNRW

ITFCQSIISTLT;

Example: GV3-IL2 (an "attenuated" cytokine with mutations F42A/D20T)

(SEQ ID NO: 39)
EEELQIIQPEKLLLVTVGKTATLHCTITSLFPVGPIQWFRGVGPGRVLIY

NQKDGHFPRVTTVSDGTKRNNMDFSIRISSITPADVGTYYCVKFRKGSPE

DVEFKSGPGTEMALGAKPSGGGGSGGGGSAPTSSSTKKTQLQLEHLLLTL

QMILNGINNYKNPKLTRMLTAKFYMPKKATELKHLQCLEEELKPLEEVLN

LAQSKNFHLRPRDLISNINVIVLELKGSETTFMCEYADETATIVEFLNRW

ITFCQSIISTLT.

SIRP Polypeptide Modifications

SIRP-gamma, SIRP-beta or SIRP-beta2 polypeptide variants encompass derivatives or analogs in which (i) an amino acid is substituted with an amino acid residue that is not one encoded by the genetic code, (ii) the mature polypeptide is fused with another compound such as polyethylene glycol, or (iii) additional amino acids are fused to the SIRP-gamma, SIRP-beta or SIRP-beta2 polypeptide, such as a leader or secretory sequence or a sequence for purification of the polypeptide.

Typical modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Modifications are made anywhere in a SIRP-gamma, SIRP-beta or SIRP-beta2 polypeptide, including the peptide backbone, the amino acid side-chains, and the amino or carboxyl termini. Certain common peptide modifications that are useful for modification of SIRP-gamma, SIRP-beta or SIRP-beta2 polypeptide include glycosylation, lipid attachment, sulfation, gamma-carboxylation of glutamic acid residues, hydroxylation, blockage of the amino or carboxyl group in a polypeptide, or both, by a covalent modification, and ADP-ribosylation.

Moreover, one or more amino acids of the core sequence is altered, in a conservative manner such that the requisite CD47 binding is maintained or increased. Typical substitutions are made among the following groups of amino acids: (a) G, A, V, L and I; (b) G and P; (c) S, C, T, M; (d) F, Y, and W; (e) H, K and R; and (f) D, E, N, and Q. Other substitutions include the following groups: (i) S and T; (ii) P and G; a (iii) A, V, L and I.

Also contemplated within the scope of embodiments provided herein are modifications of the SIRP-gamma, SIRP-beta or SIRP-beta2 polypeptide wherein the polypeptide is joined to another polypeptide with which it is not normally associated (e.g., Glutathione S-transferase (GST)-fusion protein, beta-galactosidase fusions, yeast two-hybrid GAL fusions, poly-His fusions, Ig fusions and the like). Thus, a SIRP-gamma, SIRP-beta or SIRP-beta2 polypeptide is optionally operatively linked, at either its N-terminus or C-terminus, to a heterologous polypeptide having an amino acid sequence not substantially homologous to the SIRP-gamma, SIRP-beta or SIRP-beta2 polypeptide. "Operatively linked" indicates that SIRP-gamma, SIRP-beta or SIRP-beta2 polypeptide and the heterologous polypeptide are both in-frame. Such a fusion protein may alter (e.g., enhances, dampens) the ability of the SIRP-gamma, SIRP-beta or SIRP-beta2 polypeptide, or a functional variant thereof, to bind CD47. Such a fusion protein may also alter (enhances, dampens) the pharmacokinetic half-life of the SIRP-gamma, SIRP-beta, or SIRP-beta2 polypeptide in a human patient or experimental animal. The fusion protein may also alter the activity that the SIRP-gamma, SIRP-beta, or SIRP-beta2 polypeptide imparts on myeloid cell activity including phagocytosis and ADCC.

Affinity

As a subject SIRP-gamma, SIRP-beta or SIRP-beta2 decoy polypeptide has an increased affinity for CD47 as compared to the affinity for CD47 of a wild type SIRP-gamma, SIRP-beta or SIRP-beta2 polypeptide, and/or as compared to the affinity for CD47 of a SIRP-gamma, SIRP-beta or SIRP-beta2 polypeptide that does not have an amino acid change relative to a corresponding sequence of a wild type SIRP-gamma, SIRP-beta or SIRP-beta2 polypeptide (e.g., a wildtype SIRP-gamma, SIRP-beta or SIRP-beta2 polypeptide, as defined above).

In some embodiments, the SIRP-gamma, SIRP-beta or SIRP-beta2 decoy polypeptide has a Kd of $1 \times 10^{-7}$ M or less (e.g., $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less) affinity for CD47. In some cases, the SIRP-gamma, SIRP-beta or SIRP-beta2 decoy polypeptide has an affinity for CD47 in a range of from 1 fM to 1 µM (e.g., from 1 fM to 800 nM, from 10 fM to 500 nM, from 100 fM to 100 nM, from 500 fM to 50 nM, from 800 fM to 50 nM, from 1 pM to 50 nM, from 10 pM to 50 nM, from 50 pM to 50 nM, from 100 pM to 50 nM, from 500 fM to 100 nM, from 800 fM to 100 nM, from 1 pM to 100 nM, from 10 pM to 100 nM, from 50 pM to 100 nM, or from 100 pM to 100 nM). In some cases, SIRP-gamma, SIRP-beta or SIRP-beta2 decoy polypeptide binds to CD47 with an affinity of 1 µM or greater (e.g., 800 nM or greater, 500 nM or greater, 200 nM or greater, 100 nM or greater, 50 nM or greater, 10 nM or greater, 1 nM or greater, 900 pM or greater, 750 pM or greater, 500 pM or greater, 200 pM or greater, 100 pM or greater, 10 pM or greater, 1 pM or greater, etc., where the affinity increases with decreasing values).

In some embodiments, the SIRP-gamma, SIRP-beta or SIRP-beta2 decoy polypeptide has an affinity for CD47 that is 2-fold or more (e.g., 5-fold or more, 10-fold or more, 100-fold or more, 500-fold or more, 1000-fold or more, 5000-fold or more, $10^4$-fold or more, $10^5$-fold or more, $10^6$-fold or more, $10^7$-fold or more, $10^8$-fold or more, etc.) greater than the affinity for CD47 of a wild type SIRP-gamma, SIRP-beta or SIRP-beta2 protein; and/or 2-fold or more (e.g., 5-fold or more, 10-fold or more, 100-fold or more, 500-fold or more, 1000-fold or more, 5000-fold or more, 104-fold or more, $10^5$-fold or more, $10^6$-fold or more, $10^7$-fold or more, $10^8$-fold or more, etc.) greater than the affinity for CD47 of a SIRP-gamma, SIRP-beta or SIRP-beta2 polypeptide that does not have an amino acid change relative to a corresponding sequence of a wild type SIRP-gamma, SIRP-beta or SIRP-beta2 polypeptide (e.g., a wildtype SIRP-gamma, SIRP-beta or SIRP-beta2 polypeptide, as defined above).

In some embodiments, the SIRP-gamma, SIRP-beta or SIRP-beta2 decoy polypeptide has a dissociation half-life for CD47 that is 2-fold or more (e.g., 5-fold or more, 10-fold or more, 100-fold or more, 500-fold or more, 1000-fold or more, 5000-fold or more, $10^4$-fold or more, $10^5$-fold or more, $10^6$-fold or more, $10^7$-fold or more, $10^8$-fold or more, etc.) greater than the dissociation half-life for CD47 of a wild type SIRP-gamma, SIRP-beta or SIRP-beta2 protein; and/or 2-fold or more (e.g., 5-fold or more, 10-fold or more, 100-fold or more, 500-fold or more, 1000-fold or more, 5000-fold or more, $10^4$-fold or more, $10^5$-fold or more, $10^6$-fold or more, $10^7$-fold or more, $10^8$-fold or more, etc.) greater than the dissociation half-life for CD47 of a SIRP-gamma, SIRP-beta or SIRP-beta2 decoy polypeptide that does not have an amino acid change relative to a corresponding sequence of a wild type SIRP-gamma, SIRP-beta or SIRP-beta2 polypeptide (e.g., a wildtype SIRP-gamma, SIRP-beta or SIRP-beta2 decoy polypeptide, as defined above). For example, in some cases, a wildtype SIRP-gamma, SIRP-beta or SIRP-beta2 polypeptide (as defined above) has a dissociation half-life for CD47 of less than 1 second, while a subject SIRP-gamma, SIRP-beta or SIRP-beta2 decoy polypeptide can have a dissociation half-life of 5 seconds or more (e.g., 30 seconds or more, 1 minute or more, 5 minutes or more, 10 minutes or more, 20 minutes or more, 30 minutes or more, 40 minutes or more, etc.). For example, the amino acid substitution of a subject SIRP-gamma, SIRP-beta or SIRP-beta2 decoy polypeptide can increase the affinity by decreasing the off-rate by at least 10-fold, at least 20-fold, at least 50-fold, at least 100-fold, at least 500-fold, or more.

The affinity to bind to CD47 can be determined, for example, by the ability of SIRP-gamma, SIRP-beta or SIRP-beta2decoy polypeptide to bind to CD47 coated on an assay plate; displayed on a microbial cell surface; in solution; etc. The binding activity of SIRP-gamma, SIRP-beta or SIRP-beta2 decoy polypeptides of the present disclosure to CD47 can be assayed by immobilizing the ligand (e.g., CD47) or the SIRP-gamma, SIRP-beta or SIRP-beta2 decoy polypeptide, to a bead, substrate, cell, etc. Agents can be added in an appropriate buffer and the binding partners incubated for a period of time at a given temperature. After washes to remove unbound material, the bound protein can be released with, for example, SDS, buffers with a high pH, and the like and analyzed, for example, by Surface Plasmon Resonance (SPR).

Binding can also be determined by, for example, measuring the ability of a unlabeled SIRP-gamma, SIRP-beta or SIRP-beta2 decoy polypeptide to compete with a labeled SIRP-gamma, SIRP-beta or SIRP-beta2 polypeptide (e.g., a labeled wildtype SIRP-gamma, SIRP-beta or SIRP-beta2 polypeptide, as defined above) for binding to CD47. Accordingly, relative biding can be assessed by comparing the results using a candidate unlabeled SIRP-gamma, SIRP-beta or SIRP-beta2 decoy polypeptide to results using an unlabeled wildtype SIRP-gamma, SIRP-beta or SIRP-beta2 polypeptide (as defined above, a wildtype SIRP-gamma, SIRP-beta or SIRP-beta2 decoy polypeptide that does not have an amino acid change relative to the corresponding sequence of a wild type SIRP-gamma, SIRP-beta or SIRP-beta2).

Any convenient method can be used to generate a subject SIRP-gamma, SIRP-beta or SIRP-beta2 decoy polypeptide. As one example non-limiting example, mutagenesis can be performed (beginning with a wildtype SIRP-gamma, SIRP-beta or SIRP-beta2 polypeptide, or beginning with a SIRP-gamma, SIRP-beta or SIRP-beta2 decoy polypeptide for the purpose of generating a polypeptide with even greater affinity) to generate collections of mutated SIRP-gamma, SIRP-beta or SIRP-beta2 decoy polypeptides. Mutagenesis can be targeted to produce changes at particular amino acids, or mutagenesis can be random. The mutated SIRP-gamma, SIRP-beta or SIRP-beta2 decoy polypeptides can then be screen for their ability to bind a CD47 protein. For example, a CD47 protein (or a variant of a CD47 protein, e.g., a version lacking a transmembrane domain) can be labeled (e.g., with a direct label such as a radioisotope, a fluorescent moiety, etc.; or with an indirect label such as an antigen, an affinity tag, biotin, etc.) and then can be used to contact the candidate SIRP-gamma, SIRP-beta or SIRP-beta2 decoy polypeptides (e.g., where the candidate SIRP-gamma, SIRP-beta or SIRP-beta2 decoy polypeptides can be attached to a solid surface or displayed on the membrane of a cell, e.g., a yeast cell). By varying the concentration of CD47 used, one can identify high-affinity SIRP-gamma, SIRP-beta or SIRP-beta2 decoy polypeptides from among the candidates (i.e., from among the collection of mutated SIRP-gamma, SIRP-beta or SIRP-beta2 decoy polypeptides).

Methods of Treatment

Provided herein, in some embodiments, are methods and uses for stimulating the immune system of an individual in need thereof comprising administration of a decoy polypeptide described herein (e.g., a SIRP-gamma, SIRP-beta or SIRP-beta2 polypeptide variant). In some instances, the administration of decoy polypeptide described herein induces and/or sustains phagocytosis of a cell expressing CD47. In other instances, the administration of a decoy polypeptide described herein induces and/or sustains phagocytosis of a cell not expressing CD47. In some instances, the cell is a cancer cell, a virally infected cell, a bacterially infected cell, an autoreactive T or B cell, damaged red blood cells, arterial plaques, or fibrotic tissue. In additional instances, the cell is a healthy normal cell such as hematopoietic stem cell, a healthy myeloid or lymphoid precursor cell, or a healthy differentiated hematopoietic cell type such as T, B, plasma, or NK cells.

Also provided herein are methods and uses for treatment of cancer in an individual in need thereof comprising administration of a decoy polypeptide described herein. In some of such embodiments, the individual is suffering from cancer. In other embodiments, the individual is suspected to be suffering from cancer. In yet other embodiments, the individual is pre-disposed to cancer (e.g., an individual pre-disposed to breast cancer). In certain embodiments, the cancer is selected from the group consisting of breast cancer, lung cancer, adenocarcinoma of the lung, squamous cell lung cancer, small cell lung cancer, non-small cell lung cancer, head and neck cancer, brain cancer, abdominal cancer, colon cancer, colorectal cancer, esophageal cancer, parapharyngeal cancer, gastrointestinal cancer, glioma, liver cancer, oral cancer, tongue cancer, neuroblastoma, osteosarcoma, ovarian cancer, renal cancer, urinary bladder cancer, urinary tract cancer, pancreatic cancer, retinoblastoma, cervical cancer, uterine cancer, Wilm's tumor, multiple myeloma, skin cancer, lymphoma, leukemia, blood cancer, thyroid cancer, bone cancer, adenocystic tumor, chondrosarcoma, pancreatic islet cell tumor, neuroendocrine tumor, prostate cancer, ovarian cancer, glioblastoma, endometrial carcinoma, endometrial cancer, leiomyosarcoma, gall bladder cancer, hepatocellular cancer, hematological cancer, multiple myeloma, acute myelogenous leukemia, acute/chronic lymphoblastic leukemia, hairy-cell leukemia, follicular lymphoma, multiple myeloma, plasmacytoma, diffuse large B-cell lymphoma. In some embodiments, the cancer is a hematological cancer. In particular aspects, the cancer is multiple myeloma, acute/chronic myelogenous leukemia, acute/chronic lymphoblastic leukemia, hairy-cell leukemia, follicular lymphoma, multiple myeloma, plasmacytoma or diffuse large B-cell lymphoma.

In some embodiments, the cancer is associated with expression of CD47 including but not limited to Acute myeloid leukemia (AML), Acute leukocytic leukemia (ALL), Hodgkin's lymphoma (HL), Non-Hodgkin's B cell lymphoma (NHBCL), Chronic leukocytic leukemia (B-CLL), Multiple myeloma (MM), pancreatic adenocarcinoma, pancreatic neuroendocrine tumor (PanNET), glioma, medulloblastoma, astrocytoma, prostate cancer, osteosarcoma, small cell lung carcinoma (SCLC), non-small cell lung carcinoma (NSCLC), melanoma, squamous cell head and neck carcinoma, prostate carcinoma, ovarian cancer, breast cancer, colon cancer, renal cancer, and bladder cancer. In some embodiments, the cancer is associated with solid tumors. In certain instances, the solid tumors are advanced, e.g., stage 3 or 4. In certain instances, the solid tumors are histologically associated with the expression of the CD47.

As used herein, in some embodiments, "treatment" or "treating" or "treated" refers to therapeutic treatment wherein the object is to slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. In other embodiments, "treatment" or "treating" or "treated" refers to prophylactic measures, wherein the object is to delay onset of or reduce severity of an undesired physiological condition, disorder or disease, such as, for example is a person who is predisposed to a disease (e.g., an individual who carries a genetic marker for a disease such as breast cancer).

The methods of treatment described herein treat various stages of cancer including stages which are locally advanced, metastatic and/or recurrent. In cancer staging, locally advanced is generally defined as cancer that has spread from a localized area to nearby tissues and/or lymph nodes. In the Roman numeral staging system, locally advanced usually is classified in Stage II or III. Cancer which is metastatic is a stage where the cancer spreads throughout the body to distant tissues and organs (stage IV). Cancer designated as recurrent generally is defined as the cancer has recurred, usually after a period of time, after being in remission or after a tumor has visibly been eliminated. Recurrence can either be local, i.e., appearing in the same location as the original, or distant, i.e., appearing in a different part of the body. In certain instances, a cancer treatable by combination therapies described herein is unresectable, or unable to be removed by surgery.

In some of such embodiments, the methods of treatment described herein provide adjunct therapy to any other cancer therapy prescribed for an individual. Accordingly, in some embodiments, decoy polypeptides described herein are administered in combination with treatment with any other anti-cancer agent including and not limited to methotrexate (RHEUMATREX®, Amethopterin) cyclophosphamide (CYTOXAN®), thalidomide (THALIDOMID®), acridine carboxamide, Actimid®, actinomycin, 17-N-allylamino-17-demethoxygeldanamycin, aminopterin, amsacrine, anthracycline, antineoplastic, antineoplaston, 5-azacytidine, azathioprine, BL22, bendamustine, biricodar, bleomycin, bortezomib, bryostatin, busulfan, calyculin, camptothecin, capecitabine, carboplatin, cetuximab, chlorambucil, cisplatin, cladribine, clofarabine, cytarabine, dacarbazine, dasatinib, daunorubicin, decitabine, dichloroacetic acid, discodermolide, docetaxel, doxorubicin, epirubicin, epothilone, eribulin, estramustine, etoposide, exatecan, exisulind, ferruginol, floxuridine, fludarabine, fluorouracil, fosfestrol, fotemustine, ganciclovir, gemcitabine, hydroxyurea, IT-101, idarubicin, ifosfamide, imiquimod, irinotecan, irofulven, ixabepilone, laniquidar, lapatinib, lenalidomide, lomustine, lurtotecan, mafosfamide, masoprocol, mechlorethamine, melphalan, mercaptopurine, mitomycin, mitotane, mitoxantrone, nelarabine, nilotinib, oblimersen, oxaliplatin, PAC-1, paclitaxel, pemetrexed, pentostatin, pipobroman, pixantrone, plicamycin, procarbazine, proteasome inhibitors (e.g., bortezomib), raltitrexed, rebeccamycin, Revlimid®, rubitecan, SN-38, salinosporamide A, satraplatin, streptozotocin, swainsonine, tariquidar, taxane, tegafur-uracil, temozolomide, testolactone, thioTEPA, tioguanine, topotecan, trabectedin, tretinoin, triplatin tetranitrate, tris(2-chloroethyl) amine, troxacitabine, uracil mustard, valrubicin, vinblastine, vincristine, vinorelbine, vorinostat, zosuquidar, or the like.

In additional embodiments, the methods of treatment described herein i.e., decoy polypeptide formulations described herein are administered in combination with monoclonal antibodies such as 3F8, 8H9, Abagovomab, Abciximab, Abituzumab, Abrilumab, Actoxumab, Adalimumab, Adecatumumab, Aducanumab, Afelimomab, Afutuzumab, Alacizumab pegol, ALD518, Alemtuzumab, Alirocumab, Altumomab pentetate, Amatuximab, Anatumomab mafenatox, Anetumab ravtansine, Anifrolumab, Anrukinzumab (IMA-638), Apolizumab, Arcitumomab, Ascrinvacumab, Aselizumab, Atezolizumab, Atinumab, Atlizumab (tocilizumab), Atorolimumab, Bapineuzumab, Basiliximab, Bavituximab, Bectumomab, Begelomab, Belimumab, Benralizumab, Bertilimumab, Besilesomab, Bevacizumab, Bezlotoxumab, Biciromab, Bimagrumab, Bimekizumab, Bivatuzumab mertansine, Blinatumomab, Blosozumab, Bococizumab, Brentuximab vedotin, Briakinumab, Brodalumab, Brolucizumab, Brontictuzumab, Canakinumab, Cantuzumab mertansine, Cantuzumab ravtansine, Caplacizumab, Capromab pendetide, Carlumab, Catumaxomab, cBR96-doxorubicin immunoconjugate, CC49, Cedelizumab, Certolizumab pegol, Cetuximab, Ch.14.18, Citatuzumab bogatox, Cixutumumab, Clazakizumab, Clenoliximab, Clivatuzumab tetraxetan, Codrituzumab, Coltuximab ravtansine, Conatumumab, Concizumab, Crenezumab, CR6261, Dacetuzumab, Daclizumab, Dalotuzumab, Dapirolizumab pegol, Daratumumab, Dectrekumab, Demcizumab, Denintuzumab mafodotin, Denosumab, Derlotuximab biotin, Detumomab, Dinutuximab, Diridavumab, Dorlimomab aritox, Drozitumab, Duligotumab, Dupilumab, Durvalumab, Dusigitumab, Ecromeximab, Eculizumab, Edobacomab, Edrecolomab, Efalizumab, Efungumab, Eldelumab, Elgemtumab, Elotuzumab, Elsilimomab, Emactuzumab, Emibetuzumab, Enavatuzumab, Enfortumab vedotin, Enlimomab pegol, Enoblituzumab, Enokizumab, Enoticumab, Ensituximab, Epitumomab cituxetan, Epratuzumab, Erlizumab, Ertumaxomab, Etaracizumab, Etrolizumab, Evinacumab, Evolocumab, Exbivirumab, Fanolesomab, Faralimomab, Farletuzumab, Fasinumab, FBTA05, Felvizumab, Fezakinumab, Ficlatuzumab, Figitumumab, Firivumab, Flanvotumab, Fletikumab, Fontolizumab, Foralumab, Foravirumab, Fresolimumab, Fulranumab, Futuximab, Galiximab, Ganitumab, Gantenerumab, Gavilimomab, Gemtuzumab ozogamicin, Gevokizumab, Girentuximab, Glembatumumab vedotin, Golimumab, Gomiliximab, Guselkumab, Ibalizumab, Ibritumomab tiuxetan, Icrucumab, Idarucizumab, Igovomab, IMAB362, Imalumab, Imciromab, Imgatuzumab, Inclacumab, Indatuximab ravtansine, Indusatumab vedotin, Infliximab, Intetumumab, Inolimomab, Inotuzumab ozogamicin, Ipilimumab, Iratumumab, Isatuximab, Itolizumab, Ixekizumab, Keliximab, Labetuzumab, Lambrolizumab, Lampalizumab, Lebrikizumab, Lemalesomab, Lenzilumab, Lerdelimumab, Lexatumumab, Libivirumab, Lifastuzumab vedotin, Ligelizumab, Lilotomab satetraxetan, Lintuzumab, Lirilumab, Lodelcizumab, Lokivetmab, Lorvotuzumab mertansine, Lucatumumab, Lulizumab pegol, Lumiliximab, Lumretuzumab, Mapatumumab, Margetuximab, Maslimomab, Mavrilimumab, Matuzumab, Mepolizumab, Metelimumab, Milatuzumab, Minretumomab, Mitumomab, Mogamulizumab, Morolimumab, Motavizumab, Moxetumomab pasudotox, Muromonab-CD3, Nacolomab tafenatox, Namilumab, Naptumomab estafenatox, Narnatumab, Natalizumab, Nebacumab, Necitumumab, Nemolizumab, Nerelimomab, Nesvacumab, Nimotuzumab, Nivolumab, Nofetumomab merpentan, Obiltoxaximab, Ocaratuzumab, Ocrelizumab, Odulimomab, Ofatumumab, Olaratumab, Olokizumab, Omalizumab, Onartuzumab, Ontuxizumab, Opicinumab, Oportuzumab monatox, Oregovomab, Orticumab, Otelixizumab, Otlertuzumab, Oxelumab, Ozanezumab, Ozoralizumab, Pagibaximab, Palivizumab, Panitumumab, Pankomab, Panobacumab, Parsatuzumab, Pascolizumab, Pasotuxizumab, Pateclizumab, Patritumab, Pembrolizumab, Pemtumomab, Perakizumab, Pertuzumab, Pexelizumab, Pidilizumab, Pinatuzumab vedotin, Pintumomab, Placulumab, Polatuzumab vedotin, Ponezumab, Priliximab, Pritoxaximab, Pritumumab, PRO 140, Quilizumab, Racotumomab, Radretumab, Rafivirumab, Ralpancizumab, Ramucirumab, Ranibizumab, Raxibacumab, Refanezumab, Regavirumab, Reslizumab, Rilotumumab, Rinucumab, Rituximab, Robatumumab, Roledumab, Romosozumab, Rontalizumab, Rovelizumab, Ruplizumab, Samalizumab, Sarilumab, Satumomab pendetide, Secukinumab, Seribantumab, Setoxaximab, Sevirumab, Sibrotuzumab, SGN-CD19A, SGN-CD33A, Sifalimumab, Siltuximab, Simtuzumab, Siplizumab, Sirukumab, Sofituzumab vedotin, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tarextumab, Tefibazumab, Telimomab aritox, Tenatumomab, Teneliximab, Teplizumab, Teprotumumab, Tesidolumab, TGN1412, Ticilimumab (tremelimumab), Tildrakizumab, Tigatuzumab, TNX-650, Tocilizumab (atlizumab), Toralizumab, Tosatoxumab, Tositumomab, Tovetumab, Tralokinumab, Trastuzumab, TRBS07, Tregalizumab, Tremelimumab, Tucotuzumab celmoleukin, Tuvirumab, Ublituximab, Ulocuplumab, Urelumab, Urtoxazumab, Ustekinumab, Vandortuzumab vedotin, Vantictumab, Vanucizumab, Vapaliximab, Varlilumab, Vatelizumab, Vedolizumab, Veltuzumab, Vepalimomab, Vesencumab, Visilizumab, Volociximab, Vorsetuzumab mafodotin, Votumumab, Zalutumumab, Zanolimumab, Zatuximab, Ziralimumab, or Zolimomab aritox.

In additional embodiments, the methods of treatment described herein i.e., decoy polypeptide formulations described herein are administered in combination with a monoclonal antibody targeting one or more of VWF, vimentin, VEGFR2, VEGFR-1, VEGF-A, TYRP1(glycoprotein 75), TWEAK receptor, tumor specific glycosylation of MUC1, tumor antigen CTAA16.88, TRAIL-R2, TRAIL-R1, TNF-α, TGF-β, TGF beta 2, TGF beta 1, TFPI, tenascin C, TEM1, TAG-72, T-cell receptor, STEAP1, sphingosine-1-phosphate, SOST, SLAMF7, selectin P, SDC1, sclerostin, RTN4, RON, Rhesus factor, RHD, respiratory syncytial virus, RANKL, rabies virus glycoprotein, platelet-derived growth factor receptor beta, phosphatidylserine, phosphate-sodium co-transporter, PDGF-R α, PDCD1, PD-1, PCSK9, oxLDL, OX-40, NRP1, Notch receptor 4, Notch receptor 3, Notch receptor 2, Notch receptor 1, NOGO-A, NGF, neural apoptosis-regulated proteinase 1, NCA-90 (granulocyte antigen), NARP-1, N-glycolylneuraminic acid, myostatin, myelin-associated glycoprotein, mucin CanAg, MUC1, MSLN, MS4A1, MIF, mesothelin, MCP-1, LTA, LOXL2, lipoteichoic acid, LINGO-1, LFA-1 (CD11a), Lewis-Y antigen, L-selectin (CD62L), KIR2D, ITGB2 (CD18), ITGA2, interferon α/β receptor, interferon receptor, interferon gamma-induced protein, integrin αvβ3, integrin αIIbβ3, integrin α7β7, integrin α5β1, integrin α4β7, integrin α4, insulin-like growth factor I receptor, Influenza A hemagglutinin, ILGF2, IL9, IL6, IL4, IL31RA, IL23, IL17A, IL-6 receptor, IL-6, IL-5, IL-4, IL-23, IL-22, IL-1β, IL-17A, IL-17, IL-13, IL-12, IL-1, IL 20, IGHE, IgG4, IGF-I, IGF-1 receptor, IgE Fc region, IFN-γ, IFN-α, ICAM-1 (CD54), human TNF, human scatter factor receptor kinase, Hsp90, HNGF, HLA-DR, HIV-1, histone complex, HHGFR, HGF, HER3, HER2/neu, HER1, hepatitis B surface antigen, hemagglutinin, GUCY2C, GPNMB, GMCSF receptor α-chain, glypican 3, GD3 ganglioside, GD2, ganglioside GD2, Frizzled receptor, folate receptor 1, folate hydrolase, fibronectin extra domain-B, fibrin II, beta chain, FAP, F protein of respiratory syncytial virus, ERBB3, episialin, EpCAM, endotoxin, EGFR, EGFL7, E. coli shiga toxin type-2, E. coli shiga toxin type-1, DRS, DPP4, DLL4, dabigatran, cytomegalovirus glycoprotein B, CTLA-4, CSF2, CSF1R, clumping factor A, CLDN18.2, ch4D5, CFD, CEA-related antigen, CEA, CD80, CD79B, CD74, CD70, CD6, CD56, CD52, CD51, CD5, CD44 v6, CD41, CD40 ligand, CD40, CD4, CD38, CD37, CD33, CD30 (TNFRSF8), CD3 epsilon, CD3, CD28, CD274, CD27, CD25 (α chain of IL-2 receptor), CD23 (IgE receptor), CD221, CD22, CD200, CD20, CD19, CD154, CD152, CD15, CD147 (basigin), CD140a, CD125, CD11, CD-18, CCR5, CCR4, CCL11 (eotaxin-1), cardiac myosin, carbonic anhydrase 9 (CA-IX), *Canis lupus familiaris* IL31, CA-125, C5, C242 antigen, C-X-C chemokine receptor type 4, beta-amyloid, BAFF, B7-H3, B-lymphoma cell, AOC3 (VAP-1), anthrax toxin, protective antigen, angiopoietin 3, angiopoietin 2, alpha-fetoprotein, AGS-22M6, adenocarcinoma antigen, ACVR2B, activin receptor-like kinase 1, 5T4, SAC, 4-1BB or 1-40-β-amyloid.

In additional embodiments, the methods of treatment described herein i.e., decoy polypeptide formulations described herein are administered in combination with radiotherapy (e.g., γ-rays, X-rays, and/or the directed delivery of radioisotopes to tumor cells, microwaves, UV radiation and the like. In additional embodiments, the methods of treatment described herein i.e., decoy polypeptides described herein are administered in combination with gene therapy. Therapeutic genes include an antisense version of an inducer of cellular proliferation (oncogene), an inhibitor of cellular proliferation (tumor suppressor), or an inducer of programmed cell death (pro-apoptotic gene). In some embodiments, the combination therapies described herein are administered with a surgery (e.g., resection).

In additional embodiments, the methods of treatment described herein i.e., decoy polypeptides described herein are administered in combination with anti-diarrheal agents, anti-emetic agents, analgesics, opioids and/or non-steroidal anti-inflammatory agents.

In further embodiments, decoy polypeptide described herein (e.g., a composition comprising a SIRP-gamma, SIRP-beta or SIRP-beta2 polypeptide) is administered to an individual who has been pre-treated with cyclophosphamide, or imitanib, or daclizumab and/or any other anti-cancer agent. In other embodiments, a decoy polypeptide described herein is administered to an individual who has not been pre-treated with cyclophosphamide and/or any other anti-cancer agent.

In some of the above embodiments, treatment with a decoy polypeptide described herein (e.g., a composition comprising a SIRP-gamma, SIRP-beta or SIRP-beta2 polypeptide) prolongs lifespan and/or increases survival rates for individuals suffering from cancer. In some of the above embodiments, treatment with a decoy polypeptide described herein (e.g., a composition comprising a SIRP-gamma, SIRP-beta or SIRP-beta2 polypeptide) improves quality of life for an individual suffering from cancer (e.g., an individual needs a lower dose of an anti-cancer drug that causes side-effects when the individual is treated with a decoy polypeptide described herein).

In some of the above embodiments, treatment with a decoy polypeptide described herein (e.g., a composition comprising a SIRP-gamma, SIRP-beta or SIRP-beta2 polypeptide) induces and/or sustains phagocytosis or ADCC in an individual. Phagocytosis includes phagocytosis by professional phagocytes (e.g. monocytes, macrophages, neutrophils, dendritic cells or mast cells), non-professional phagocytes (e.g. epithelial cells, endothelial cells, fibroblasts or mesenchymal cells) or both. ADCC includes antibody dependence cell-mediated cytotoxicity by myeloid cells including neutrophils, monocytes, and natural killer cells. Measurement of phagocytosis and ADCC is accomplished by any known method including, for example, fluorescence microscopy or flow cytometry.

In further embodiments, treatment with a decoy polypeptide described herein (e.g., a composition comprising a SIRP-gamma, SIRP-beta or SIRP-beta2 polypeptide) induces and/or enhances antibody-dependent cell-mediated phagocytosis (ADCP) or ADCC of IgE producing B and plasma cells by combining the SIRP-beta or SIRP-gamma agents with antibodies against Mlprime or CD38 in an individual with asthma or allergy.

Also provided herein are methods for treating a viral infection, disorder or condition in an individual comprising administering to an individual having a viral infection, disorder or condition a decoy polypeptide described herein. In particular aspects, the viral infection, disorder or condition is chronic. In further aspects, the viral infection, disorder or condition is acute. In further aspects, the viral infection, disorder or condition is an Adenoviridae such as, Adenovirus; a Herpesviridae such as Herpes simplex, type 1, Herpes simplex, type 2, Varicella-zoster virus, Epstein-barr virus, Human cytomegalovirus, Human herpesvirus, type 8; a Papillomaviridae such as Human papillomavirus; a Polyomaviridae such as BK virus or JC virus; a Poxviridae such as Smallpox; a Hepadnaviridae such as Hepatitis B virus; a Parvoviridae such as Human bocavirus or Parvovirus; a Astroviridae such as Human astrovirus; a Caliciviridae such as Norwalk virus; a Picornaviridae such as coxsackievirus, hepatitis A virus, poliovirus, rhinovirus; a Coronaviridae such as Severe acute respiratory syndrome virus; a Flaviviridae such as Hepatitis C virus, yellow fever virus, dengue virus, West Nile virus; a Togaviridae such as Rubella virus; a Hepeviridae such as Hepatitis E virus; a Retroviridae such as Human immunodeficiency virus (HIV); a Orthomyxoviridae such as Influenza virus; a Arenaviridae such as Guanarito virus, Junin virus, Lassa virus, Machupo virus, Sabia virus; a Bunyaviridae such as Crimean-Congo hemorrhagic fever virus; a Filoviridae such as Ebola virus, Marburg virus; a Paramyxoviridae such as Measles virus, Mumps virus, Parainfluenza virus, Respiratory syncytial virus, Human metapneumovirus, Hendra virus, Nipah virus; a Rhabdoviridae such as Rabies virus; Hepatitis D virus; or a Reoviridae such as Rotavirus, Orbivirus, Coltivirus, Banna virus. In particular aspects, the viral infection, disorder or condition is Human immunodeficiency virus (HIV), Human cytomegalovirus, Epstein-barr virus, Hepatitis C virus, or Hepatitis B virus.

Also provided herein are methods for treating a bacterial infection, disorder or condition in an individual comprising administering to an individual having a bacterial infection, disorder or condition a decoy polypeptide described herein. In particular aspects, the bacterial infection, disorder or condition is chronic. In other aspects, the bacterial infection, disorder or condition is acute. In further aspects the bacterial infection is a *Bacillus* such as *Bacillus anthracis* or *Bacillus cereus*; a *Bartonella* such as *Bartonella henselae* or *Bartonella quintana*; a *Bordetella* such as *Bordetella pertussis*; a *Borrelia* such as *Borrelia burgdorferi, Borrelia garinii, Borrelia afzelii, Borrelia recurrentis*; a *Brucella* such as *Brucella abortus*, a *Brucella canis, Brucella melitensis* or *Brucella suis*; a *Campylobacter* such as *Campylobacter jejuni*; a *Chlamydia* or *Chlamydophila* such as *Chlamydia pneumoniae, Chlamydia trachomatis, Chlamydophila psittaci*; a *Clostridium* such as *Clostridium botulinum*, a *Clostridium difficile, Clostridium perfringens, Clostridium tetani*; a *Corynebacterium* such as *Corynebacterium diphtheriae*; an *Enterococcus* such as *Enterococcus faecalis* or *Enterococcus faecium*; a *Escherichia* such as *Escherichia coli*; a *Francisella* such as *Francisella tularensis*; a *Haemophilus* such as *Haemophilus influenzae*; a *Helicobacter* such as *Helicobacter pylori*; a *Legionella* such as *Legionella pneumophila*; a *Leptospira* such as *Leptospira interrogans, Leptospira santarosai, Leptospira weilii* or *Leptospira noguchii*; a *Listeria* such as *Listeria monocytogenes*; a *Mycobacterium* such as *Mycobacterium leprae, Mycobacterium tuberculosis* or *Mycobacterium ulcerans*; a *Mycoplasma* such as *Mycoplasma pneumoniae*; a *Neisseria* such as *Neisseria gonorrhoeae* or *Neisseria meningitidis*; a *Pseudomonas* such as *Pseudomonas aeruginosa*; a *Rickettsia* such as *Rickettsia rickettsii*; a *Salmonella* such as *Salmonella typhi* or *Salmonella typhimurium*; a *Shigella* such as *Shigella sonnei*; a *Staphylococcus* such as *Staphylococcus aureus, Staphylococcus epidermidis, Staphylococcus saprophyticus*; a *Streptococcus* such as *Streptococcus agalactiae, Streptococcus pneumoniae, Streptococcus pyogenes*; a *Treponema* such as *Treponema pallidum*; a *Vibrio* such as *Vibrio cholerae*; a *Yersinia* such as *Yersinia pestis, Yersinia enterocolitica* or *Yersinia pseudotuberculosis*.

Also provided herein are methods for treating anemia in an individual comprising administering to an individual having anemia a decoy polypeptide described herein. In particular embodiments the anemia is a thalassemia, an aplastic anemia, a haemolytic anemia, a sickle cell anemia, a pernicious anemia or a fanconi anemia.

Also provided herein are methods for treating a person undergoing a transplant comprising administering to an individual undergoing an organ transplant a decoy polypeptide described herein. In particular aspects, the transplant is a heart, a lung, a heart and lung, a kidney, a liver, a pancreas, an intestine, a stomach, a testis, a hand, a cornea, skin, islets of Langerhans, bone marrow, stem cells, blood, a blood vessel, a heart valve, or a bone.

Also provided herein are methods for treating a person with autoimmune disease comprising administering to an individual with autoimmune disease a decoy polypeptide described herein. In particular aspects, the autoimmune disease is Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal & neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic, esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo or Wegener's granulomatosis (now termed Granulomatosis with Polyangiitis (GPA)). The diseases described above fall into this category; depletion of autoreactive T or B cells may both be part of a regimen to treat the listed autoimmune diseases.

Methods of Visualization

Also provided herein are methods for visualizing a cell expressing CD47 comprising contacting a population of cells with a decoy polypeptide described herein and a detectable label. In some embodiments of the methods described herein the methods include visualization of a tumor cell, a virally infected cell, a bacterially infected cell, an autoreactive T cell, damaged red blood cells, arterial plaques, or fibrotic tissue. In additional embodiments, the cell is a healthy normal cell such as hematopoietic stem cell, a healthy myeloid or lymphoid precursor cell, or a healthy differentiated hematopoietic cell type such as T, B, plasma, or NK cells. In additional embodiments of the methods described herein the methods include visualization of a cell in vivo, visualization of a cell ex vivo or visualization of a cell in vitro. In particular aspects, the method is microscopy, fluorescent microscopy, fluorescence activated cell sorting or positron emission tomography (PET) imaging. In particular aspects, the detectable label comprises an enzymatic label such as horseradish peroxidase (HRP), alkaline phosphatase (AP) or glucose oxidase. In additional aspects, the detectable label comprises a fluorescent label such as Alexa Fluor® 350, Alexa Fluor® 405, Alexa Fluor® 488, Alexa Fluor® 532, Alexa Fluor® 546, Alexa Fluor® 555, Alexa Fluor® 568, Alexa Fluor® 594, Alexa Fluor® 647, Alexa Fluor® 680, Alexa Fluor® 750, BODIPY® FL, Coumarin, Cy®3, Cy®5, Fluorescein (FITC), Oregon Green®, Pacific Blue™, Pacific Green™, Pacific Orange™, Tetramethylrhodamine (TRITC), Texas Red® or other fluorescent label. In further aspects, the detectable label comprises a radioactive isotope such as 32P, 33P, 3H, 14C, 125I or other radioactive isotope. In further aspects, the method is a diagnostic.

Dosages

When a SIRP-gamma, SIRP-beta or SIRP-beta2 decoy polypeptide described herein, (e.g., a variant SIRP-gamma, SIRP-beta or SIRP-beta2 polypeptide), is being given to an individual, one of skill in the art understands that the dosage depends on several factors, including, but not limited to, the individual's weight and disease state. Generally, as used herein, an individual that receives a SIRP-gamma, SIRP-beta or SIRP-beta2 decoy polypeptide described herein (e.g., a composition comprising a variant SIRP-gamma, SIRP-beta or SIRP-beta2 polypeptide), is a single organism. In certain embodiments, an individual will be a mammal. Specifically, an individual is a human, including being a male or a female. In many embodiments, the individual will be a patient, or an individual awaiting or under medical care and treatment.

In some embodiments, an individual is administered a dose normalized to the body weight of the individual. In some embodiments, an individual is administered a dose of about 10 µg/kg, about 50 µg/kg, about 100 µg/kg, about 200 µg/kg, about 300 µg/kg, about 400 µg/kg, about 500 µg/kg, about 600 µg/kg, about 700 µg/kg, about 800 µg/kg, about 900 µg/kg, about 1,000 µg/kg, about 1,100 µg/kg, 1,200 µg/kg, 1,300 µg/kg, 1,400 µg/kg, 1,500 µg/kg, 1,600 µg/kg, 1,700 µg/kg, 1,800 µg/kg, 1,900 µg/kg, about 2,000 µg/kg, about 3000 µg/kg, about 4000 µg/kg, about 5000 µg/kg, about 6000 µg/kg, about 7000 µg/kg, about 8000 µg/kg, about 9000 µg/kg, about 10 mg/kg, about 20 mg/kg, about 30 mg/kg, about 40 mg/kg, about 50 mg/kg, about 60 mg/kg, about 70 mg/kg, about 80 mg/kg about 90 mg/kg, about 100 mg/kg, about 200 mg/kg, about 300 mg/kg, about 400 mg/kg, about 500 mg/kg, about 600 mg/kg, about 700 mg/kg, about 800 mg/kg, about 900 mg/kg, or about 1000 mg/kg of a decoy SIRP-gamma, SIRP-beta or SIRP-beta2 polypeptide described herein (e.g., composition comprising a variant SIRP-gamma, SIRP-beta or SIRP-beta2 polypeptide), in either single or cumulative applications. In specific embodiments, the dose given to the individual is about 7000 mg/kg of decoy polypeptide per week. In specific embodiments, the dose given to the individual is about 70 mg/kg of decoy polypeptide per week. In specific embodiments, the dose given to the individual is about 7 mg/kg of decoy polypeptide per week. In specific embodiments, the dose given to the individual is about 1,000 µg of decoy polypeptide per week. In specific embodiments, the dose given to the individual is 500 µg of decoy polypeptide per week. In specific embodiments, the dose given to the individual is 250 µg of decoy polypeptide per week. In specific embodiments, the dose given to the individual is 100 µg of decoy polypeptide per week. In specific embodiments, the dose given to the individual is 50 µg of decoy polypeptide per week.

In some embodiments, an individual will receive a dose of the decoy SIRP-gamma, SIRP-beta or SIRP-beta2 polypeptide described herein (e.g., a composition comprising a variant SIRP-gamma, SIRP-beta or SIRP-beta2 polypeptide), for example, multiple times daily, every day, every other day, once a week, once every other week, once every three weeks, once per month or any other suitable dosing regimen. In one embodiment, an individual will receive a dose of the decoy SIRP-gamma, SIRP-beta or SIRP-beta2 polypeptide as a continuous infusion. In one embodiment, routinely administering encompasses administering a dose of a decoy polypeptide described herein once a week for a period of time. Of course, the dosing regimen optionally comprises other permutations of decoy polypeptide delivery. That is, the decoy polypeptide is administered once, twice, three times, four times, five times, six times, or more times a week at a physician's discretion. In some embodiments, individuals will be given at least 5 doses over a period of time. In other embodiments, individuals will be given greater than or fewer than 5 doses. Thus, in one embodiment, an individual will receive a dose of about 10 mg/kg of the decoy SIRP-gamma, SIRP-beta or SIRP-beta2 polypeptide every week. Alternatively, the individual will receive two doses of 5 mg/kg twice a week, or a daily 2 mg/kg dose over five days.

These dosage examples are not limiting and only used to exemplify particular dosing regimens for administering about 10 mg/kg of the decoy SIRP-gamma, SIRP-beta or SIRP-beta2 polypeptide. For instance, if the appropriate dose for a given situation is 10 mg/kg per week, the doses is optionally broken down into any number of permutations, e.g., four injections of 2.5 mg/kg per week. This also holds true if the appropriate dose for a particular situation is greater than or less than 10 mg/kg.

In some embodiments, the period of time that a decoy SIRP-gamma, SIRP-beta or SIRP-beta2 polypeptide (e.g., a composition comprising a variant SIRP-gamma, SIRP-beta or SIRP-beta2 polypeptide), is administered to the individual is any suitable period as determined by the stage of the disease, the patient's medical history and the attending physician's discretion. Examples of such suitable periods include, but are not limited to, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months, or at least about 24 months or longer. In particular aspects, the treatment period is continued for longer than 24 months, if desired, such as for 30 months, 31 months, 32 months, 33 months, 34 months, 35 months, 36 months, or longer than 36 months. In some embodiments, the period is 6 months, 1 year or 2 years.

In another embodiment, the period of time of dosing for any of the methods described herein is for at least about 2 weeks, at least about 4 weeks, at least about 8 weeks, at least about 16 weeks, at least about 17 weeks, at least about 18 weeks, at least about 19 weeks, at least about 20 weeks, at least about 24 weeks, at least about 28 weeks, at least about 32 weeks, at least about 36 weeks, at least about 40 weeks, at least about 44 weeks, at least about 48 weeks, at least about 52 weeks, at least about 60 weeks, at least about 68 weeks, at least about 72 weeks, at least about 80 weeks, at least about 88 weeks, at least about 96 weeks, or at least about 104 weeks.

In some embodiments, any decoy polypeptide described herein (e.g., a composition comprising a variant SIRP-gamma, SIRP-beta or SIRP-beta2 polypeptide), is administered in different phases of treatment. For example, the decoy SIRP-gamma, SIRP-beta or SIRP-beta2 polypeptide is administered in both a treatment phase and a maintenance phase. In some embodiments, the treatment phase will comprise administration of the decoy polypeptide formulation in weekly dosages, whereas the maintenance phase is for longer time periods, such as about every 6 weeks, about every 7 weeks, about every 8 weeks, about every 9 weeks, about every 10 weeks, about every 11 weeks, about every 12 weeks, or longer. In some cases, the dosage given in the treatment phase will be greater than the dosage given in the maintenance phase. However, treatment and maintenance phases are designed to a particular individual so the time and dosages between the treatment and maintenance phases vary from the above examples. Generally, the maintenance phase begins at any time deemed appropriate. For example, in some embodiments, the treatment phase will be eight weeks and the maintenance phase will continue throughout the individual's lifetime. In other embodiments, only a treatment or a maintenance phase will be undertaken.

In yet further embodiments, decoy polypeptide described herein (e.g., a composition comprising a variant SIRP-gamma, SIRP-beta or SIRP-beta2 polypeptide), is given prophylactically. In these embodiments, the administration of decoy polypeptide prevents onset of disease in an individual (e.g., an individual genetically pre-disposed to developing cancer, such as breast cancer; an individual predisposed to developing a bacterial or viral infection; an individual about to undergo an organ transplant; or an individual predisposed to developing anemia or autoimmune disease.)

The amount of time that an individual should remain on a decoy polypeptide described herein is determined by the attending physician. In some cases, it is advantageous to administer the decoy polypeptide for the rest of an individual's lifetime. In some of such embodiments, a decoy polypeptide is administered in four quadrants of the body, e.g., near lymph nodes, (e.g., in each armpit), in each buttock (e.g., subcutaneously) and the like. In some of such embodiments, a decoy polypeptide is administered via a pump. In some embodiments, a pump and/or delivery device is implanted in an individual to allow chronic dosing. Examples of implantable pumps include and are not limited to Alzet® osmotic pumps.

Kits

Provided herein are kits for dispensing the decoy polypeptides described herein. Such kits comprise a first drug product vial containing a decoy polypeptide comprising a SIRP-gamma, SIRP-beta or SIRP-beta2 polypeptide, and a second vial containing a suitable sterile liquid as described herein for reconstitution. In some embodiments For example, in one embodiment, such kits comprise a first vial, i.e., a drug product vial containing 300 µg of a decoy polypeptide comprising a SIRP-gamma, SIRP-beta or SIRP-beta2 polypeptide, which represents a 120% fill. This excess is intended to facilitate the withdrawal and administration of the specified dose. The kit further comprises a second vial containing up to 1 mL of 0.9% sodium chloride solution for injection. After reconstitution of the drug product with 0.6 mL of sodium chloride solution for injection (0.9% w/v), a drug product vial yields 0.5 mL for delivery corresponding to 250 µg of a decoy polypeptide comprising a SIRP-gamma, SIRP-beta or SIRP-beta2 polypeptide. By way of example, if the dose is 1 mg total, 4 vials are required per dose.

Certain Definitions

The terms "decoy," "inhibitor" and "blocking agent" as used herein refer to molecules that prevent binding of CD47 to its binding partner. For development purposes the binding may be performed under experimental conditions, e.g. using isolated proteins as binding partners, using portions of proteins as binding partners, using yeast display of proteins or portions of proteins as binding partners, and the like. For physiologically relevant purposes the binding of CD47 to its binding partner is often an event between two cells, where each cell expresses one of the binding partners. Of particular interest is the expression of SIRP polypeptides on phagocytic cells, such as macrophages; and the expression of CD47 on cells that could be targets for phagocytosis, e.g. tumor cells, circulating hematopoietic cells, and the like. Inhibitors may be identified using in vitro and in vivo assays for receptor or ligand binding or signaling.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" as used herein refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. The term "amino acid analogs" as used herein refers to compounds that have the same basic chemical structure as a naturally occurring amino acid, i.e., an .alpha. carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. The term "amino acid mimetics" as used herein refers to chemical compounds that have a structure that is different from the general chemical structure of an amino acid, but that functions in a manner similar to a naturally occurring amino acid.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and laboratory, zoo, sports, or pet animals, such as dogs, horses, cats, cows, sheep, goats, pigs, mice, rats, rabbits, guinea pigs, monkeys etc. In some embodiments, the mammal is human.

As used herein "cancer" includes any form of cancer, including but not limited to solid tumor cancers (e.g., lung, prostate, breast, bladder, colon, ovarian, pancreas, kidney, liver, glioblastoma, medulloblastoma, leiomyosarcoma, head & neck squamous cell carcinomas, melanomas, neuroendocrine; etc.) and liquid cancers (e.g., hematological cancers); carcinomas; soft tissue tumors; sarcomas; teratomas; melanomas; leukemias; lymphomas; and brain cancers, including minimal residual disease, and including both primary and metastatic tumors. Any cancer is a suitable cancer to be treated by the subject methods and compositions.

The term "binding partner" as used herein refers to a member of a specific binding pair (i.e., two molecules, usually two different molecules, where one of the molecules, e.g., a first binding partner, through non-covalent means specifically binds to the other molecule, e.g., a second binding partner).

As used herein, the terms "treatment," "treating," and the like, refer to administering an agent, or carrying out a procedure, for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of a tumor in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease. Treating may refer to any indicia of success in the treatment or amelioration or prevention of an cancer, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with cancer or other diseases. The term "therapeutic effect" refers to the reduction, elimination, or prevention of the disease, symptoms of the disease, or side effects of the disease in the subject.

"In combination with", "combination therapy" and "combination products" refer, in certain embodiments, to the concurrent administration to a patient of a first therapeutic and the compounds as used herein. When administered in combination, each component can be administered at the same time or sequentially in any order at different points in time. Thus, each component can be administered separately but sufficiently closely in time so as to provide the desired therapeutic effect.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means the amount that, when administered to a subject for treating a disease, is sufficient to effect treatment for that disease.

The term "antibody" is used in the broadest sense and specifically covers monoclonal antibodies (including full length monoclonal antibodies), polyclonal antibodies, multispecific antibodies (e.g., bispecific antibodies), peptibodies, human antibodies, humanized antibodies, camelid antibodies (including camelid single domain antibodies), alternative scaffold antibodies (e.g., affibodies, avimers, Fn3 domains, DARPins, Kunitz domains, SMIPs, Domain antibodies, BiTEs, Adnectins, Nanobodies, Stable scFvs, Anticalins) and antibody fragments so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity.

EXAMPLES

Example 1: Methods

Protein expression and purification. The human CD47 lgSF domain (residues 1-117), with a C15G mutation and C-terminal 8. histidine tag (SEQ ID NO: 40), were secreted from *Trichoplusia* in (Hi-5) cells using baculovirus and purified by Ni-NTA. Monomeric SIRP-gamma, SIRP-beta and SIRP-beta 2 variants were expressed as MBP-fusions in the periplasm of BL-21 (DE3) *E. coli* using a modified pMal-p2X expression vector (New England Biolabs) containing a rhinovirus 3C protease cleavage site after the MBP tag and a C-terminal 8× histidine tag (SEQ ID NO: 40). Cells were induced at an OD-600 of 0.8 with 1 mM IPTG and incubated with shaking at 22° C. for 24 hours. Periplasmic protein was obtained by osmotic shock and the MBP-fusion proteins purified using nickel-nitrilotriacetic acid (Ni-NTA) chromatography. Eluted proteins were digested with 3C protease at 4° C. for 12 hours to remove MBP and further purified by an additional Ni-NTA chromatography step. Endotoxin was removed using Triton X-114 as previously described and endotoxin removal confirmed using the ToxinSensor Chromogenic LAL Endotoxin Assay Kit (Genscript). SIRP-gamma, SIRP-beta and SIRP-beta2-Fc fusions were produced by cloning SIRP-gamma, SIRP-beta and SIRP-beta2 variants into a modified pFUSE-hlgG4-Fc vector (lnvivogen) with an IL-2 signal sequence and engineered Ser228 Pro mutation. Proteins were expressed by transient transfection in Freestyle 293-F cells (Invitrogen) and purified over HiTrap Protein A columns (GE Healthcare).

Biotinylated proteins were obtained by expression with a carboxy-terminal biotin acceptor peptide tag (GLN-DIFEAQKIEWHE (SEQ ID NO: 41)) and purified as described above. The purified proteins were biotinylated in vitro with BirA ligase and then repurified from the reaction mixture by Ni-NTA chromatography.

Yeast Display and Library Generation of SIRP-Gamma, SIRP-Beta or SIRP-Beta2 Variants.

The N-terminal V-set domains of SIRP-gamma, SIRP-beta or SIRP-beta2 were displayed on the surface of *S. cerevisiae* strain BJ5465 in the pYDS649HM vector as described. The libraries were generated by assembly PCR reactions that randomized the CD47-contact residues and the hydrophobic 'core' residues of SIRP-gamma, SIRP-beta or SIRP-beta2 using the primer sets with degenerate codons. The PCRs were further amplified with primers containing homology to the pYDS649HM vector, combined with linearized pYDS649HM vector DNA, and co-electroporated into BJ5465 yeast. The resulting libraries contained 4.0-8.0×$10^8$ transformants.

Selection of Library.

Transformed yeast were expanded in SD-W liquid media at 30° C. and induced in SG-W liquid medium at 20° C. All media were supplemented with 100 mM maltose to prevent flocculation. All selection steps were carried out at 4° C. For the first round of selection, 8×$10^9$ induced yeast, representing ten-fold coverage of the number of library transformants, were resuspended in 5 ml PBE (phosphate buffered saline supplemented with 0.5% bovine serum albumin and 0.5 mM EDTA). Yeast were mixed with 500 µl paramagnetic streptavidin microbeads (Miltenyi) that are pre-coated with biotinylated CD47 and the mixture was incubated with rotation for one hour. The yeast were pelleted by centrifugation at 5,000×g for five minutes and washed twice with 1 ml PBE. Magnetically-labeled yeast were resuspended in 5 ml PBE and separated with an LS MAGS column according to the manufacturer's instructions (Miltenyi). Eluted yeast were pelleted, resuspended in SD-W medium, and expanded for the next round of selection. Additional rounds of selection were performed similarly to the first round with the following modifications: 1×$10^8$ yeast were resuspended in 500 µl PBE containing Alexa Fluor 488-labeled anti-HA antibody (Cell Signaling) or successively decreasing concentrations of biotinylated CD47 protein, from 100 nM to 1 nM. After incubation for one hour, yeast were washed with PBE and for selections with CD47, labeled with streptavidin-PE (Invitrogen) or streptavidin-Alexa Fluor 647 (produced in house) for 15 minutes. Yeast were washed twice more with PBE and magnetically labeled with 50 µl of the appropriate anti-fluorophore microbeads (anti-FITC, anti-PE, or anti-Alexa Fluor 647; Miltenyi) for 15 minutes. Yeast were washed once, resuspended in 3 ml PBE, and separated with an LS column as in the first round.

For the final rounds of selection, kinetic selection was performed. Briefly, yeast were stained with 10 nM biotinylated CD47 for one hour, washed with PBE, and then resuspended in 500 µl PBE containing 1 µM nonbiotinylated CD47. The cells were incubated at 25° C. for 300 minutes, after which they were washed with ice-cold PBE and stained with fluorescently labeled streptavidin. Yeast were then co-labeled with Alexa Fluor 488 labeled anti-HA and streptavidin-Alexa Fluor 647 and selected with FACS cell sorter.

Surface Plasmon Resonance (SPR).

Experiments were conducted with a Biacore T100 at 25° C. Protein concentrations were quantified by 280 nm absorbance with a Nanodrop2000 spectrometer (Thermo Scientific). A Biacore SA sensor chip (GE Healthcare) was used to capture biotinylated CD47 ($R_{max}$ ~150 RU). An unrelated biotinylated protein was immobilized with an RU value matching that of the reference surface to control for non-specific binding. Measurements were made with serial dilutions of the SIRP-gamma, SIRP-beta or SIRP-beta2 variants in HBS-P+ buffer (GE Healthcare). The CD47 surface was regenerated by three 60 second injections of 2 M $MgCl_2$. All data were analyzed with the Biacore T100 evaluation software version 2.0 with a 1:1 Langmuir binding model.

Cell Lines and GFP-Luciferase+ Transduction.

DLD-1 cells (ATCC), HT-29 cells (ATCC), Raji cells (ATCC), Jurkat cells (ATCC), and 639-V cells (DSMZ) were cultured in RPMI+GlutaMax (Invitrogen) supplemented with 10% fetal bovine serum (Omega Scientific), 100 U/ml penicillin and 100 µg/ml streptomycin (Invitrogen). GFP-luciferase+ lines were generated by transduction using a pCDH-CMV-MCS-EF1 puro HIV-based lentiviral vector (Systems Biosciences) engineered to express an eGFP-luciferase2 (pg14) fusion protein. Stable lines were created by sorting for GFP expression on a FACS cell sorter.

Cell-Based CD47 Binding Assays.

Varying concentrations of biotinylated SIRP-gamma, SIRP-beta or SIRP-beta2 monomers, SIRP-gamma, SIRP-beta or SIRP-beta2-hIgG4 fusion proteins were incubated with cancer cells. Binding of biotinylated monomers was detected using 100 nM Alexa Fluor 647-conjugated streptavidin as a secondary staining reagent and is analyzed on an Accuri C6 flow cytometer (BD Biosciences). Binding of SIRP-gamma, SIRP-beta or SIRP-beta2-hIgG4 fusion proteins or antiCD47 antibodies is detected with goat anti-human IgG antibody (Invitrogen) and is analyzed on an Accuri C6 flow cytometer. Data represent the mean fluorescence intensity normalized to maximal binding for each class of reagents, and points are fit to sigmoidal dose-response curves using Prism 5 (Graphpad).

Cell-Based CD47 Blocking Assays.

Biotinylated SIRP-gamma, SIRP-beta or SIRP-beta2 variants were incubated with Alexa Fluor 647-conjugated streptavidin to form SIRP-gamma, SIRP-beta or SIRP-beta2 variant tetramers. 100 nM SIRP-gamma, SIRP-beta or SIRP-beta2 variant tetramers were combined with titrating concentrations of CD47 antagonists and simultaneously added to 50,000 GFP-luciferase+ Raji cells. Cells were incubated for 30 min at 4° C. then washed to remove unbound tetramer. Samples were stained with DAPI (Sigma) to exclude dead cells, and fluorescence was assayed using an Accuri C6 flow cytometer. Data represent the geometric mean fluorescence intensity normalized to maximal tetramer binding, and were fit to sigmoidal dose response curves using Prism 5 (Graphpad).

Macrophage Derivation and Phagocytosis Assays.

Leukocyte reduction system (LRS) chambers were obtained from anonymous donors, and peripheral blood mononuclear cells were enriched by density gradient centrifugation over Ficoll-Paque Premium (GE Healthcare). Monocytes were purified on an AutoMACS (Miltenyi) using anti-CD14 microbeads (Miltenyi) and differentiated to macrophages by culture for 7-10 days in IMDM+GlutaMax (Invitrogen) supplemented with 10% AB-Human Serum (Invitrogen) and 100 U/ml penicilin and 100 µg/ml streptomycin (Invitrogen). Phagocytosis assays were performed by co-culture of 50,000 macrophages with 100,000 GFP+ tumor cells for 2 hours, then analyzed using an LSRFortessa cell analyzer with high throughput sampler (BD Biosciences). Antibodies used for treatment include: mouse IgG1 isotype control (eBioscience), anti-CD47 clone 203 (eBioscience), anti-EpCam (Biolegend), cetuximab (Bristol-Myers Squibb), and rituximab (Genentech). Macrophages were identified by flow cytometry using anti-CD14, anti-CD45, or anti-CD206 antibodies (Biolegend). Dead cells were excluded from the analysis by staining with DAPI (Sigma). Phagocytosis was evaluated as the percentage of GFP+ macrophages and was normalized to the maximal response by each independent donor against each cell line. Statistical significance was determined by 2-way ANOVA with Bonferroni post-tests, and, when indicated, data were fit to sigmoidal dose response curves using Prism 5 (Graphpad).

FACS-Based Phagocytosis Assay.

Assessment of phagocytosis was performed by co-culture of 100,000 target cells and 50,000 macrophages for two hours in ultra-low attachment 96 well U-bottom plates (Corning) in IMDM+GlutaMax (Life Technologies) without antibiotics or serum added. Macrophages were generated by magnetic bead-based purification of primary human monocytes using the CD14+ Whole Blood isolation kit (Miltenyi) followed by 7 days of culture with human serum (Gemini); on day 7, these cells were harvested from plates using TrypLE Express (Life Technologies). Macrophages were marked with Calcein AM red/orange cell stain (Life Technologies) according to manufacturer indications. Target cells were engineered to stably express green fluorescent protein. Protein treatments were added to co-culture of target cells and macrophages, and the mix was incubated at 37° C. for 2 hours. Reactions were run on an LSRFortessa Analyzer outfitted with a high-throughput auto-sampler (BD Biosciences). Phagocytosis was evaluated as GFP+ macrophages expressed as a percentage of the total macrophages, as analyzed using FlowJo v.9.4.10 (Tree Star) and was normalized as indicated in the figure legends.

Mice.

Nod.Cg-Prkdc$^{scid}$ IL2rg$_{tm1Wjl}$/SzJ (NSG) mice were used for all in vivo experiments. Mice are engrafted with tumors at approximately 6-10 weeks of age, and experiments are performed with age and sex-matched cohorts of 8-15 mice.

Tumor Models.

To model human colon cancer, $1 \times 10^5$ GFP-luciferase+ DLD-1 cells were injected into the peritoneal cavities of NSG mice. Bladder cancer is modeled by engraftment of $1.25 \times 10^5$ GFP-luciferase+639-V cells into the dorsal subcutaneous tissue of NSG mice in 25% Matrigel (BD Biosciences). $1 \times 10^6$ GFP-luciferase+ Raji cells are engrafted subcutaneously on the lower flank for a localized model of human lymphoma. In all models, treatment is initiated upon confirmation of engraftment and continued as indicated. For all treatments, 200 μg SIRP-gamma, SIRP-beta or SIRP-beta2 variant or antibody is administered by intraperitoneal injection on a daily schedule. Tumor growth is monitored by bioluminescence imaging, and tumor dimensions are measured to calculate volumes according to the ellipsoid formula ($\pi/6 \times \text{length} \times \text{width}^2$). Statistical significance is determined by Mann-Whitney test or Kruskai-Wallis with Dunn's post-tests as appropriate. Survival is analyzed by Mantel-Cox test.

Bioluminescence Imaging.

Anesthetized mice are injected with 200 μl D-luciferin (firefly) potassium salt (Biosynth) reconstituted at 16.67 mg/ml in sterile PBS. Bioluminescence imaging is performed using an IVIS Spectrum (Caliper Life Sciences) over 20 minutes to record maximal radiance. Peak total flux values are assessed from the anatomical region of interest using Living Image 4.0 (Caliper Life Sciences) and used for analysis.

Protein sequences. Among the proteins used in the examples described herein, the following are included:

```
Wild-type SIRPgamma:
                                       (SEQ ID NO: 1)
EEELQMIQPEKLLLVTVGKTATLHCTVTSLLPVGPVLWFRGVGPGRELIY

NQKEGHFPRVTTVSDLTKRNNMDFSIRISSITPADVGTYYCVKFRKGSPE

NVEFKSGPGTEMALGAKPS

GV1 (high affinity SIRPgamma):
                                       (SEQ ID NO: 3)
EEELQIIQPEKLLLVTVGKTATLHCTITSLFPVGPVLWFRGVGPGRVLIY
```

NQRQGPFPRVTTVSDTTKRNNMDFSIRISSITPADVGTYYCIKFRKGSPE

NVEFKSGPGTEMALGAKPS

```
GV1.2:
                                      (SEQ ID NO: 13)
EEELQIIQPEKLLLVTVGKTATLHCTITSLFPVGPIQWFRGVGPGRVLIY

NQREGPFPRVTTVSDGTKRNNMDFSIRISSITPADVGTYYCVKFRKGSPE

DVEFKSGPGTEMALGAKPS

HGV1:
                                       (SEQ ID NO: 4)
EEELQIIQPEKLLLVTVGKTATLHCTITSLFPVGPIQWFRGVGPGRVLIY

NQRDGPFPRVTTVSDGTKRNNMDFSIRISSITPADVGTYYCVKFRKGTPE

DVEFKSGPGTEMALGAKPS

HGV2:
                                       (SEQ ID NO: 5)
EEELQIIQPEKLLLVTVGKTATLHCTITSLFPVGPIQWFRGVGPGRVLIY

NQKDGPFPRVTTVSDGTKRNNMDFSIRISSITPADVGTYYCVKFRKGSPE

DVEFKSGPGTEMALGAKPS

HGV3:
                                       (SEQ ID NO: 6)
EEELQIIQPEKLLLVTVGKTATLHCTITSLFPVGPIQWFRGVGPGRVLIY

NQKDGHFPRVTTVSDGTKRNNMDFSIRISSITPADVGTYYCVKFRKGSPE

DVEFKSGPGTEMALGAKPS

MGV1:
                                       (SEQ ID NO: 7)
EEELQIIQPEKLLLVTVGKTATLHCTITSLFPVGPIQWFRGAGPGRVLIY

NQRDGPFPRVTTVSDGTKRNNMDFSIRISSITPADVGTYYCIKFRKGTPE

DVEFKSGPGTEMALGAKPS
```

| SIRP-gamma library residues: | |
|---|---|
| M6 | MILF |
| V27 | FILV |
| L30 | LIVHND |
| L31 | FILV |
| V33 | VILPTA |
| V36 | VI |
| L37 | LQ |
| V42 | VA |
| E47 | EV |
| Q52 | QPLVAE |
| K53 | KR |
| E54 | EDKNQH |
| H56 | HPR |
| L66 | LIVPTARSG |
| T67 | TINFSYVAD |
| V92 | VI |
| S98 | SRNKTIM |
| N101 | NKDEHQ |

```
Wild-type SIRPbeta:
                                      (SEQ ID NO: 43)
EDELQVIQPEKSVSVAAGESATLRCAMTSLIPVGPIMWFRGAGAGRELIY

NQKEGHFPRVTTVSELTKRNNLDFSISISNITPADAGTYYCVKFRKGSPD

DVEFKSGAGTELSVRAKPS
```

BVI (high affinity SIRPbeta):
(SEQ ID NO: 26)
EDELQIIQPEKSVSVAAGESATLRCAITSLFPVGPIQWFRGAGAGRVLIY

NQRQGPFPRVTTVSETTKRNNLDFSISISNITPADAGTYYCIKFRKGSPD

DVEFKSGAGTELSVRAKPS

Wild-type SIRPbeta2:
(SEQ ID NO: 44)
EEELQVIQPDKSISVAAGESATLHCTVTSLIPVGPIQWFRGAGPGRELIY

NQKEGHFPRVTTVSDLTKRNNMDFSIRISNITPADAGTYYCVKFRKGSPD

HVEFKSGAGTELSVRAKPS

B2V1 (high affinity SIRPbeta2):
(SEQ ID NO: 28)
EEELQIIQPDKSISVAAGESATLHCTITSLFPVGPIQWFRGAGPGRVLIY

NQRQGPFPRVTTVSDTTKRNNMDFSIRISNITPADAGTYYCIKFRKGSPD

DVEFKSGAGTELSVRAKPS

Additional protein sequences for SIRP-gamma polypeptide include:

HLib1:
(SEQ ID NO: 8)
EEELQIIQPEKLLLVTVGKTATLHCTITSHFPVGPIQWFRGVGPGRVLIYNQKDGHFPRVTTVSDGTKR

NNMDFSIRISSITPADVGTYYCVKFRKGSPEDVEFKSGPGTEMALGAKPS;

HLib2:
(SEQ ID NO: 9)
EEELQIIQPDKSVLVAAGETATLRCTITSLFPVGPIQWFRGAGPGRVLIYNQRDGPFPRVTTVSDGTKR

NNMDFSIRISSITPADVGTYYCVKFRKGTPEDVEFKSGPGTEMALGAKPS;

HLib3:
(SEQ ID NO: 10)
EEELQIIQPEKLLLVTVGKTATLHCTITSLFPVGPVLWFRGVGPGRVLIYNQRQGPFPRVTTVSDTTKR

NNMDFSIRISSITPADVGTYYCVKFRKGTPEDVEFKSGPGTEMALGAKPS;

HLib4:
(SEQ ID NO: 11)
EEELQIIQPEKLLLVTVGKTATLHCTITSLFPVGPIQWFRGVGPGRELIYNAREGRFPRVTTVSDLTKR

NNMDFSIRISSITPADVGTYYCVKFRKGSPEDVEFKSGPGTEMALGAKPS;

HMLib1:
(SEQ ID NO: 12)
EEELQIIQPDKSVLVAAGETATLRCTITSLFPVGPIQWFRGAGPGRVLIYNQRQGPFPRVTTVSDTTKR

NNMDFSIRIGNITPADAGTYYCIKFRKGSPDDVEFKSGAGTELSVRAKPS;

HMLib2:
(SEQ ID NO: 3)
EEELQIIQPEKLLLVTVGKTATLHCTITSLFPVGPVLWFRGVGPGRVLIYNQRQGPFPRVTTVSDTTKR

NNMDFSIRISSITPADVGTYYCIKFRKGSPENVEFKSGPGTEMALGAKPS;

HMLib3:
(SEQ ID NO: 13)
EEELQIIQPEKLLLVTVGKTATLHCTITSLFPVGPIQWFRGVGPGRVLIYNQREGPFPRVTTVSDGTKR

NNMDFSIRISSITPADVGTYYCVKFRKGSPEDVEFKSGPGTEMALGAKPS;

HMLib4:
(SEQ ID NO: 42)
EEELQMIQPEKLLLVTVGKTATLHCTVTSLLPVGPVLWFRGVGPGRELIYNQKEGHFPRVTTVSDLT

KRNNMDFSIRISSITPADVGTYYCVKFRKGSPENVEFKSGPGTEMALGAKPS;

HMLib5:
(SEQ ID NO: 14)
EEELQIIQPDKSVLVAAGETATLRCTITSLFPVGPIQWFRGAGPGRVLIYNQRDGPFPRVTTVSDGTKR

NNMDFSIRISSITPADVGTYYCIKFRKGIPEDVEFKSGPGTEMALGAKPS;

HMLib6:
(SEQ ID NO: 15)
EEELQIIQPDKSVLVAAGETATLRCTITSLFPVGPIQWFRGAGPGRVLIYNQRDGPFPRVTTVSDGTKR

NNMDFSIRISSITPADVGTYYCIKFRKGIPEDVEFKSGPGTXWH,
wherein X is A, R, N, D, C, Q, E, G, H, I, L, K, M, F. P, S, T, W, Y, or V;

HMLib7:
(SEQ ID NO: 16)
EEELQIIQPDKSVLVAAGETATLRCTITSLFPVGPIQWFRGAGPGRVLIYNQKDGPFPRVTTVSDGTKR

NNMDFSIRISSITPADVGTYYCIKFRKGTPEDVEFKSGPGTEMALGAKPS;

MLib1:
(SEQ ID NO: 17)
EEELQIIQPEKLLLVTVGKTATLHCTITSLLPVGPIQWFRGVGPGRELIYNQRDGPFPRVTTVSDGTKR

NNMDFSIRISSITPADVGTYYCVKFRKGTPEDVEFKSGPGTEMALGAKPS;

MLib2:
(SEQ ID NO: 18)
EEELQIIQPEKLLLVTVGKTATLHCTLTSLLPVGPILWFRGVGPGRVLIYNQRDGPFPRVTTVSDGTKR

NNMDFSIRISSITPADVGTYYCVKFRKGNPEDVEFKSGPGTEMALGAKPS;

MLib3:
(SEQ ID NO: 19)
EEELQLIQPEKLLLVTVGKTATLHCTITSLFPPGPIQWFRGVGPGRVLIYNQKDGPFPRVTTVSDGTKR

NNMDFSIRISSITPADVGTYYCVKFRKGIPEDVEFKSGPGTEMALGAKPS;

MLib4:
(SEQ ID NO: 20)
EEELQIIQPEKLLLVTVGKTATLRCTITSLFPVGPIQWFRGAGPGRVLIYNQRDGPFPRVTTVSDGTKR

NNMDFSIRISSITPADVGTYYCIKFRKGIPEDVEFKSGPGTEMALGAKPS;

MLib5:
(SEQ ID NO: 21)
EEELQIIQPEKLLLVTVGKTATLHCTITSLFPIGPILWFRGVGPGRVLIYNQKDGPFPRVTTVSDGTKRN

NMDFSIRISSITPADVGTYYCVKFRKGSPEDVEFKSGPGTEMALGAKPS;

MLib6:
(SEQ ID NO: 22)
EEELQMIQPEKLLLVTVGKTATLHCTITSLFPVGPIQWFRGAGPGRVLIYNQRDGPFPRVTTVSDGTK

RNNMDFSIRISSITPADVGTYYCIKFRKGIPEDVEFKSGPGTEMALGAKPS;

MLib7:
(SEQ ID NO: 23)
EEELQIIQPDKSVLVAAGETATLRCTITSLFPVGPIQWFRGVGPGRVLIYNQKDGPFPRVTTVSDGTKR

NNMDFSIRISSITPADVGTYYCIKFRKGIPEDVEFKSGPGTEMALGAKPS;
and

MLib8:
(SEQ ID NO: 24)
EEELQIIQPDKSVLVAAGETATLRCTITSLFPVGPIQWFRGAGPGRVLIYNQKDGPFPRVTTVSDGTKR

NNMDFSIRISSITPADVGTYYCIKFRKGTPEDVEFKSGPGTEMALXAKPS.

In additional embodiments, the decoy polypeptide is a fusion or chimeric polypeptide. In additional embodiments, the decoy polypeptide comprises a SIRP-gamma polypeptide sequence fused to a polypeptide sequence comprising an immune checkpoint inhibitor, a co-stimulatory molecule, or a cytokine or an attenuated cytokine, wherein the sequences are connected by a Gly-Ser linker of varying length and composition. In further embodiments, the decoy polypeptide comprises one of the following sequences:

1) Fusion to immune checkpoint inhibitors
a. PD-1/PD-L1 antagonist
Example: HAC-GV3 (high-affinity PD-1 decoy fused to GV3)

(SEQ ID NO: 30)
DSPDRPWNPPTFSPALLVVTEGDNATFTCSFSNTSESFHVVWHRESPSGQ

TDTLAAFPEDRSQPGQDARFRVTQLPNGRDFHMSVVRARRNDSGTYVCGV

ISLAPKIQIKESLRAELRVTERGGGGSGGGGSEEELQIIQPEKLLLVTVG

KTATLHCTITSLFPVGPIQWFRGVGPGRVLIYNQKDGHFPRVTTVSDGTK

RNNMDFSIRISSITPADVGTYYCVKFRKGSPEDVEFKSGPGTEMALGAKP

S;

b. BTLA/CD160 antagonist
Example: GV3-BTLA decoy (SEQ ID NO: 31)
EEELQIIQPEKLLLVTVGKTATLHCTITSLFPVGPIQWFRGVGPGRVLIY

NQKDGHFPRVTTVSDGTKRNNMDFSIRISSITPADVGTYYCVKFRKGSPE

DVEFKSGPGTEMALGAKPSGGGGSGGGGSWNIHGKESCDVQLYIKRQSEH

SILAGDPFELECPVKYCANRPHVTWCKLNGTTCVKLEDRQTSWKEEKNIS

FFILHFEPVLPNDNGSYRCSANFQSNLIESHSTTLYVTDVK;

c. Phosphatidylserine antagonist
Example: GV3-MFGE8 decoy

```
                                                   (SEQ ID NO: 32)
EEELQIIQPEKLLLVTVGKTATLHCTITSLFPVGPIQWFRGVGPGRVLIY

NQKDGHFPRVTTVSDGTKRNNMDFSIRISSITPADVGTYYCVKFRKGSPE

DVEFKSGPGTEMALGAKPSGGGGSGGGGSELNGCANPLGLKNNSIPDKQI

TASSSYKTWGLHLFSWNPSYARLDKQGNFNAWVAGSYGNDQWLQVDLGSS

KEVTGIITQGARNFGSVQFVASYKVAYSNDSANWTEYQDPRTGSSKIFPG

NWDNHSHKKNLFETPILARYVRILPVAWHNRIALRLELLGC;
```

Example: GV3-Tim1 decoy

```
                                                   (SEQ ID NO: 33)
EEELQIIQPEKLLLVTVGKTATLHCTITSLFPVGPIQWFRGVGPGRVLIY

NQKDGHFPRVTTVSDGTKRNNMDFSIRISSITPADVGTYYCVKFRKGSPE

DVEFKSGPGTEMALGAKPSGGGGSGGGGSVAGSVKVGGEAGPSVTLPCHY

SGAVTSMCWNRGSCSLFTCQNGIVWTNGTHVTYRKDTRYKLLGDLSRRDV

SLTIENTAVSDSGVYCCRVEHRGWFNDMKITVSLEIVPPKVTT;
```

Example: GV3-Tim3 decoy

```
                                                   (SEQ ID NO: 34)
EEELQIIQPEKLLLVTVGKTATLHCTITSLFPVGPIQWFRGVGPGRVLIY

NQKDGHFPRVTTVSDGTKRNNMDFSIRISSITPADVGTYYCVKFRKGSPE

DVEFKSGPGTEMALGAKPSGGGGSGGGGSSEVEYRAEVGQNAYLPCFYTP

AAPGNLVPVCWGKGACPVFECGNVVLRTDERDVNYWTSRYWLNGDFRKGD

VSLTIENVTLADSGIYCCRIQIPGIMNDEKFNLKLVIKPAKVTPA;
```

Example: GV3-Tim4 decoy

```
                                                   (SEQ ID NO: 35)
EEELQIIQPEKLLLVTVGKTATLHCTITSLFPVGPIQWFRGVGPGRVLIY

NQKDGHFPRVTTVSDGTKRNNMDFSIRISSITPADVGTYYCVKFRKGSPE

DVEFKSGPGTEMALGAKPSGGGGSGGGGSTSETVVTEVLGHRVTLPCLYS

SWSHNSNSMCWGKDQCPYSGCKEALIRTDGMRVTSRKSAKYRLQGTIPRG

DVSLTILNPSESDSGVYCCRIEVPGWFNDVKINVRLNLQRASTTTDEKFN

LKLVIKPAKVTPA;
```

2) Fusion to co-stimulatory molecules
a. CD40 agonist
Example: GV3-CD40L

```
                                                   (SEQ ID NO: 36)
EEELQIIQPEKLLLVTVGKTATLHCTITSLFPVGPIQWFRGVGPGRVLIY

NQKDGHFPRVTTVSDGTKRNNMDFSIRISSITPADVGTYYCVKFRKGSPE

DVEFKSGPGTEMALGAKPSGGGGSGGGGSGDQNPQIAAHVISEASSKTTS

VLQWAEKGYYTMSNNLVTLENGKQLTVKRQGLYYIYAQVTFCSNREASSQ

APFIASLCLKSPGRFERILLRAANTHSSAKPCGQQSIHLGGVFELQPGAS

VFVNVTDPSQVSHGTGFTSFGLLKL;
``` b. 41BB (CD137) agonist
Example: GV3-41BBL

```
                                                   (SEQ ID NO: 37)
EEELQIIQPEKLLLVTVGKTATLHCTITSLFPVGPIQWFRGVGPGRVLIY

NQKDGHFPRVTTVSDGTKRNNMDFSIRISSITPADVGTYYCVKFRKGSPE

DVEFKSGPGTEMALGAKPSGGGGSGGGGSDPAGLLDLRQGMFAQLVAQNV

LLIDGPLSWYSDPGLAGVSLTGGLSYKEDTKELVVAKAGVYYVFFQMELR

RVVAGEGSGSVSLALHLMPLRSAAGAAALALTVDLPPASSEARNSAFGFQ

GRLLHLSAGQRLGVHLHTEARARHAWQLTQGATVLGLFRVTPEIPA;
```

3) Fusion to cytokines or attenuated cytokines
Example: GV3-IL2

```
                                                   (SEQ ID NO: 38)
EEELQIIQPEKLLLVTVGKTATLHCTITSLFPVGPIQWFRGVGPGRVLIY

NQKDGHFPRVTTVSDGTKRNNMDFSIRISSITPADVGTYYCVKFRKGSPE

DVEFKSGPGTEMALGAKPSGGGGSGGGGSAPTSSSTKKTQLQLEHLLLDL

QMILNGINNYKNPKLTRMLTFKFYMPKKATELKHLQCLEEELKPLEEVLN

LAQSKNFHLRPRDLISNINVIVLELKGSETTFMCEYADETATIVEFLNRW

ITFCQSIISTLT;
```

Example: GV3-IL2 (an "attenuated" cytokine with mutations F42A/D20T)

```
                                                   (SEQ ID NO: 39)
EEELQIIQPEKLLLVTVGKTATLHCTITSLFPVGPIQWFRGVGPGRVLIY

NQKDGHFPRVTTVSDGTKRNNMDFSIRISSITPADVGTYYCVKFRKGSPE

DVEFKSGPGTEMALGAKPSGGGGSGGGGSAPTSSSTKKTQLQLEHLLLTL

QMILNGINNYKNPKLTRMLTAKFYMPKKATELKHLQCLEEELKPLEEVLN

LAQSKNFHLRPRDLISNINVIVLELKGSETTFMCEYADETATIVEFLNRW

ITFCQSIISTLT.
```

Example 2: Surface Plasmon Resonance-Based
Measurement of Binding Affinity and Kinetics of
the SIRP-Gamma Variant GV3 for Human CD47

Using the surface plasmon resonance method described above, one could measure the binding affinity and kinetics of the SIRP-gamma variant GV3 for human CD47. For example, as shown in FIG. 1A, varying concentrations of the SIRP-gamma variant GV3 was used, including 100 pM, 316 pM, 1 nM, 3.16 nM, 10 nM, and 100 nM, in binding reactions with a known concentration of biotinylated human CD47. Using a 1:1 Langmuir binding model, the calculated dissociation constant $K_d$ was 92 pM. The calculated dissociation half-life $T_{1/2}$ was about 44 minutes. FIG. 1B shows a graphic representation of a biotinylated human CD47 bound to the SIRP-gamma variant GV3.

Example 3: Surface Plasmon Resonance-Based
Measurement of Binding Affinity and Kinetics of
HAC-GV3, a Fusion Protein of the SIRP-Gamma
Variant GV3 and a High-Affinity PD-1 Variant
HAC, for Human CD47

Using the surface plasmon resonance method described above, one could measure the binding affinity and kinetics of HAC-GV3, a fusion protein of the SIRP-gamma variant GV3 and a high-affinity PD-1 variant HAC, for human CD47. For example, as shown in FIG. 2A, varying concentrations of the HAC-GV3 fusion protein was used, including 100 pM, 316 pM, 1 nM, 3.16 nM, 10 nM, and 100 nM, in binding reactions with a known concentration of biotinylated human CD47. Using a 1:1 Langmuir binding model, the calculated dissociation constant $K_d$ was 160 pM. The calculated dissociation half-life $T_{1/2}$ was about 40 minutes. FIG. 2B shows a graphic representation of a biotinylated human CD47 bound to the fusion protein comprising SIRP-gamma variant GV3 and HAC.

Example 4: Surface Plasmon Resonance-Based Measurement of Binding Affinity and Kinetics of a PD-1 Variant HAC for Human PD-L1

In another example, surface plasmon resonance was used to measure the binding affinity and kinetics of PD-1 variant HAC for human PD-L1. Varying concentrations of HAC, including 100 pM, 316 pM, 1 nM, 3.16 nM, 10 nM, and 100 nM, were used in binding reactions with a known concentration of biotinylated human PD-L1. Using a 1:1 Langmuir binding model, the calculated dissociation constant $K_d$ was 110 pM. The calculated dissociation half-life $T_{1/2}$ was about 42 minutes.

Example 5: Surface Plasmon Resonance-Based Measurement of Binding Affinity and Kinetics of HAC-GV3, a Fusion of the SIRP-Gamma Variant GV3 with a PD-1 Variant HAC, for Human PD-L1

Using the surface plasmon resonance method described above, one could measure the binding affinity and kinetics of HAC-GV3, a fusion of the SIRP-gamma variant GV3 with a PD-1 variant HAC, for human PD-L1. For example, as shown in FIG. 3A, varying concentrations of the HAC-GV3 fusion protein, including 100 pM, 316 pM, 1 nM, 3.16 nM, 10 nM, and 100 nM, were added to binding reactions with a known concentration of biotinylated human PD-L1. Using a 1:1 Langmuir binding model, the calculated dissociation constant $K_d$ was 134 pM. The calculated dissociation half-life $T_{1/2}$ was about 38 minutes. FIG. 3B shows a graphic representation of a biotinylated human PD-L1 bound to HAC-GV3.

Example 6: Surface Plasmon Resonance-Based Measurement of the Simultaneous Binding of Both Human CD47 and Human PD-L1 by HAC-GV3

In another example of surface plasmon resonance-based measurement, the binding affinity and kinetics of simultaneous binding of both human CD47 and human PD-L1 by HAC-GV3 were measured by adding varying concentrations of either HGV3 or HAC-GV3 to a known concentration of biotinylated human CD47. As shown in FIG. 4A, in comparison to human GV3 alone, the binding curve for fusion protein HAC-GV3 showed two distinct peaks—a first peak for binding to biotinylated CD47 and a second peak for binding to PD-L1. FIG. 4B shows a graphic representation of a biotinylated human CD47 bound to the GV3 portion of the HAC-GV3 fusion protein, wherein the HAC portion is bound to PD-L1.

Example 7: Flow Cytometry-Based Measurement of Blockade of CD47/SIRP-Alpha Interactions on the Surface of CD47+ Cells by GV3 and HAC-GV3

Using the cell-based CD47 blocking assay described above, 50 nM of biotinylated SIRP-alpha tetramers were combined with titrating concentrations of either GV3 or HAC-GV3 in the presence of the CD47+ cells. FIG. 5 shows the flow cytometry-based measurement of blockade of CD47/SIRP-alpha interactions on the surface of CD47+ GFP-luciferase+ DLD1-Tg cells by GV3 and HAC-GV3. Percent median fluorescence intensity (% MFT) as a readout of SIRP-alpha binding is plotted against log concentration in M.

Example 8: Flow Cytometry-Based Measurement of Blockade of CD47/SIRP-Alpha Interactions on the Surface of CD47+ PD-L1+ Cells by GV3 and HAC-GV3

Figure 6:
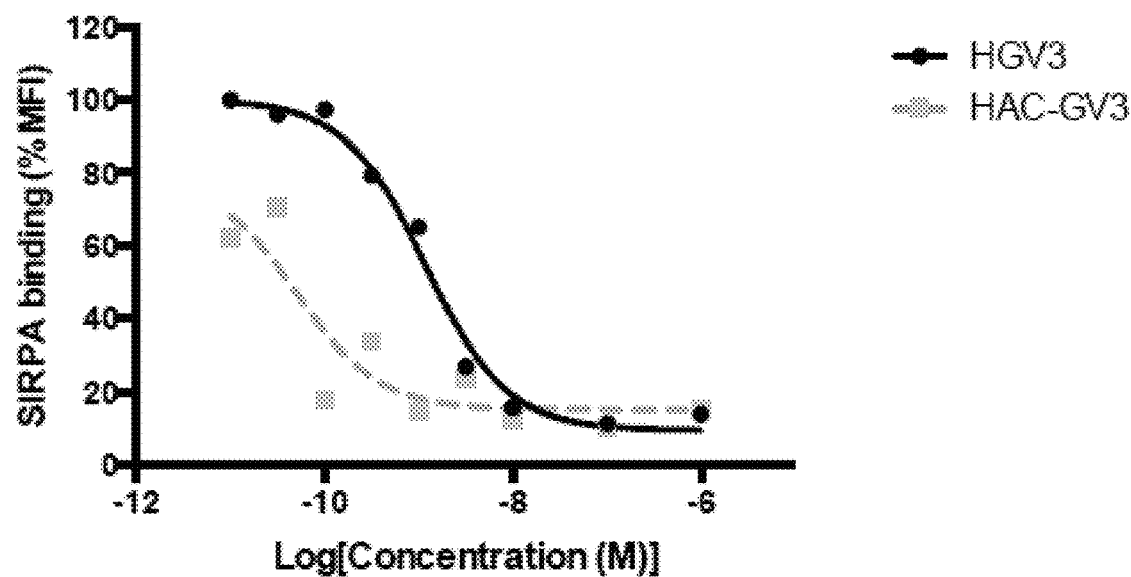
FIG. 6 shows the flow cytometry-based measurement of blockade of CD47/SIRP-alpha interactions on the surface of CD47+ PD-L1+ GFP-luciferase+ DLD1-Tg cells by GV3 and HAC-GV3. 50 nM of biotinylated SIRP-alpha tetramers were combined with titrating concentrations of either GV3 or HAC-GV3 in the presence of the CD47+ PD-L1+ cells. Percent median fluorescence intensity (% MFI) as a readout of SIRP-alpha binding is plotted against log concentration in M.

In another example of the cell-based CD47 blocking assay described above, flow cytometry was used to measure blockade of CD47/SIRP-alpha interactions on the surface of CD47+ PD-L1+ GFP-luciferase+ DLD1-Tg cells by GV3 and HAC-GV3. As FIG. 6 shows, 50 nM of biotinylated SIRP-alpha tetramers were combined with titrating concentrations of either GV3 or HAC-GV3 in the presence of the CD47+ PD-L1+ cells. Percent median fluorescence intensity (% MFT) as a readout of SIRP-alpha binding is plotted against log concentration in M.

Example 9: Flow Cytometry-Based Measurement of Blockade of PD-1/PD-L1 Interactions on the Surface of PD-L1+ Cells by HAC and HAC-GV3

Figure 7:
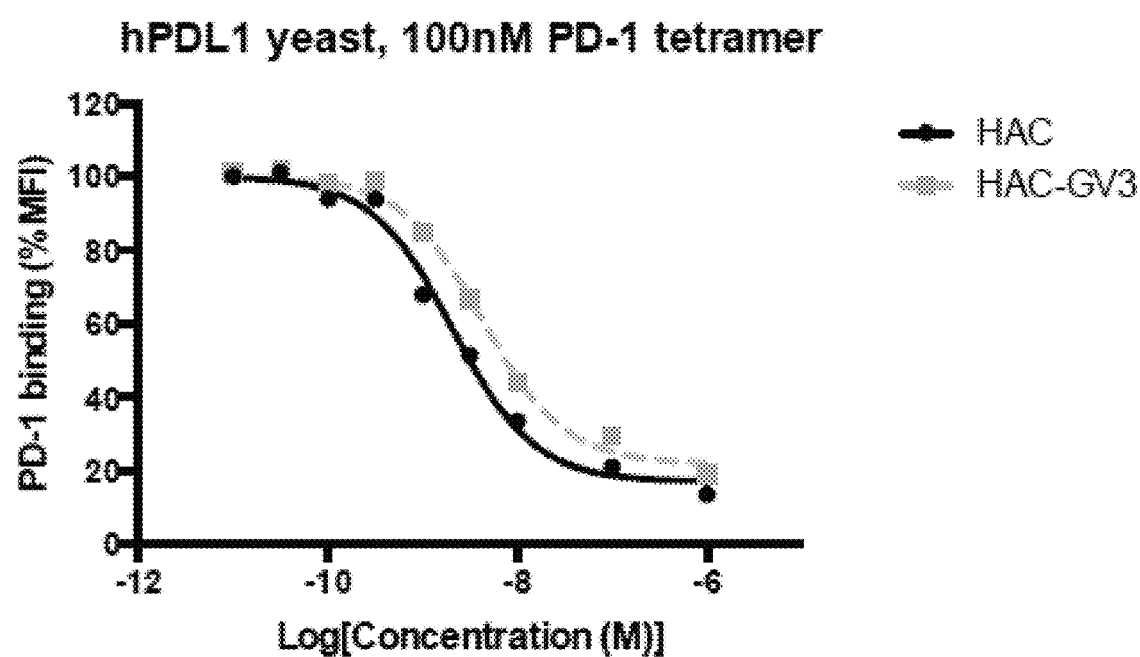
FIG. 7 shows the flow cytometry-based measurement of blockade of PD-1/PD-L1 interactions on the surface of human PD-L1+ yeast cells by HAC and HAC-GV3. 100 nM of biotinylated PD-1 tetramers were combined with titrating concentrations of either HAC or HAC-GV3 in the presence of the hPD-L1+ yeast cells. Percent median fluorescence intensity (% MFI) as a readout of PD-1 binding is plotted against log concentration in M.

In another example of cell-based CD47 blocking assay, flow cytometry was used to measure blockade of PD-1/PD-L1 interactions on the surface of human PD-L1+ yeast cells by HAC and HAC-GV3. As FIG. 7 shows, 100 nM of biotinylated PD-1 tetramers were combined with titrating concentrations of either HAC or HAC-GV3 in the presence of hPD-L1+ yeast cells. Percent median fluorescence intensity (% MFT) as a readout of PD-1 binding is plotted against log concentration in M.

Example 10: Flow Cytometry-Based Measurement of Blockade of PD-1/PD-L1 Interactions on the Surface of CD47+ PD-L1+ Cells by HAC and HAC-GV3

Figure 8:
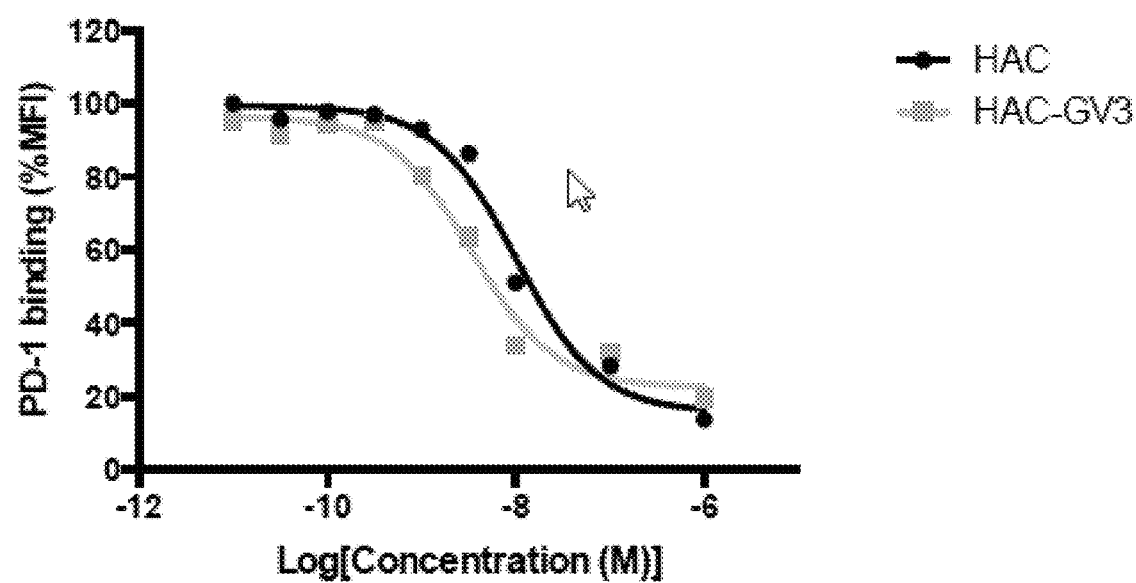
FIG. 8 shows the flow cytometry-based measurement of blockade of PD-1/PD-L1 interactions on the surface of CD47+ PD-L1+ GFP-luciferase+ DLD1-Tg cells by HAC and HAC-GV3. 100 nM of biotinylated PD-1 tetramers were combined with titrating concentrations of either HAC or HAC-GV3 in the presence of the CD47+ PD-L1+ cells. Percent median fluorescence intensity (% MFI) as a readout of PD-1 binding is plotted against log concentration in M.

In another example of cell-based CD47 blocking assay, flow cytometry was used to measure of blockade of PD-1/PD-L1 interactions on the surface of CD47+ PD-L1+ GFP-luciferase+ DLD1-Tg cells by HAC and HAC-GV3. As shown in FIG. 8, 100 nM of biotinylated PD-1 tetramers were combined with titrating concentrations of either HAC or HAC-GV3 in the presence of the CD47+ PD-L1+ cells. Percent median fluorescence intensity (% MFT) as a readout of PD-1 binding is plotted against log concentration in M.

Figure 9:
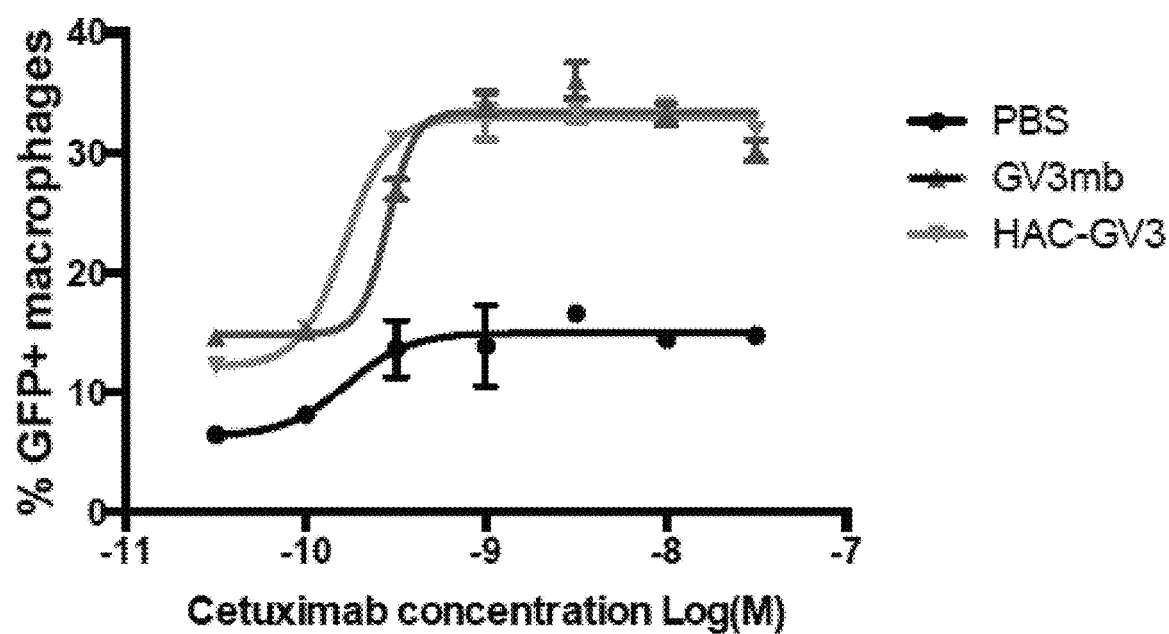
FIG. 9 shows the FACS-based measurement of phagocytosis by donor-derived human macrophages against the human colon cancer cell line DLD1, indicating that GV3 microbody and HAC-GV3 potentiate phagocytosis across a wide range of opsonizing antibody concentrations. Assessment of phagocytosis was performed by co-culture of 100,000 target cells and 50,000 macrophages for two hours in ultra-low attachment 96 well U-bottom plates (Corning) in IMDM+GlutaMax (Life Technologies) without antibiotics or serum added. Macrophages were generated by magnetic bead-based purification of primary human monocytes using the CD14+ Whole Blood isolation kit (Miltenyi) followed by 7 days of culture with human serum (Gemini); on day 7, these cells were harvested from plates using TrypLE Express (Life Technologies). Macrophages were marked with Calcein AM red/orange cell stain (Life Technologies) according to manufacturer indications. Target cells were engineered to stably express green fluorescent protein. A dimerized microbody form of HGV3 (GV3mb) or HAC-GV3 fusion protein was added to reaction wells at a saturating concentration of 10 nM, while the opsonizing antibody Cetuximab was titrated across three logs of concentration. Error bars represent the standard deviation of duplicate experiments. Reactions were run on an LSRFortessa Analyzer outfitted with a high-throughput auto-sampler (BD Biosciences). Phagocytosis was evaluated as GFP+ macrophages expressed as a percentage of the total macrophages, as analyzed using FlowJo v.9.4.10 (Tree Star) and was normalized as indicated in the figure legends.

Example 11: FACS-Based Measurement of Phagocytosis Shows GV3 Microbody and HAC-GV3 Potentiate Phagocytosis Across a Wide Range of Opsonizing Antibody Concentrations FIG. 9 shows the FACS-based measurement of phagocytosis by donor-derived human macrophages against the human colon cancer cell line DLD1, indicating that GV3 microbody and HAC-GV3 potentiate phagocytosis across a wide range of opsonizing antibody concentrations. Assessment of phagocytosis was performed by co-culture of 100,000 target cells and 50,000 macrophages for two hours in ultra-low attachment 96 well U-bottom plates (Corning) in IMDM+GlutaMax (Life Technologies) without antibiotics or serum added. Macrophages were generated by magnetic bead-based purification of primary human monocytes using the CD14+ Whole Blood isolation kit (Miltenyi) followed by 7 days of culture with human serum (Gemini); on day 7, these cells were harvested from plates using TrypLE Express (Life Technologies). Macrophages were marked with Calcein AM red/orange cell stain (Life Technologies) according to manufacturer indications. Target cells were engineered to stably express green fluorescent protein. A dimerized microbody form of HGV3 (GV3mb) or HAC-GV3 fusion protein was added to reaction wells at a saturating concentration of 10 nM, while the opsonizing antibody Cetuximab was titrated across three logs of concentration. Error bars represent the standard deviation of duplicate experiments. Reactions were run on an LSRFortessa Analyzer outfitted with a high-throughput auto-sampler (BD Biosciences). Phagocytosis was evaluated as GFP+ macrophages expressed as a percentage of the total macrophages, as analyzed using FlowJo v.9.4.10 (Tree Star) and was normalized as indicated in the figure legends.

Example 12: Occupancy and Persistence of HAC-GV3 and GV3

Figure 10:
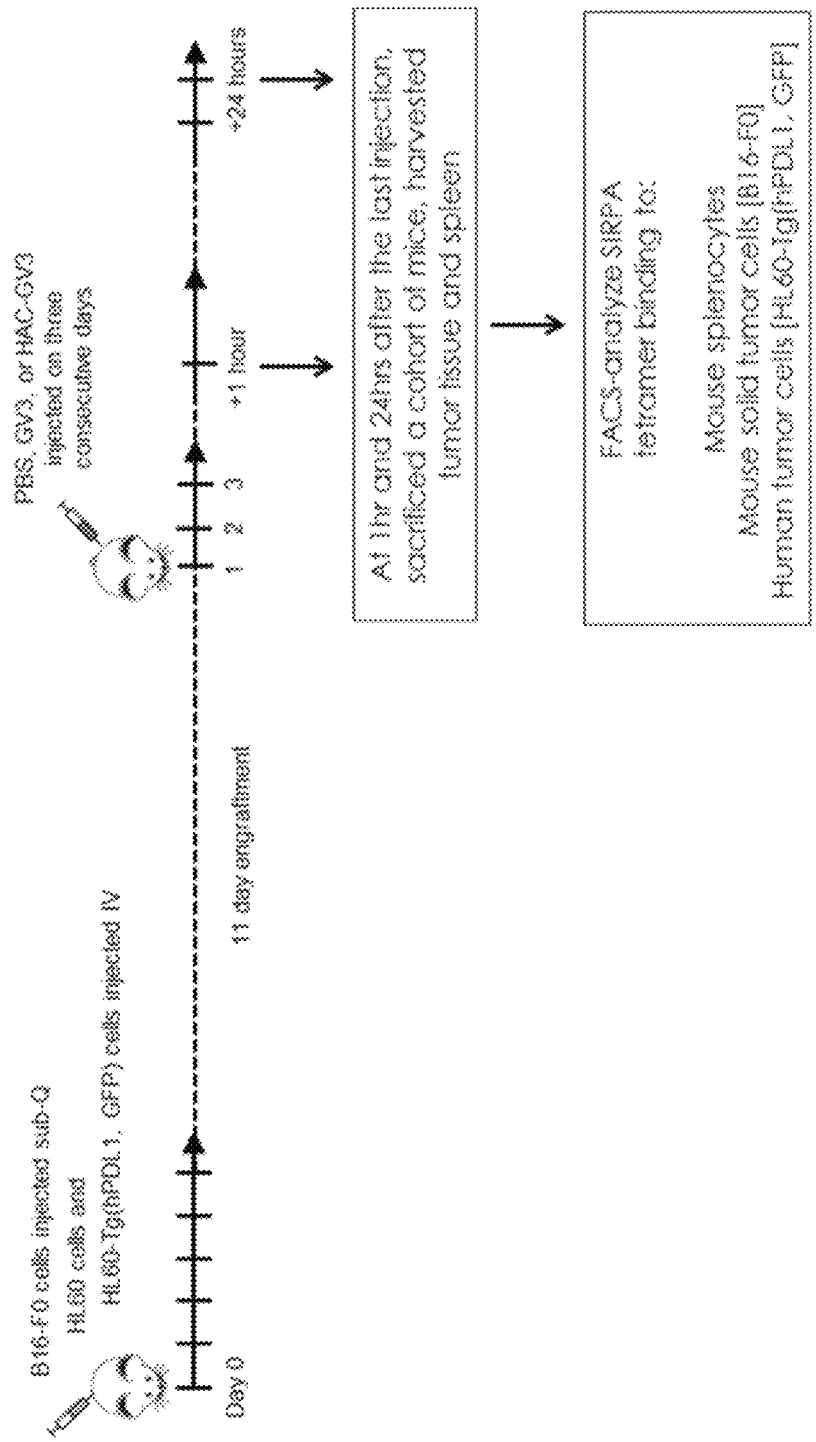
FIG. 10 shows the experimental outline for NSG mice engrafted with human leukemia cells enable approximation of human RO kinetics in vivo

The experiments to determine occupancy and persistence of HAC-GV3 and GV3 are summarized in FIG. 10. To test occupancy and persistence of HAC-GV3 and GV3 NSG mice were injected on day 0 with B16-F0 (subcutaneously), as well as a mixture of unmodified HL60 and HL60-Tg (hPDL1, GFP) (intravenously). On days 11, 12, and 13, mice were injected with PBS, GV3, or HAC-GV3. One hour or 24 hours after the last injection, spleens or tumors were harvested from sacrificed mice and cells were dissociated into single cell suspensions on ice without the use of enzymatic digestion. FACS was used to analyze SIRPA-tetramer binding to either mouse splenocytes, mouse solid tumor cells (B16F0), or Human tumor cells (HL60-Tg (hPDL1, GFP)).

Figure 11A:
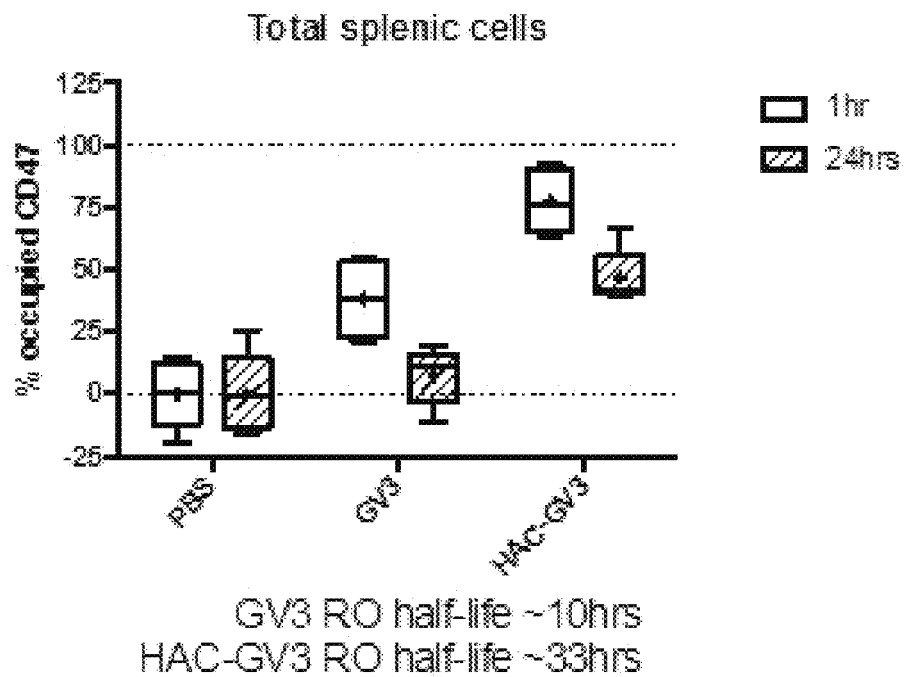
FIGS. 11A-D show HAC-GV3 achieves superior receptor occupancy and persistence in tissue as compared to GV3.
Figure 11B:
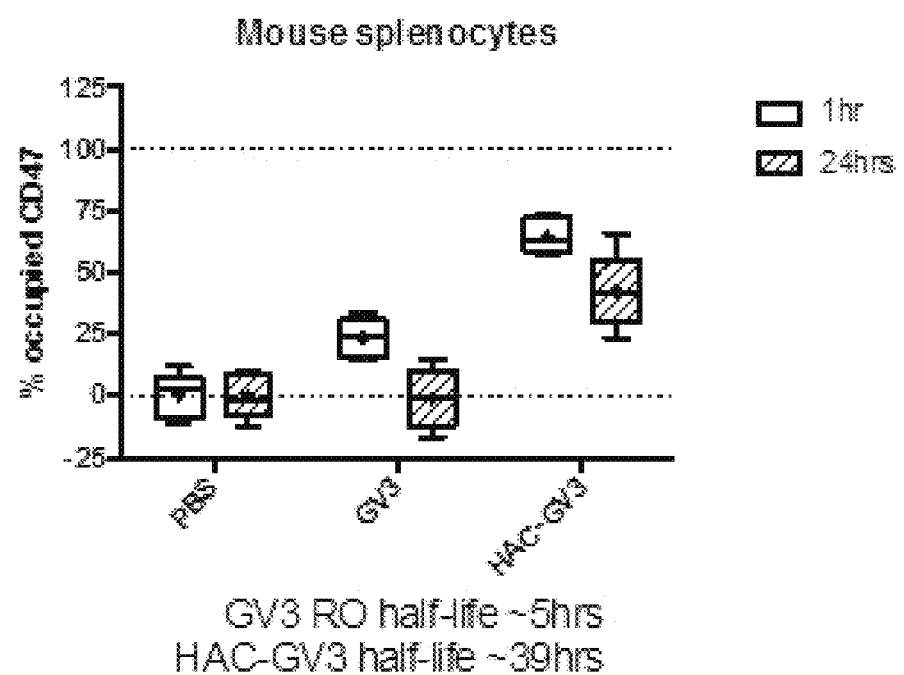
Figure 11C:
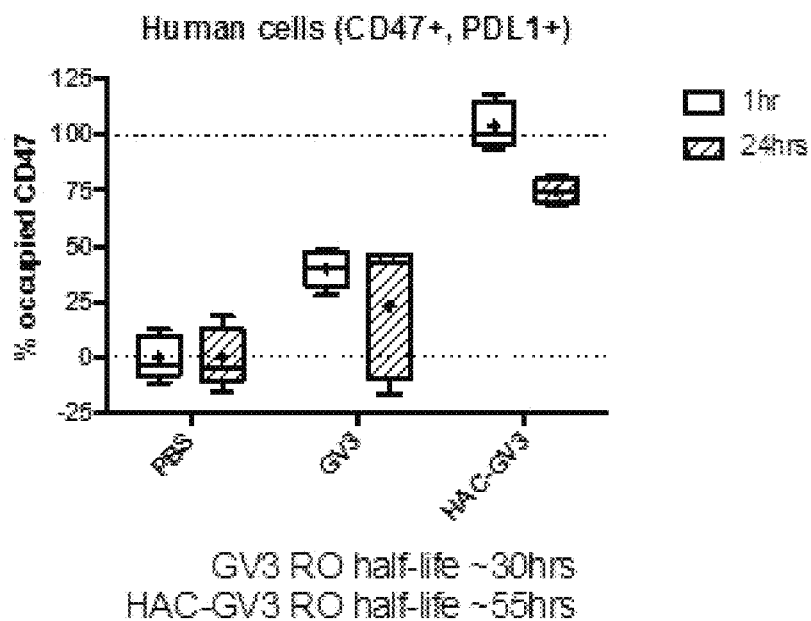
Figure 11D:
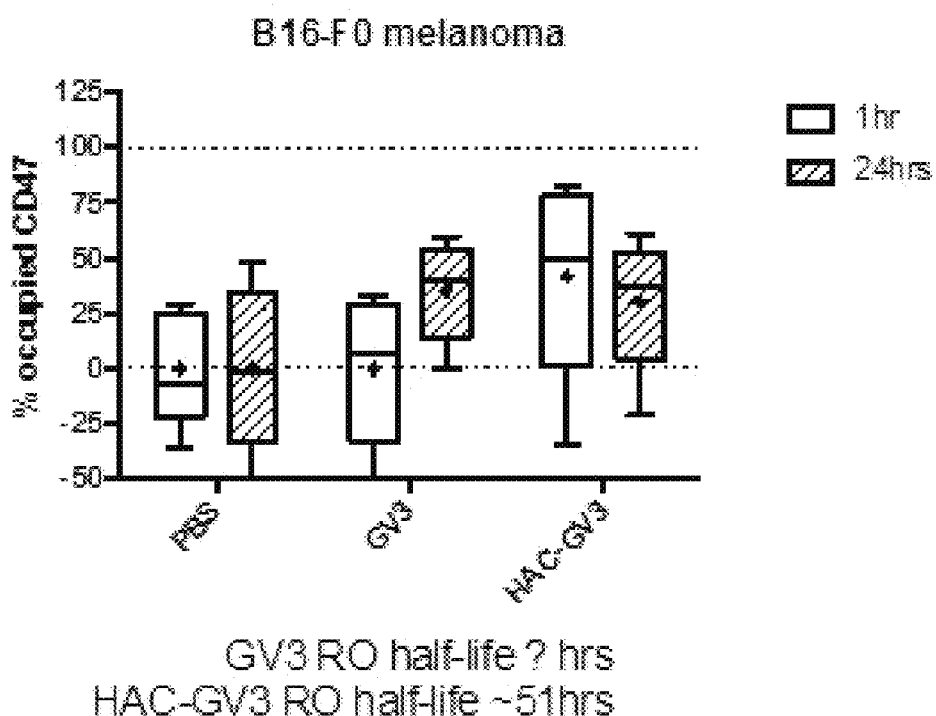

Occupancy and persistence of HAC-GV3 and GV3 are shown in FIGS. 11A-11D. HAC-GV3 was shown to have both increased occupancy and persistence compared to GV3 and PBS control in total splenic cells at 1 hour and 24 hours (FIG. 11A). HAC-GV3 was demonstrated to have both increased occupancy and persistence compared to GV3 and PBS control in mouse splenocytes at 1 hour and 24 hours (FIG. 11B). HAC-GV3 was observed to have both increased occupancy and persistence compared to GV3 and PBS control in human cells isolated from the spleen at 1 hour and 24 hours (FIG. 11C). HAC-GV3 was demonstrated to have increased occupancy compared to GV3 and PBS control at 1 hour and 24 hours in B16-F0 melanoma cells isolated from a tumor (FIG. 11D).

Example 13: Clinical Trial to Test Effect of a Decoy Polypeptide for Treatment of B Cell Lymphoma This is a prospective open label, controlled, randomized study to test the safety and efficacy of a decoy polypeptide for the treatment of patients with stage IIIB or stage IV B cell lymphoma. To be eligible, patients entering the trial will have demonstrated either stable disease or a clinical response after first-line treatment (chemotherapy alone, or chemotherapy and radiotherapy) and have an ECOG performance status of 0, 1 or 2. Following a 3 week washout period, patients will be stratified by disease status, and randomized to either anti-CD20 antibody (e.g. rituximab) alone, or anti-CD20 antibody plus decoy polypeptide.

Eight weekly subcutaneous treatments with 10 mg/kg of a decoy polypeptide will be administered at weeks 0, 1, 2, 3, 4, 5, 6 and 7. All patients will be additionally treated with 375 mg/m$^2$ anti-CD20 at week 0, and 500 mg/m$^2$ anti-CD20 at week 1, 2, 3, 4, 5, 6, and 7.

Primary outcome measures will be documentation of safety profile of the decoy polypeptide, and comparison of survival rate of patients in the two arms of the trial. Secondary outcome measures will be to measure activation of phagocytosis elicited by the decoy polypeptide, and to evaluate quality of life for patients undergoing immunotherapy.

Example 14: Clinical Trial to Test Maximum Tolerated Dose and/or Recommended Dosage of Decoy Polypeptide in Patients with Advanced Solid Tumors This is an open label, Phase I dose escalation study to evaluate the safety and immunogenicity of repeat dose vaccination with a decoy polypeptide in patients with previously treated Stage 3 or 4 solid tumors, including but not limited to: breast, non-small cell lung, ovarian, colorectal, gastric, prostate, pancreatic, and renal cell cancers.

Part 1 evaluates escalating dose levels of the decoy polypeptide administered subcutaneously once every other week (Q2W) over 8 weeks (for a total of 4 doses) or once every week (QW) over 8 weeks (for a total of 8 doses), and uses a 3+3 dose escalation design to identify the maximum tolerated dose (MTD) and/or recommended dose (RD) for each dosing schedule, for further evaluation in Part 2 of the study. Part 2 evaluates the safety, immunogenicity, and potential anti-tumor activity of the decoy polypeptide of Example 1 administered over 8 weeks at the Q2W and QW MTD/RD in cohorts of 15 patients each. After the 8 week administration period, patients are evaluated for safety, immune response and tumor response to Week 20.

The study population includes patients with previously treated Stage 3 or 4 solid tumors.

Inclusion criteria:

18-70 years of age at time of consent

Life expectancy of at least 6 months, according to investigator's opinion

Have histologically confirmed breast, non-small cell lung, ovarian, colorectal, gastric, prostate, pancreatic, or renal cell cancer, or other tumor type Have evidence of persistent, recurrent, or progressive disease after at least one course of systemic therapy for locally advanced or metastatic disease, including chemotherapy, targeted therapy, or immunotherapy Clinical stage 3 or 4 disease ECOG 0 or 1

Adequate hematological, renal and hepatic function parameters

Exclusion criteria:

Has received treatment with any systemic chemotherapy, radiation, or experimental agent within 4 weeks of study drug dosing Has any preexisting medical condition requiring chronic steroid or immunosuppressive therapy HIV, hepatitis B or hepatitis C positive Mode of Administration: The decoy polypeptide is administered subcutaneously, starting on Day 1 per cohort assignment. All patients receive doses of the decoy polypeptide administered as four separate injections at four separate injection sites (one injection each in the right upper arm or thigh, left upper arm or thigh, and right and left lower abdomen). The starting dose is 0.01 mg/kg of the decoy polypeptide. The dose levels are selected using a dose-doubling design. An intermediate dose level, 750 mg/kg, is considered when the MTD is less than 1000 mg/kg.

In the Part 2 evaluation and assessment of the eight week administration, measures include measurement of activation of phagocytosis. Tumor response is assessed as defined by RECIST or Immune RECIST 1.1.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A polypeptide comprising a SIRP-gamma polypeptide consisting of the sequence EEELQX$_1$IQPEKLLLVTVGKTATLHCTX$_2$TSX$_3$X$_4$PX$_5$GPX$_6$X$_7$W-FRGX$_8$GPGRX$_9$LIYNX$_{10}$X$_{11}$X$_{12}$GX$_{13}$FPRVTTVSDX$_{14}$-X$_{15}$KRNNMDFSIRISSITPADVGTYYCX$_{16}$KFRKGX$_{17}$-PEX$_{18}$VEFK SGPGTEMALGAKPS (SEQ ID NO: 2), wherein X$_1$ is M, I, L or F; X$_2$ is F, I, or L; X$_3$ is L, I, V, H, N or D; X$_4$ is F, I, L or V; X$_5$ is V, I, L, P, T or A; X$_6$ is V or I; X$_7$ is L or Q; X$_8$ is V or A; X$_9$ is E or V; X$_{10}$ is Q, P, L, V, A or E; X$_{11}$ is K or R; X$_{12}$ is E, D, K, N, Q or H; X$_{13}$ is H, P or R; X$_{14}$ is L, I, V, P, T, A, R, S or G; X$_{15}$ is T, I, N, F, S, Y, V, A or D; X$_{16}$ is V or I; X$_{17}$ is S, R, N, K, T, I or M; and X$_{18}$ is N, K, D, E, H or Q, and wherein the SIRP-gamma polypeptide binds CD47.

2. The polypeptide of claim 1, wherein the SIRP-gamma polypeptide comprises a sequence selected from one of

```
                                           (SEQ ID NO: 3)
EEELQIIQPEKLLLVTVGKTATLHCTITSLFPVGPVLWFRGVGPGRVLIY

NQRQGPFPRVTTVSDTTKRNNMDFSIRISSITPADVGTYYCIKFRKGSPE

NVEFKSGPGTEMALGAKPS;

(SEQ ID NO: 4)
EEELQIIQPEKLLLVTVGKTATLHCTITSLFPVGPIQWFRGVGPGRVLIY

NQRDGPFPRVTTVSDGTKRNNMDFSIRISSITPADVGTYYCVKFRKGTPE

DVEFKSGPGTEMALGAKPS;

(SEQ ID NO: 5)
EEELQIIQPEKLLLVTVGKTATLHCTITSLFPVGPIQWFRGVGPGRVLIY

NQKDGPFPRVTTVSDGTKRNNMDFSIRISSITPADVGTYYCVKFRKGSPE

DVEFKSGPGTEMALGAKPS;

(SEQ ID NO: 6)
EEELQIIQPEKLLLVTVGKTATLHCTITSLFPVGPIQWFRGVGPGRVLIY

NQKDGHFPRVTTVSDGTKRNNMDFSIRISSITPADVGTYYCVKFRKGSPE

DVEFKSGPGTEMALGAKPS;
and (SEQ ID NO: 7)
EEELQIIQPEKLLLVTVGKTATLHCTITSLFPVGPIQWFRGAGPGRVLIY

NQRDGPFPRVTTVSDGTKRNNMDFSIRISSITPADVGTYYCIKFRKGTPE

DVEFKSGPGTEMALGAKPS.
```

3. The polypeptide of claim 1, wherein the polypeptide blocks binding of CD47 to a ligand.

4. The polypeptide of claim 3, wherein the ligand is SIRP-alpha, SIRP-gamma, or thrombospondin-1.

5. The polypeptide of claim 1, wherein the polypeptide binds to a cell which expresses CD47.

6. The polypeptide of claim 5, wherein the cell is a tumor cell, virally infected cell, bacterially infected cell, damaged red blood cell, arterial plaque cell, fibrotic tissue cell, a healthy normal cell such as hematopoietic stem cell, a healthy myeloid or lymphoid precursor cell, or a healthy differentiated hematopoietic cell type such as T, B, plasma, or NK cell.

7. The polypeptide of claim 1, wherein the polypeptide further comprises an opsonizing antibody to enable phagocytosis or ADCC of a cell expressing CD47, wherein the cell is a tumor cell, virally infected cell, bacterially infected cell, damaged red blood cell, arterial plaque cell, fibrotic tissue cell, healthy normal cell such as hematopoietic stem cell, healthy myeloid or lymphoid precursor cell or healthy differentiated hematopoietic cell type such as T, B, plasma, or NK cells.

8. The polypeptide of claim 1, wherein the SIRP-gamma polypeptide is multimeric.

9. The polypeptide of claim 1, wherein the SIRP-gamma polypeptide is monomeric.

10. The polypeptide of claim 1, wherein the polypeptide further comprises a detectable label.

11. The polypeptide of claim 1, wherein the polypeptide has increased occupancy relative to a wildtype SIRP-gamma.

12. The polypeptide of claim 1, wherein the polypeptide has increased persistence relative to a wildtype SIRP-gamma.

13. The polypeptide of claim 1, wherein the SIRP-gamma polypeptide comprises the sequence EEELQIIQPEKLLL-VTVGKTATLHCTITSLFPVGPIQWFRGVGPGRVLIYN-QREGPFPRVTT VSDGTKRNNMDFSIRISSITPADVG-TYYCVKFRKGSPEDVEFKSGPGTEMALGAKPS (SEQ ID NO: 13).

14. The polypeptide of claim 1, wherein the SIRP-gamma polypeptide comprises one of the following sequences:

(SEQ ID NO: 8)
EEELQIIQPEKLLLVTVGKTATLHCTITSHFPVGPIQWFRGVGPGRVLIYNQKDGHFPRVTTVSDGTKR
NNMDFSIRISSITPADVGTYYCVKFRKGSPEDVEFKSGPGTEMALGAKPS;

(SEQ ID NO: 9)
EEELQIIQPDKSVLVAAGETATLRCTITSLFPVGPIQWFRGAGPGRVLIYNQRDGPFPRVTTVSDGTKR
NNMDFSIRISSITPADVGTYYCVKFRKGTPEDVEFKSGPGTEMALGAKPS;

(SEQ ID NO: 10)
EEELQIIQPEKLLLVTVGKTATLHCTITSLFPVGPVLWFRGVGPGRVLIYNQRQGPFPRVTTVSDTTKR
NNMDFSIRISSITPADVGTYYCVKFRKGTPEDVEFKSGPGTEMALGAKPS;

(SEQ ID NO: 11)
EEELQIIQPEKLLLVTVGKTATLHCTITSLFPVGPIQWFRGVGPGRELIYNAREGRFPRVTTVSDLTKR
NNMDFSIRISSITPADVGTYYCVKFRKGSPEDVEFKSGPGTEMALGAKPS;

(SEQ ID NO: 12)
EEELQIIQPDKSVLVAAGETATLRCTITSLFPVGPIQWFRGAGPGRVLIYNQRQGPFPRVTTVSDTTKR
NNMDFSIRIGNITPADAGTYYCIKFRKGSPDDVEFKSGAGTELSVRAKPS;

(SEQ ID NO: 3)
EEELQIIQPDKSVLVAAGETATLRCTITSLFPVGPVLWFRGVGPGRVLIYNQRQGPFPRVTTVSDTTKR
NNMDFSIRISSITPADVGTYYCIKFRKGSPENVEFKSGPGTEMALGAKPS;

(SEQ ID NO: 13)
EEELQIIQPEKLLLVTVGKTATLHCTITSLFPVGPIQWFRGVGPGRVLIYNQREGPFPRVTTVSDGTKR
NNMDFSIRISSITPADVGTYYCVKFRKGSPEDVEFKSGPGTEMALGAKPS;

(SEQ ID NO: 42)
EEELQMIQPEKLLLVTVGKTATLHCTVTSLLPVGPVLWFRGVGPGRELIYNQKEGHFPRVTTVSDLT
KRNNMDFSIRISSITPADVGTYYCVKFRKGSPENVEFKSGPGTEMALGAKPS;

(SEQ ID NO: 14)
EEELQIIQPDKSVLVAAGETATLRCTITSLFPVGPIQWFRGAGPGRVLIYNQRDGPFPRVTTVSDGTKR
NNMDFSIRISSITPADVGTYYCIKFRKGIPEDVEFKSGPGTEMALGAKPS;

(SEQ ID NO: 15)
EEELQIIQPDKSVLVAAGETATLRCTITSLFPVGPIQWFRGAGPGRVLIYNQRDGPFPRVTTVSDGTKR
NNMDFSIRISSITPADVGTYYCIKFRKGIPEDVEFKSGPGTXWH,
wherein X is A, R, N, D, C, Q, E, G, H, I, L, K, M, F. P, S, T, W, Y, or V;

(SEQ ID NO: 16)
EEELQIIQPDKSVLVAAGETATLRCTITSLFPVGPIQWFRGAGPGRVLIYNQKDGPFPRVTTVSDGTKR
NNMDFSIRISSITPADVGTYYCIKFRKGTPEDVEFKSGPGTEMALGAKPS;

(SEQ ID NO: 17)
EEELQIIQPEKLLLVTVGKTATLHCTITSLLPVGPIQWFRGVGPGRELIYNQRDGPFPRVTTVSDGTKR
NNMDFSIRISSITPADVGTYYCVKFRKGTPEDVEFKSGPGTEMALGAKPS;

(SEQ ID NO: 18)
EEELQIIQPEKLLLVTVGKTATLHCTLTSLLPVGPILWFRGVGPGRVLIYNQRDGPFPRVTTVSDGTKR
NNMDFSIRISSITPADVGTYYCVKFRKGNPEDVEFKSGPGTEMALGAKPS;

(SEQ ID NO: 19)
EEELQLIQPEKLLLVTVGKTATLHCTITSLFPPGPIQWFRGVGPGRVLIYNQKDGPFPRVTTVSDGTKR
NNMDFSIRISSITPADVGTYYCVKFRKGIPEDVEFKSGPGTEMALGAKPS;

(SEQ ID NO: 20)
EEELQIIQPEKLLLVTVGKTATLRCTITSLFPVGPIQWFRGAGPGRVLIYNQRDGPFPRVTTVSDGTKR
NNMDFSIRISSITPADVGTYYCIKFRKGIPEDVEFKSGPGTEMALGAKPS;

(SEQ ID NO: 21)
EEELQIIQPEKLLLVTVGKTATLHCTITSLFPIGPILWFRGVGPGRVLIYNQKDGPFPRVTTVSDGTKRN
NMDFSIRISSITPADVGTYYCVKFRKGSPEDVEFKSGPGTEMALGAKPS;

```
                                                          (SEQ ID NO: 22)
EEELQMIQPEKLLLVTVGKTATLHCTITSLFPVGPIQWFRGAGPGRVLIYNQRDGPFPRVTTVSDGTK

RNNMDFSIRISSITPADVGTYYCIKFRKGIPEDVEFKSGPGTEMALGAKPS.
```

15. The polypeptide of claim 1, wherein the SIRP-gamma polypeptide is a fusion or chimeric polypeptide, and wherein the SIRP-gamma polypeptide is fused to a polypeptide sequence comprising an immune checkpoint inhibitor or a co-stimulatory molecule through a linker sequence.

16. The polypeptide of claim 15, wherein the linker sequence comprises GGGGSGGGGS (SEQ ID NO: 29).

17. The polypeptide of claim 15, wherein the SIRP-gamma polypeptide is located either N-terminal or C-terminal of the polypeptide sequence comprising an immune checkpoint inhibitor or co-stimulatory molecule.

18. The polypeptide of claim 15, wherein the immune checkpoint inhibitor polypeptide comprises a sequence of a PD-1 or PD-L1 antagonist, a BTLA or CD160 antagonist, or a phosphatidylserine antagonist, e.g., MFGE8, TIM1, TIM3 or TIM4.

19. The polypeptide of claim 15, wherein the co-stimulatory molecule polypeptide comprises a sequence of a CD40 agonist, a 41BBL or CD137 agonist.

20. The polypeptide of claim 15, wherein the fusion or chimeric polypeptide comprises a sequence selected from:

```
                                                          (SEQ ID NO: 30)
DSPDRPWNPPTFSPALLVVTEGDNATFTCSFSNTSESFHVVWHRESPSGQTDTLAAFPEDRSQPGQDA

RFRVTQLPNGRDFFIMSVVRARRNDSGTYVCGVISLAPKIQIKESLRAELRVTERGGGGSGGGGSEEE

LQIIQPEKLLLVTVGKTATLHCTITSLFPVGPIQWFRGVGPGRVLIYNQKDGHFPRVTTVSDGTKRNN

MDFSIRISSITPADVGTYYCVKFRKGSPEDVEFKSGPGTEMALGAKPS;

(SEQ ID NO: 31)
EEELQIIQPEKLLLVTVGKTATLHCTITSLFPVGPIQWFRGVGPGRVLIYNQKDGHFPRVTTVSDGTKR

NNMDFSIRISSITPADVGTYYCVKFRKGSPEDVEFKSGPGTEMALGAKPSGGGGSGGGGSWNIHGKE

SCDVQLYIKRQSEHSILAGDPFELECPVKYCANRPHVTWCKLNGTTCVKLEDRQTSWKEEKNISFFIL

HFEPVLPNDNGSYRCSANFQSNLIESHSTTLYVTDVK;

(SEQ ID NO: 32)
EEELQIIQPEKLLLVTVGKTATLHCTITSLFPVGPIQWFRGVGPGRVLIYNQKDGHFPRVTTVSDGTKR

NNMDFSIRISSITPADVGTYYCVKFRKGSPEDVEFKSGPGTEMALGAKPSGGGGSGGGGSELNGCAN

PLGLKNNSIPDKQITASSSYKTWGLHLFSWNPSYARLDKQGNFNAWVAGSYGNDQWLQVDLGSSK

EVTGIITQGARNFGSVQFVASYKVAYSNDSANWTEYQDPRTGSSKIFPGNWDNHSHKKNLFETPILA

RYVRILPVAWHNRIALRLELLGC;

(SEQ ID NO: 33)
EEELQIIQPEKLLLVTVGKTATLHCTITSLFPVGPIQWFRGVGPGRVLIYNQKDGHFPRVTTVSDGTKR

NNMDFSIRISSITPADVGTYYCVKFRKGSPEDVEFKSGPGTEMALGAKPSGGGGSGGGGSVAGSVKV

GGEAGPSVTLPCHYSGAVTSMCWNRGSCSLFTCQNGIVWTNGTHVTYRKDTRYKLLGDLSRRDVSL

TIENTAVSDSGVYCCRVEHRGWFNDMKITVSLEIVPPKVTT;

(SEQ ID NO: 34)
EEELQIIQPEKLLLVTVGKTATLHCTITSLFPVGPIQWFRGVGPGRVLIYNQKDGHFPRVTTVSDGTKR

NNMDFSIRISSITPADVGTYYCVKFRKGSPEDVEFKSGPGTEMALGAKPSGGGGSGGGGSSEVEYRA

EVGQNAYLPCFYTPAAPGNLVPVCWGKGACPVFECGNVVLRTDERDVNYWTSRYWLNGDFRKGD

VSLTIENVTLADSGIYCCRIQIPGIMNDEKFNLKLVIKPAKVTPA;

(SEQ ID NO: 35)
EEELQIIQPEKLLLVTVGKTATLHCTITSLFPVGPIQWFRGVGPGRVLIYNQKDGHFPRVTTVSDGTKR

NNMDFSIRISSITPADVGTYYCVKFRKGSPEDVEFKSGPGTEMALGAKPSGGGGSGGGGSTSETVVTE

VLGHRVTLPCLYSSWSHNSNSMCWGKDQCPYSGCKEALIRTDGMRVTSRKSAKYRLQGTIPRGDVS

LTILNPSESDSGVYCCRIEVPGWFNDVKINVRLNLQRASTTTDEKFNLKLVIKPAKVTPA;
```

-continued (SEQ ID NO: 36)
EEELQIIQPEKLLLVTVGKTATLHCTITSLFPVGPIQWFRGVGPGRVLIYNQKDGHFPRVTTVSDGTKR

NNMDFSIRISSITPADVGTYYCVKFRKGSPEDVEFKSGPGTEMALGAKPSGGGGSGGGGSGDQNPQI

AAHVISEASSKTTSVLQWAEKGYYTMSNNLVTLENGKQLTVKRQGLYYIYAQVTFCSNREASSQAP

FIASLCLKSPGRFERILLRAANTHSSAKPCGQQSIHLGGVFELQPGASVFVNVTDPSQVSHGTGFTSFG

LLKL;

(SEQ ID NO: 37)
EEELQIIQPEKLLLVTVGKTATLHCTITSLFPVGPIQWFRGVGPGRVLIYNQKDGHFPRVTTVSDGTKR

NNMDFSIRISSITPADVGTYYCVKFRKGSPEDVEFKSGPGTEMALGAKPSGGGGSGGGGSDPAGLLD

LRQGMFAQLVAQNVLLIDGPLSWYSDPGLAGVSLTGGLSYKEDTKELVVAKAGVYYVFFQMELRR

VVAGEGSGSVSLALHLMPLRSAAGAAALALTVDLPPASSEARNSAFGFQGRLLHLSAGQRLGVHLH

TEARARHAWQLTQGATVLGLFRVTPEIPA;

(SEQ ID NO: 38)
EEELQIIQPEKLLLVTVGKTATLHCTITSLFPVGPIQWFRGVGPGRVLIYNQKDGHFPRVTTVSDGTKR

NNMDFSIRISSITPADVGTYYCVKFRKGSPEDVEFKSGPGTEMALGAKPSGGGGSGGGGSAPTSSSTK

KTQLQLEHLLLDLQMILNGINNYKNPKLTRMLTFKFYMPKKATELKHLQCLEEELKPLEEVLNLAQS

KNFHLRPRDLISNINVIVLELKGSETTFMCEYADETATIVEFLNRWITFCQSIISTLT;
and (SEQ ID NO: 39)
EEELQIIQPEKLLLVTVGKTATLHCTITSLFPVGPIQWFRGVGPGRVLIYNQKDGHFPRVTTVSDGTKR

NNMDFSIRISSITPADVGTYYCVKFRKGSPEDVEFKSGPGTEMALGAKPSGGGGSGGGGSAPTSSSTK

KTQLQLEHLLLTLQMILNGINNYKNPKLTRMLTAKFYMPKKATELKHLQCLEEELKPLEEVLNLAQS

KNFHLRPRDLISNINVIVLELKGSETTFMCEYADETATIVEFLNRWITFCQSIISTLT.

21. The polypeptide of claim 1, wherein the SIRP-gamma polypeptide is a fusion or chimeric polypeptide, wherein the SIRP-gamma polypeptide is fused to a polypeptide sequence comprising a cytokine or an attenuated cytokine through a linker sequence, and wherein the cytokine or the attenuated cytokine is a cytokine polypeptide comprising a sequence of an IL2.

22. The polypeptide of claim 21, wherein the IL2 comprises a polypeptide sequence comprising mutations D20T and F42A.

23. The polypeptide of claim 21, wherein the SIRP-gamma polypeptide is located either N-terminal or C-terminal of the polypeptide sequence comprising the cytokine or the attenuated cytokine.

* * * * *

UNITED STATES PATENT AND TRADEMARK OFFICE
CERTIFICATE OF CORRECTION

PATENT NO. : 9,845,345 B2
APPLICATION NO. : 15/157291
DATED : December 19, 2017
INVENTOR(S) : Aaron Michael Ring et al.

Page 1 of 1

It is certified that error appears in the above-identified patent and that said Letters Patent is hereby corrected as shown below:

In the Claims

At Column 107, Claim 14, please delete "(SEQ ID NO: 9) EEELQIIQPDKSVLVAAGETATLRCTITSLFPVGPIQWFRGAGPGRVLIYNQRDGPFPRVTTVSDGTKR;"

At Column 107, Claim 14, please delete "(SEQ ID NO: 12) EEELQIIQPDKSVLVAAGETATLRCTITSLFPVGPIQWFRGAGPGRVLIYNQRQGPFPRVTTVSDTTKRNNMDFSI RIGNITPADAGTYYCIKFRKGSPDDVEFKSGAGTELSVRAKPS; (SEQ ID NO: 3) EEELQIIQPEKLLLVTVGKTATLHCTITSLFPVGPVLWFRGVGPGRVLIYNQRQGPFPRVTTVSDTTKRNNMDFSI RISSITPADVGTYYCIKFRKGSPENVEFKSGPGTEMALGAKPS; (SEQ ID NO: 13) EEELQIIQPEKLLLVTVGKTATLHCTITSLFPVGPIQWFRGVGPGRVLIYNQREGPFPRVTTVSDGTKRNNMDFSI RISSITPADVGTYYCVKFRKGSPEDVEFKSGPGTEMALGAKPS; (SEQ ID NO: 42) EEELQMIQPEKLLLVTVGKTATLHCTVTSLLPVGPVLWFRGVGPGRELIYNQKEGHFPRVTTVSDLTKRNNMDF SIRISSITPADVGTYYCVKFRKGSPENVEFKSGPGTEMALGAKPS; (SEQ ID NO: 14) EEELQIIQPDKSVLVAAGETATLRCTITSLFPVGPIQWFRGAGPGRVLIYNQRDGPFPRVTTVSDGTKRNNMDFSI RISSITPADVGTYYCIKFRKGIPEDVEFKSGPGTEMALGAKPS; (SEQ ID NO: 15) EEELQIIQPDKSVLVAAGETATLRCTITSLFPVGPIQWFRGAGPGRVLIYNQRDGPFPRVTTVSDGTKRNNMDFSI RISSITPADVGTYYCIKFRKGIPEDVEFKSGPGTXWH, wherein X is A, R, N, D, C, Q, E, G, H, I, L, K, M, F, P, S, T, W, Y, or V; (SEQ ID NO: 16) EEELQIIQPDKSVLVAAGETATLRCTITSLFPVGPIQWFRGAGPGRVLIYNQKDGPFPRVTTVSDGTKRNNMDFSI RISSITPADVGTYYCIKFRKGTPEDVEFKSGPGTEMALGAKPS;"

Signed and Sealed this
Seventeenth Day of March, 2020

Andrei Iancu
*Director of the United States Patent and Trademark Office*